United States Patent
Cho et al.

(10) Patent No.: US 9,975,960 B2
(45) Date of Patent: May 22, 2018

(54) ANTI-HER2 ANTIBODY AND ANTI-C-MET/ANTI-HER2 BISPECIFIC ANTIBODIES COMPRISING THE SAME

(71) Applicant: Samsung Electronics Co., Ltd., Suwon-si, Gyeonggi-do (KR)

(72) Inventors: Mi Young Cho, Seoul (KR); Powei Lin, Hwaseong-si (KR); Kwang Ho Cheong, Seoul (KR); Jae Woong Hwang, Seoul (KR); Geun Woong Kim, Yongin-si (KR); Han Na Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days. days.

(21) Appl. No.: 14/709,214

(22) Filed: May 11, 2015

(65) Prior Publication Data

US 2015/0322162 A1 Nov. 12, 2015

(30) Foreign Application Priority Data

May 9, 2014 (KR) ........................ 10-2014-0055665
Apr. 20, 2015 (KR) ........................ 10-2015-0055501

(51) Int. Cl.
| | | |
|---|---|---|
| *C07K 16/32* | (2006.01) | |
| *C07K 16/40* | (2006.01) | |
| *A61K 39/395* | (2006.01) | |
| *C07K 16/22* | (2006.01) | |
| *C07K 16/30* | (2006.01) | |
| *C07K 16/28* | (2006.01) | |
| *A61K 39/00* | (2006.01) | |

(52) U.S. Cl.
CPC ............ *C07K 16/32* (2013.01); *A61K 39/395* (2013.01); *C07K 16/2863* (2013.01); *C07K 16/40* (2013.01); *A61K 39/39533* (2013.01); *A61K 39/39558* (2013.01); *A61K 2039/507* (2013.01); *C07K 2317/24* (2013.01); *C07K 2317/31* (2013.01); *C07K 2317/34* (2013.01); *C07K 2317/52* (2013.01); *C07K 2317/56* (2013.01); *C07K 2317/565* (2013.01); *C07K 2317/622* (2013.01); *C07K 2317/73* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,563,696 B2 | 10/2013 | Cheong et al. | |
| 2005/0079184 A1 | 4/2005 | Hsing-Chang et al. | |
| 2009/0203538 A1* | 8/2009 | Sugioka ............... | C07K 16/005 506/9 |
| 2010/0254988 A1* | 10/2010 | Bossenmaier ......... | C07K 16/32 424/136.1 |
| 2013/0089557 A1* | 4/2013 | Cheong .............. | C07K 16/2863 424/138.1 |
| 2014/0294834 A1 | 10/2014 | Harms et al. | |
| 2014/0294838 A1 | 10/2014 | Cho et al. | |
| 2015/0038684 A1 | 2/2015 | Jensen | |

FOREIGN PATENT DOCUMENTS

| | | | |
|---|---|---|---|
| KR | 2011-0047698 A | 5/2011 | |
| KR | 2014-0119318 A | 10/2014 | |
| WO | WO 2008007648 A1 * | 1/2008 | ........... C07K 16/005 |
| WO | WO 2013/033008 A2 | 3/2013 | |
| WO | WO 2013/123061 A1 | 8/2013 | |

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Bostrom et al., Variants of the Antibody Herceptin That Interact with HER2 and VEGF at the Antigen Binding Site, *Science*, 323:1610-14 (2009).
Chen et al., "MET activation mediates resistance to lapatinib inhibition of HER2-amplified gastric cancer cells", *Mol. Cancer Ther.* 11(3): 660-669 (2012).
Corso et al., "Activation of HER family members in gastric carcinoma cells mediates resistance to MET inhibition", *Molecular Cancer*, 9(121): 1-13 (2010).
Schaefer et al., "A Two-in-Oe Antibody against HER3 and EGFR Has Superior Inhibitory Activity Compared with Monospecific Antibodies", *Cancer Cell*, 20: 472-486 (2011).
Shattuck et al., "Met Receptor Contributes to Trastuzumab Resistance of Her2-Overexpressing Breast Cancer Cells", *Cancer Research*, 68: 1471-77 (2008).
Yang et al., "CDR Walking Mutagenesis for the Affinity Maturation of a Potent Human Anti-HIV-1 Antibody into the Picomolar Range", *J. Mol. Biol.* 254: 392-403 (1995).

* cited by examiner

*Primary Examiner* — Hong Sang
(74) *Attorney, Agent, or Firm* — Leydig, Voit & Mayer, Ltd.

(57) ABSTRACT

An anti-HER2 antibody, an anti-c-Met/anti-HER2 bispecific antibody including the same, method for preparing same, and a method of preventing and/or treating a cancer using the same are provided.

18 Claims, 3 Drawing Sheets

SEQUENCE LISTING

```
<160> NUMBER OF SEQ ID NOS: 162

<210> SEQ ID NO 1
<211> LENGTH: 5
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
 1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic heavy chain CDR2 of AbF46

<400> SEQUENCE: 2

Phe Ile Arg Asn Lys Ala Asn Gly Tyr Thr Thr Glu Tyr Ser Ala Ser
 1               5                  10                  15

Val Lys Gly
```

```
<210> SEQ ID NO 3
<211> LENGTH: 6
<212> TYPE: PRT
<213> ORGANISM: Artificial Sequence
<220> FEATURE:
<223> OTHER INFORMATION: Synthetic heavy chain CDR3 of AbF46

<400> SEQUENCE: 3

Asp Asn Trp Phe Ala Tyr
  1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: MOD_RES
<222> LOCATION: (1)
<223> OTHER INFORMATION: Xaa is Pro or Ser or absent
<220> FEATURE:
<221> NAME/KEY: MOD_RES
<222> LOCATION: (2)
<223> OTHER INFORMATION: Xaa is Glu or Asp

<400> SEQUENCE: 4

Xaa Xaa Tyr Tyr Met Ser
  1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: MOD_RES
<222> LOCATION: (3)
<223> OTHER INFORMATION: Xaa is Asn or Lys
<220> FEATURE:
<221> NAME/KEY: MOD_RES
<222> LOCATION: (4)
<223> OTHER INFORMATION: Xaa is Ala or Val
<220> FEATURE:
<221> NAME/KEY: MOD_RES
<222> LOCATION: (7)
<223> OTHER INFORMATION: Xaa is Asn or Thr

<400> SEQUENCE: 5

Arg Asn Xaa Xaa Asn Gly Xaa Thr
  1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
<220> FEATURE:
<221> NAME/KEY: MOD_RES
<222> LOCATION: (5)
<223> OTHER INFORMATION: Xaa is Ser or Thr

<400> SEQUENCE: 6

Asp Asn Trp Leu Xaa Tyr
  1               5

<210> SEQ ID NO 7
<211> LENGTH: 17
```

<212> TYPE: PRT
<213> ORGANISM: Artificial Sequence
<220> FEATURE:
<223> OTHER INFORMATION: Synthetic light chain CDR1 of c-Met antibody
<220> FEATURE:
<221> NAME/KEY: MOD_RES
<222> LOCATION: (4)
<223> OTHER INFORMATION: Xaa is His, Arg, Gln or Lys
<220> FEATURE:
<221> NAME/KEY: MOD_RES
<222> LOCATION: (9)
<223> OTHER INFORMATION: Xaa is Ser or Trp
<220> FEATURE:
<221> NAME/KEY: MOD_RES
<222> LOCATION: (12)
<223> OTHER INFORMATION: Xaa is His or Gln
<220> FEATURE:
<221> NAME/KEY: MOD_RES
<222> LOCATION: (13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
 1               5                  10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: MOD_RES
<222> LOCATION: (2)
<223> OTHER INFORMATION: Xaa is Ala or Gly
<220> FEATURE:
<221> NAME/KEY: MOD_RES
<222> LOCATION: (4)
<223> OTHER INFORMATION: Xaa is Thr or Lys
<220> FEATURE:
<221> NAME/KEY: MOD_RES
<222> LOCATION: (7)
<223> OTHER INFORMATION: Xaa is Ser or Pro

<400> SEQUENCE: 8

Trp Xaa Ser Xaa Arg Val Xaa
 1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: MOD_RES
<222> LOCATION: (1)
<223> OTHER INFORMATION: Xaa is Gly, Ala or Gln
<220> FEATURE:
<221> NAME/KEY: MOD_RES
<222> LOCATION: (6)
<223> OTHER INFORMATION: Xaa is Arg, His, Ser, Ala, Gly or Lys
<220> FEATURE:
<221> NAME/KEY: MOD_RES
<222> LOCATION: (8)
<223> OTHER INFORMATION: Xaa is Leu, Tyr, Phe or Met

<400> SEQUENCE: 9

Xaa Gln Ser Tyr Ser Xaa Pro Xaa Thr
 1               5

```
<210> SEQ ID NO 10
<211> LENGTH: 17
<212> TYPE: PRT
<213> ORGANISM: Artificial Sequence
<220> FEATURE:
<223> OTHER INFORMATION: Synthetic light chain CDR1 of AbF46

<400> SEQUENCE: 10

Lys Ser Ser Gln Ser Leu Leu Ala Ser Gly Asn Gln Asn Asn Tyr Leu
 1               5                  10                  15
Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

Trp Ala Ser Thr Arg Val Ser
 1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic light chain CDR3 of AbF46

<400> SEQUENCE: 12

Gln Gln Ser Tyr Ser Ala Pro Leu Thr
 1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13

Gln Gln Ser Tyr Ser Arg Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic CDR-L3 derived from L3-3 clone

<400> SEQUENCE: 15

Ala Gln Ser Tyr Ser His Pro Phe Ser
 1               5
```

```
<210> SEQ ID NO 16
<211> LENGTH: 9
<212> TYPE: PRT
<213> ORGANISM: Artificial Sequence
<220> FEATURE:
<223> OTHER INFORMATION: Synthetic CDR-L3 derived from L3-5 clone

<400> SEQUENCE: 16

Gln Gln Ser Tyr Ser Arg Pro Phe Thr
 1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti
      c-Met humanized antibody(huAbF46-H4)

<400> SEQUENCE: 17

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 18

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110
```

Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 19

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gly Gln
                 85                  90                  95

Ser Tyr Ser Arg Pro Leu Thr Phe Gly Gln Gly Thr Lys Val Glu Ile
            100                 105                 110
```

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 20

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Ala Gln
                 85                  90                  95

Ser Tyr Ser His Pro Phe Ser Phe Gly Gln Gly Thr Lys Val Glu Ile
            100                 105                 110
```

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Phe Thr Phe Gly Gln Gly Thr Lys Val Glu Ile
            100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic CDR-H1 derived from H11-4 clone

<400> SEQUENCE: 22

Pro Glu Tyr Tyr Met Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23

Pro Asp Tyr Tyr Met Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

Ser Asp Tyr Tyr Met Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic CDR-H2 derived from YC244 clone

<400> SEQUENCE: 25

Arg Asn Asn Ala Asn Gly Asn Thr
1               5

```
<210> SEQ ID NO 26
<211> LENGTH: 8
<212> TYPE: PRT
<213> ORGANISM: Artificial Sequence
<220> FEATURE:
<223> OTHER INFORMATION: Synthetic CDR-H2 derived from YC321 clone

<400> SEQUENCE: 26

Arg Asn Lys Val Asn Gly Tyr Thr
  1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
  1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic CDR-H3 derived from YC374 clone

<400> SEQUENCE: 28

Asp Asn Trp Leu Thr Tyr
  1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu
  1               5                  10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

Lys Ser Ser Arg Ser Leu Leu Ser Ser Gly Asn His Lys Asn Tyr Leu
  1               5                  10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31

Lys Ser Ser Lys Ser Leu Leu Ala Ser Gly Asn Gln Asn Asn Tyr Leu
```

<210> SEQ ID NO 32
<211> LENGTH: 17
<212> TYPE: PRT
<213> ORGANISM: Artificial Sequence
<220> FEATURE:
<223> OTHER INFORMATION: Synthetic CDR-L1 derived from L1-12 clone

<400> SEQUENCE: 32

Lys Ser Ser Arg Ser Leu Leu Ala Ser Gly Asn Gln Asn Asn Tyr Leu
1               5                   10                  15
Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33

Lys Ser Ser His Ser Leu Leu Ala Ser Gly Asn Gln Asn Asn Tyr Leu
1               5                   10                  15
Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34

Trp Ala Ser Lys Arg Val Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone

<400> SEQUENCE: 35

Trp Gly Ser Thr Arg Val Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic CDR-L2 derived from L2-16 clone

<400> SEQUENCE: 36

Trp Gly Ser Thr Arg Val Pro
1               5

<210> SEQ ID NO 37
<211> LENGTH: 9
<212> TYPE: PRT
<213> ORGANISM: Artificial Sequence
<220> FEATURE:

<223> OTHER INFORMATION: Synthetic CDR-L3 derived from L3-32 clone

<400> SEQUENCE: 37

Gln Gln Ser Tyr Ser Lys Pro Phe Thr
 1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic nucleotide sequence of heavy chain
      of chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38

```
gaattcgccg ccaccatgga atggagctgg gttttctcg taacactttt aaatggtatc     60
cagtgtgagg tgaagctggt ggagtctgga ggaggcttgg tacagcctgg ggttctctg    120 agactctcct gtgcaacttc tgggttcacc ttcactgatt actacatgag ctgggtccgc    180
cagcctccag aaaggcact tgagtggttg ggttttatta aaacaaagc taatggttac    240 acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactggggc caagggactc tggtcactgt ctctgcagct    420
agcaccaagg gcccatcggt cttcccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
```

```
tacaagtgca aggtctccaa caaagccctc ccagccccca tcgagaaaac catctccaaa    1080 gccaagggc agccccgaga accacaggtg tacaccctgc ccccatcccg ggaggagatg     1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416
```

<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain
      of chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39

```
gaattcacta gtgattaatt cgccgccacc atggattcac aggcccaggt cctcatgttg    60
ctgctgctat cggtatctgg tacctgtgga gacattttga tgacccagtc tccatcctcc    120
ctgactgtgt cagcaggaga gaaggtcact atgagctgca agtccagtca gagtctttta    180
gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                            759
```

<210> SEQ ID NO 40
<211> LENGTH: 447
<212> TYPE: PRT
<213> ORGANISM: Artificial Sequence
<220> FEATURE:
<223> OTHER INFORMATION: Synthetic amino acid sequence of H1-heavy

<400> SEQUENCE: 40

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
                20                  25                  30

Tyr Met Ser Trp Val Arg Gln Ala Pro Gly Lys Gly Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic amino acid sequence of H4-heavy

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

```
Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic amino acid sequence of H1-light

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125
```

```
Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
            210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
  1               5                  10                  15

Glu Pro Ala Ser Ile Ser Cys Lys Ser Ser Gln Ser Leu Leu Ala Ser
             20                  25                  30

Gly Asn Gln Asn Asn Tyr Leu Ala Trp His Leu Gln Lys Pro Gly Gln
         35                  40                  45

Ser Pro Gln Met Leu Ile Ile Trp Ala Ser Thr Arg Val Ser Gly Val
     50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                 85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
            210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light
```

<400> SEQUENCE: 45

```
Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Ala Ser
             20                  25                  30

Gly Asn Gln Asn Asn Tyr Leu Ala Trp Tyr Gln Gln Lys Pro Gly Gln
         35                  40                  45

Pro Pro Lys Leu Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gly Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220
```

<210> SEQ ID NO 46
<211> LENGTH: 219
<212> TYPE: PRT
<213> ORGANISM: Artificial Sequence
<220> FEATURE:
<223> OTHER INFORMATION: Synthetic amino acid sequence of H4-light

<400> SEQUENCE: 46

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Ala Pro Leu Thr Phe Gly Gln Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
```

```
                130               135               140
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215

<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg gctggagtg gttgggcttt attagaaaca agctaacgg ttacaccaca       180
gaatacagtg cgtctgtgaa aggcagattc accatctcaa gagataattc aaagaactca    240
ctgtatctgc aaatgaacag cctgaaaacc gaggacacgg ccgtgtatta ctgtgctaga    300
gataactggt ttgcttactg gggtcaagga accctggtca ccgtctcctc ggctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga gatgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa atgactcgag                                    1350

<210> SEQ ID NO 48
<211> LENGTH: 1350
<212> TYPE: DNA
<213> ORGANISM: Artificial Sequence
<220> FEATURE:
```

<223> OTHER INFORMATION: Synthetic nucleotide sequence of H3-heavy

<400> SEQUENCE: 48

```
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca agctaacgg ttacaccaca      180
gaatacagtg cgtctgtgaa aggcagattc accatctcaa gagataattc aaagaactca    240
ctgtatctgc aaatgaacag cctgcgtgct gaggacacgg ccgtgtatta ctgtgctaga    300
gataactggt ttgcttactg gggtcaagga accctggtca ccgtctcctc ggctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt     660
gacaaaactc acacatgccc accgtgccca gcacctgaac tcctgggggg accgtcagtc    720
ttcctcttcc cccaaaacc caaggacacc ctcatgatct cccggacccc tgaggtcaca     780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga gatgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa atgactcgag                                    1350
```

<210> SEQ ID NO 49
<211> LENGTH: 1350
<212> TYPE: DNA
<213> ORGANISM: Artificial Sequence
<220> FEATURE:
<223> OTHER INFORMATION: Synthetic nucleotide sequence of H4-heavy

<400> SEQUENCE: 49

```
gaggttcagc tggtggagtc tggcggtggc ctggtgcagc cagggggctc actccgtttg      60
tcctgtgcag cttctggctt caccttcact gattactaca tgagctgggt gcgtcaggcc    120
ccgggtaagg gcctggaatg gttgggtttt attagaaaca agctaatgg ttacacaaca     180
gagtacagtg catctgtgaa gggtcgtttc actataagca gagataattc aaaaacaca    240
ctgtacctgc agatgaacag cctgcgtgct gaggacactg ccgtctatta ttgtgctaga    300
gataactggt ttgcttactg gggccaaggg actctggtca ccgtctcctc ggctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
```

```
aacgtgaatc acaagcccag caacaccaag gtggacaaga aagttgagcc caaatcttgt    660
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga gatgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa atgactcgag                                    1350

<210> SEQ ID NO 50
<211> LENGTH: 669
<212> TYPE: DNA
<213> ORGANISM: Artificial Sequence
<220> FEATURE:
<223> OTHER INFORMATION: Synthetic nucleotide sequence of H1-light

<400> SEQUENCE: 50
gacatcgtga tgacccagtc tccagactcc ctggctgtgt ctctgggcga gagggccacc     60
atcaactgca gtccagcca gagtctttta gctagcggca accaaaataa ctacttagct    120
tggcaccagc agaaaccagg acagcctcct aagatgctca tttatttggc atctacccgg    180
gtatccgggg tccctgaccg attcagtggc agcgggtctg ggacagattt cactctcacc    240
atcagcagcc tgcaggctga agatgtggca gtttattact gtcagcaatc ctatagtgct    300
cctctcacgt tcggaggcgg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tgactcgag                                                            669

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51
gatattgtga tgacccagac tccactctcc ctgcccgtca cccctggaga gccggcctcc     60
atctcctgca gtccagtca gagtctttta gctagtggca accaaaataa ctacttggcc    120 tggcaccctgc agaagccagg gcagtctcca cagatgctga tcatttgggc atccactagg    180
gtatctggag tcccagacag gttcagtggc agtgggtcag gcactgattt cacactgaaa    240
```

| | | |
|---|---|---|
| atcagcaggg tggaggctga ggatgttgga gtttattact gccagcagtc ctacagcgct | 300 | |
| ccgctcacgt tcggacaggg taccaagctg gagctcaaac gtacggtggc tgcaccatct | 360 | |
| gtcttcatct tcccgccatc tgatgagcag ttgaaatctg gaactgcctc tgttgtgtgc | 420 | |
| ctgctgaata acttctatcc cagagaggcc aaagtacagt ggaaggtgga taacgccctc | 480 | |
| caatcgggta actcccagga gagtgtcaca gagcaggaca gcaaggacag cacctacagc | 540 | |
| ctcagcagca ccctgacgct gagcaaagca gactacgaga aacacaaagt ctacgcctgc | 600 | |
| gaagtcaccc atcagggcct gagctcgccc gtcacaaaga gcttcaacag gggagagtgt | 660 | |
| tgactcgag | 669 | |

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52

| | | |
|---|---|---|
| gacatcgtga tgacccagtc tccagactcc ctggctgtgt ctctgggcga gagggccacc | 60 | |
| atcaactgca gtccagcca gagtcttta gctagcggca accaaaataa ctacttagct | 120 | |
| tggtaccagc agaaaccagg acagcctcct aagctgctca ttatttgggc atctacccgg | 180 | |
| gtatccgggg tccctgaccg attcagtggc agcgggtctg gacagattt cactctcacc | 240 | |
| atcagcagcc tgcaggctga agatgtggca gtttattact gtcagcaatc ctatagtgct | 300 | |
| cctctcacgt tcggaggcgg taccaaggtg gagatcaaac gtacggtggc tgcaccatct | 360 | |
| gtcttcatct tcccgccatc tgatgagcag ttgaaatctg gaactgcctc tgttgtgtgc | 420 | |
| ctgctgaata acttctatcc cagagaggcc aaagtacagt ggaaggtgga taacgccctc | 480 | |
| caatcgggta actcccagga gagtgtcaca gagcaggaca gcaaggacag cacctacagc | 540 | |
| ctcagcagca ccctgacgct gagcaaagca gactacgaga aacacaaagt ctacgcctgc | 600 | |
| gaagtcaccc atcagggcct gagctcgccc gtcacaaaga gcttcaacag gggagagtgt | 660 | |
| tgactcgag | 669 | |

<210> SEQ ID NO 53
<211> LENGTH: 669
<212> TYPE: DNA
<213> ORGANISM: Artificial Sequence
<220> FEATURE:
<223> OTHER INFORMATION: Synthetic nucleotide sequence of H4-light

<400> SEQUENCE: 53

| | | |
|---|---|---|
| gatatccaga tgacccagtc cccgagctcc ctgtccgcct ctgtgggcga tagggtcacc | 60 | |
| atcacctgca gtccagtca gagtctttta gctagtggca accaaaataa ctacttggcc | 120 | |
| tggcaccaac agaaaccagg aaaagctccg aaaatgctga ttatttgggc atccactagg | 180 | |
| gtatctggag tccttctcg cttctctgga tccgggtctg gacgatttt cactctgacc | 240 | |
| atcagcagtc tgcagccgga agacttcgca acttattact gtcagcagtc ctacagcgct | 300 | |
| ccgctcacgt tcggacaggg taccaaggtg gagatcaaac gtacggtggc tgcaccatct | 360 | |
| gtcttcatct tcccgccatc tgatgagcag ttgaaatctg gaactgcctc tgttgtgtgc | 420 | |
| ctgctgaata acttctatcc cagagaggcc aaagtacagt ggaaggtgga taacgccctc | 480 | |
| caatcgggta actcccagga gagtgtcaca gagcaggaca gcaaggacag cacctacagc | 540 | |
| ctcagcagca ccctgacgct gagcaaagca gactacgaga aacacaaagt ctacgcctgc | 600 | |

```
gaagtcaccc atcagggcct gagctcgccc gtcacaaaga gcttcaacag gggagagtgt    660
tgactcgag                                                            669
```

<210> SEQ ID NO 54
<211> LENGTH: 23
<212> TYPE: PRT
<213> ORGANISM: Artificial Sequence
<220> FEATURE:
<223> OTHER INFORMATION: Synthetic linker between VH and VL

<400> SEQUENCE: 54

Gly Leu Gly Gly Leu Gly Gly Gly Ser Gly Gly Gly Gly Ser Gly
 1               5                  10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of
      huAbF46 antibody

<400> SEQUENCE: 55

```
gctagcgttt tagcagaagt tcaattggtt gaatctggtg gtggtttggt tcaaccaggt     60
ggttctttga gattgtcttg tgctgcttct ggttttactt tcaccgatta ttacatgtcc    120
tgggttagac aagctccagg taaaggtttg aatggttgg gtttcattag aaacaaggct    180
aacggttaca ctaccgaata ttctgcttct gttaaggta gattcaccat ttctagagac    240
aactctaaga cacccttgta cttgcaaatg aactccttga gagctgaaga tactgctgtt    300
tattactgcg ctagagataa ttggtttgct tattggggtc aaggtacttt ggttactgtt    360
tcttctggcc tcgggggcct cggaggagga ggtagtggcg gaggaggctc cggtggatcc    420
agcggtgtgg gttccgatat tcaaatgacc caatctccat cttctttgtc tgcttcagtt    480
ggtgatagag ttaccattac ttgtaagtcc tcccaatctt tgttggcttc tggtaatcag    540
aacaattact ggcttggca tcaacaaaaa ccaggtaaag ctccaaagat gttgattatt    600
tgggcttcta ccagagtttc tggtgttcca tctagatttt ctggttctgg ttccggtact    660
gattttactt tgaccatttc atccttgcaa ccagaagatt tcgctactta ctactgtcaa    720
caatcttact ctgctccatt gactttggt caaggtacaa aggtcgaaat caagagagaa    780
ttcggtaagc ctatccctaa ccctctcctc ggtctcgatt ctacgggtgg tggtggatct    840
ggtggtggtg ttctggtgg tggtggttct caggaactga caactatatg cgagcaaatc    900
ccctcaccaa ctttagaatc gacgccgtac tctttgtcaa cgactactat tttggccaac    960
gggaaggcaa tgcaaggagt ttttgaatat acaaatcag taacgtttgt cagtaattgc   1020
ggttctcacc cctcaacaac tagcaaaggc agccccataa acacacagta tgttttttga   1080
gtttaaac                                                            1088
```

<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including
      polynucleotide encoding scFv of huAbF46 antibody
<220> FEATURE:

```
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg tttttcaata ttttctgtta ttgctagcgt tttagcagaa gttcaattgg     600
ttgaatctgg tggtggtttg gttcaaccag gtggttcttt gagattgtct tgtgctgctt     660
ctggttttac tttcaccgat tattacatgt cctgggttag acaagctcca ggtaaaggtt     720
tggaatggtt gggtttcatt agaaacaagg ctaacggtta cactaccgaa tattctgctt     780
ctgttaaggg tagattcacc atttctagag acaactctaa gaacaccttg tacttgcaaa     840
tgaactcctt gagagctgaa gatactgctg tttattactg cgctagagat aattggtttg     900
cttattgggg tcaaggtact ttggttactg tttcttctgg cctcggggc ctcggaggag     960 gaggtagtgg cggaggaggc tccggtggat ccagcggtgt gggttccgat attcaaatga     1020
cccaatctcc atcttctttg tctgcttcag ttggtgatag agttaccatt acttgtaagt     1080
cctcccaatc tttgttggct tctggtaatc agaacaatta cttggcttgg catcaacaaa     1140
```

```
aaccaggtaa agctccaaag atgttgatta tttgggcttc taccagagtt tctggtgttc    1200
catctagatt ttctggttct ggttccggta ctgattttac tttgaccatt tcatccttgc    1260
aaccagaaga tttcgctact tactactgtc aacaatctta ctctgctcca ttgacttttg    1320
gtcaaggtac aaaggtcgaa atcaagagag aattcggtaa gcctatccct aaccctctcc    1380
tcggtctcga ttctacgggt ggtggtggat ctggtggtgg tggttctggt ggtggtggtt    1440
ctcaggaact gacaactata tgcgagcaaa tccccctcacc aactttagaa tcgacgccgt    1500
actctttgtc aacgactact attttggcca acgggaaggc aatgcaagga gttttttgaat    1560 attacaaatc agtaacgttt gtcagtaatt gcggttctca cccctcaaca actagcaaag    1620
gcagccccat aaacacacag tatgtttttt gagtttaaac ccgctgatct gataacaaca    1680
gtgtagatgt aacaaaatcg actttgttcc cactgtactt ttagctcgta caaaatacaa    1740 tatactttc atttctccgt aaacaacatg ttttcccatg taatatcctt ttctatttt     1800 cgttccgtta ccaactttac acatacttta tatagctatt cacttctata cactaaaaaa    1860
ctaagacaat tttaattttg ctgcctgcca tatttcaatt tgttataaat tcctataatt    1920
tatcctatta gtagctaaaa aaagatgaat gtgaatcgaa tcctaagaga attgggcaag    1980
tgcacaaaca atacttaaat aaatactact cagtaataac ctatttctta gcattttttga   2040 cgaaatttgc tattttgtta gagtctttta caccatttgt ctccacacct ccgcttacat    2100
caacaccaat aacgccattt aatctaagcg catcaccaac attttctggc gtcagtccac    2160
cagctaacat aaaatgtaag ctctcggggc tctcttgcct tccaacccag tcagaaatcg    2220
agttccaatc caaaagttca cctgtcccac ctgcttctga atcaaacaag ggaataaacg    2280
aatgaggttt ctgtgaagct gcactgagta gtatgttgca gtcttttgga aatacgagtc    2340
ttttaataac tggcaaaccg aggaactctt ggtattcttg ccacgactca tctccgtgca    2400
gttggacgat atcaatgccg taatcattga ccagagccaa aacatcctcc ttaggttgat    2460
tacgaaacac gccaaccaag tatttcggag tgcctgaact attttttatat gcttttacaa    2520 gacttgaaat tttccttgca ataaccgggt caattgttct cttttctattg ggcacacata    2580 taatacccag caagtcagca tcggaatcta gagcacattc tgcggcctct gtgctctgca    2640
agccgcaaac tttcaccaat ggaccagaac tacctgtgaa attaataaca gacatactcc    2700
aagctgcctt tgtgtgctta atcacgtata ctcacgtgct caatagtcac caatgccctc    2760
cctcttggcc ctctccttt ctttttcga ccgaatttct tgaagacgaa agggcctcgt       2820
gatacgccta ttttatagg ttaatgtcat gataataatg gtttcttagg acggatcgct     2880
tgcctgtaac ttacacgcgc ctcgtatctt ttaatgatgg aataatttgg gaatttactc    2940
tgtgtttatt tattttatg ttttgtattt ggattttaga aagtaaataa agaaggtaga     3000
agagttacgg aatgaagaaa aaaaaataaa caaaggttta aaaaatttca acaaaaagcg    3060
tactttacat atatatttat tagacaagaa aagcagatta aatagatata cattcgatta    3120
acgataagta aaatgtaaaa tcacaggatt ttcgtgtgtg gtcttctaca cagacaagat    3180
gaaacaattc ggcattaata cctgagagca ggaagagcaa gataaaaggt agtatttgtt    3240
ggcgatcccc ctagagtctt ttacatcttc ggaaaacaaa aactatttt tctttaattt    3300 cttttttac tttctatttt taatttatat atttatatta aaaaatttaa attataatta     3360
tttttatagc acgtgatgaa aaggaccag gtggcacttt tcggggaaat gtgcgcggaa     3420
cccctatttg tttattttc taaatacatt caaatatgta tccgctcatg agacaataac    3480
```

| | |
|---|---|
| cctgataaat gcttcaataa tattgaaaaa ggaagagtat gagtattcaa catttccgtg | 3540 |
| tcgcccttat tccctttttt gcggcatttt gccttcctgt ttttgctcac ccagaaacgc | 3600 |
| tggtgaaagt aaaagatgct gaagatcagt tgggtgcacg agtgggttac atcgaactgg | 3660 |
| atctcaacag cggtaagatc cttgagagtt ttcgccccga agaacgtttt ccaatgatga | 3720 |
| gcacttttaa agttctgcta tgtggcgcgg tattatcccg tgttgacgcc gggcaagagc | 3780 |
| aactcggtcg ccgcatacac tattctcaga atgacttggt tgagtactca ccagtcacag | 3840 |
| aaaagcatct tacggatggc atgacagtaa gagaattatg cagtgctgcc ataaccatga | 3900 |
| gtgataacac tgcggccaac ttacttctga acgatcgg aggaccgaag gagctaaccg | 3960 |
| cttttttgca acatggggg atcatgtaa ctcgccttga tcgttgggaa ccggagctga | 4020 |
| atgaagccat accaaacgac gagcgtgaca ccacgatgcc tgtagcaatg gcaacaacgt | 4080 |
| tgcgcaaact attaactggc gaactactta ctctagcttc ccggcaacaa ttaatagact | 4140 |
| ggatggaggc ggataaagtt gcaggaccac ttctgcgctc ggcccttccg gctggctggt | 4200 |
| ttattgctga taaatctgga gccggtgagc gtgggtctcg cggtatcatt gcagcactgg | 4260 |
| ggccagatgg taagccctcc cgtatcgtag ttatctacac gacgggcagt caggcaacta | 4320 |
| tggatgaacg aaatagacag atcgctgaga taggtgcctc actgattaag cattggtaac | 4380 |
| tgtcagacca gtttactca tatatacttt agattgattt aaaacttcat ttttaattta | 4440 |
| aaaggatcta ggtgaagatc ctttttgata atctcatgac caaaatccct aacgtgagt | 4500 |
| tttcgttcca ctgagcgtca gaccccgtag aaaagatcaa aggatcttct tgagatcctt | 4560 |
| ttttttctgcg cgtaatctgc tgcttgcaaa caaaaaaacc accgctacca gcggtggttt | 4620 |
| gtttgccgga tcaagagcta ccaactcttt ttccgaaggt aactggcttc agcagagcgc | 4680 |
| agataccaaa tactgtcctt ctagtgtagc cgtagttagg ccaccacttc aagaactctg | 4740 |
| tagcaccgcc tacatacctc gctctgctaa tcctgttacc agtggctgct gccagtggcg | 4800 |
| ataagtcgtg tcttaccggg ttggactcaa gacgatagtt accggataag cgcagcggt | 4860 |
| cgggctgaac ggggggttcg tgcacacagc ccagcttgga gcgaacgacc tacaccgaac | 4920 |
| tgagatacct acagcgtgag cattgagaaa gcgccacgct tcccgaaggg agaaaggcgg | 4980 |
| acaggtatcc ggtaagcggc agggtcggaa caggagagcg cacgagggag cttccagggg | 5040 |
| ggaacgcctg gtatctttat agtcctgtcg ggtttcgcca cctctgactt gagcgtcgat | 5100 |
| ttttgtgatg ctcgtcaggg gggcgagcc tatggaaaaa cgccagcaac gcggcctttt | 5160 |
| tacggttcct ggccttttgc tggccttttg ctcacatgtt ctttcctgcg ttatcccctg | 5220 |
| attctgtgga taaccgtatt accgcctttg agtgagctga taccgctcgc cgcagccgaa | 5280 |
| cgaccgagcg cagcgagtca gtgagcgagg aagcggaaga gcgcccaata cgcaaaccgc | 5340 |
| ctctccccgc gcgttggccg attcattaat gcagctggca cgacaggttt cccgactgga | 5400 |
| aagcgggcag tgagcgcaac gcaattaatg tgagttacct cactcattag gcaccccagg | 5460 |
| ctttacactt tatgcttccg gctcctatgt tgtgtggaat tgtgagcgga taacaatttc | 5520 |
| acacaggaaa cagctatgac catgattacg ccaagctcgg aattaaccct cactaaaggg | 5580 |
| aacaaaagct ggctagt | 5597 |

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

Glu Pro Lys Ser Cys Asp Cys His Cys Pro Pro Cys Pro
 1               5                  10

<210> SEQ ID NO 58
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-1 clone

<400> SEQUENCE: 58

| | | |
|---|---|---|
| gaattcacta gtgattaatt cgccgccacc atggattcac aggcccaggt cctcatgttg | 60 |
| ctgctgctat cggtatctgg tacctgtgga gatatccaga tgacccagtc cccgagctcc | 120 |
| ctgtccgcct ctgtgggcga tagggtcacc atcacctgca agtccagtca gagtctttta | 180 |
| gctagtggca accaaaataa ctacttggcc tggcaccaac agaaaccagg aaaagctccg | 240 |
| aaaatgctga ttatttgggc atccactagg gtatctggag tcccttctcg cttctctgga | 300 |
| tccgggtctg ggacggattt cactctgacc atcagcagtc tgcagccgga agacttcgca | 360 |
| acttattact gtcagcagtc ctacagccgc ccgtacacgt tcggacaggg taccaaggtg | 420 |
| gagatcaaac gtacg | 435 |

<210> SEQ ID NO 59
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-2 clone

<400> SEQUENCE: 59

| | | |
|---|---|---|
| gaattcacta gtgattaatt cgccgccacc atggattcac aggcccaggt cctcatgttg | 60 |
| ctgctgctat cggtatctgg tacctgtgga gatatccaga tgacccagtc cccgagctcc | 120 |
| ctgtccgcct ctgtgggcga tagggtcacc atcacctgca agtccagtca gagtctttta | 180 |
| gctagtggca accaaaataa ctacttggcc tggcaccaac agaaaccagg aaaagctccg | 240 |
| aaaatgctga ttatttgggc atccactagg gtatctggag tcccttctcg cttctctgga | 300 |
| tccgggtctg ggacggattt cactctgacc atcagcagtc tgcagccgga agacttcgca | 360 |
| acttattact gtgggcagtc ctacagccgt ccgctcacgt tcggacaggg taccaaggtg | 420 |
| gagatcaaac gtacg | 435 |

<210> SEQ ID NO 60
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-3 clone

<400> SEQUENCE: 60

| | | |
|---|---|---|
| gaattcacta gtgattaatt cgccgccacc atggattcac aggcccaggt cctcatgttg | 60 |
| ctgctgctat cggtatctgg tacctgtgga gatatccaga tgacccagtc cccgagctcc | 120 |
| ctgtccgcct ctgtgggcga tagggtcacc atcacctgca agtccagtca gagtctttta | 180 |
| gctagtggca accaaaataa ctacttggcc tggcaccaac agaaaccagg aaaagctccg | 240 |

-continued

```
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtgcacagtc ctacagccat ccgttctctt tcggacaggg taccaaggtg    420
gagatcaaac gtacg                                                     435
```

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3 derived from L3-5 clone

<400> SEQUENCE: 61

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtctttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtcagcagtc ctacagccgc ccgtttacgt tcggacaggg taccaaggtg    420
gagatcaaac gtacg                                                     435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic polypeptide consisting of heavy chain of huAbF46-H4-A1, U6-HC7 hinge and constant region of human IgG1

<400> SEQUENCE: 62

```
Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175
```

Ser Gly Ala Leu Thr Ser Gly Val His Thr Phe Pro Ala Val Leu Gln
        180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
        210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, U6-HC7 hinge and
      constant region of human IgG1

<400> SEQUENCE: 63
gaattcgccg ccaccatgga atggagctgg gttttttctcg taacactttt aaatggtatc      60
cagtgtgagg ttcagctggt ggagtctggc ggtggcctgg tgcagccagg gggctcactc     120
cgtttgtcct gtcagcttc tggcttcacc ttcactgatt actacatgag ctgggtgcgt     180
caggccccgg gtaagggcct ggaatggttg ggttttatta gaaacaaagc taatggttac     240
acaacagagt acagtgcatc tgtgaagggt cgtttcacta taagcagaga taattccaaa     300
aacacactgt acctgcagat gaacagcctg cgtgctgagg acactgccgt ctattattgt     360
gctagagata ctggtttgc ttactggggc caagggactc tggtcaccgt ctcctcggct     420

```
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
agctgcgatt gccactgtcc tcatgtccag cacctgaact cctgggggg accgtcagtc    780 ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atgactcgag                                    1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy chain
    of huAbF46-H4-A1, human IgG2 hinge and constant region of
    human IgG1

<400> SEQUENCE: 64

```
Met Glu Trp Ser Trp Val Phe Leu Val Thr Leu Leu Asn Gly Ile Gln
 1               5                  10                  15

Cys Glu Val Gln Leu Val Glu Ser Gly Gly Leu Val Gln Pro Gly
                20                  25                  30

Gly Ser Leu Arg Leu Ser Cys Ala Ala Ser Gly Phe Thr Phe Thr Asp
            35                  40                  45

Tyr Tyr Met Ser Trp Val Arg Gln Ala Pro Gly Lys Gly Leu Glu Trp
        50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175
```

Ser Gly Ala Leu Thr Ser Gly Val His Thr Phe Pro Ala Val Leu Gln
            180                 185                 190

Ser Ser Gly Leu Tyr Ser Leu Ser Val Val Thr Val Pro Ser Ser
            195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
            245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
            325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
            370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
    450                 455                 460

<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG1

<400> SEQUENCE: 65
gaattcgccg ccaccatgga atggagctgg gttttctcg taacactttt aaatggtatc      60
cagtgtgagg ttcagctggt ggagtctggc ggtggcctgg tgcagccagg gggctcactc    120
cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360

```
gctagagata actggtttgc ttactggggc caagggactc tggtcaccgt ctcctcggct      420
agcaccaagg gcccatcggt cttccccctg gcaccctcct ccaagagcac ctctgggggc      480
acagcggccc tgggctgcct ggtcaaggac tacttccccg aaccggtgac ggtgtcgtgg      540
aactcaggcg ccctgaccag cggcgtgcac accttcccgg ctgtcctaca gtcctcagga      600
ctctactccc tcagcagcgt ggtgaccgtg ccctccagca gcttgggcac ccagacctac      660
atctgcaacg tgaatcacaa gcccagcaac accaaggtgg acaagaaagt tgagaggaag      720
tgctgtgtgg agtgcccccc ctgcccagca cctgaactcc tggggggacc gtcagtcttc      780
ctcttccccc caaaacccaa ggacaccctc atgatctccc ggacccctga ggtcacatgc      840
gtggtggtgg acgtgagcca cgaagaccct gaggtcaagt tcaactggta cgtggacggc      900
gtggaggtgc ataatgccaa gacaaagccg cgggaggagc agtacaacag cacgtaccgt      960
gtggtcagcg tcctcaccgt cctgcaccag gactggctga atggcaagga gtacaagtgc     1020
aaggtctcca acaaagccct cccagccccc atcgagaaaa ccatctccaa agccaaaggg     1080
cagccccgag aaccacaggt gtacaccctg cccccatccc gggaggagat gaccaagaac     1140
caggtcagcc tgacctgcct ggtcaaaggc ttctatccca gcgacatcgc cgtggagtgg     1200
gagagcaatg ggcagccgga gaacaactac aagaccacgc tcccgtgct ggactccgac     1260 ggctccttct tcctctacag caagctcacc gtggacaaga gcaggtggca gcagggaac     1320 gtcttctcat gctccgtgat gcatgaggct ctgcacaacc actacacgca gaagagcctc     1380
tccctgtctc cgggtaaatg actcgag                                         1407

<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, human IgG2 hinge and constant region of
      human IgG2

<400> SEQUENCE: 66

Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
```

165                 170                 175
Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
            245                 250                 255

Pro Pro Lys Pro Lys Asp Thr Leu Met Ile Ser Arg Thr Pro Glu Val
        260                 265                 270

Thr Cys Val Val Val Asp Val Ser His Glu Asp Pro Glu Val Gln Phe
    275                 280                 285

Asn Trp Tyr Val Asp Gly Val Glu Val His Asn Ala Lys Thr Lys Pro
290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
            325                 330                 335

Ser Asn Lys Gly Leu Pro Ala Pro Ile Glu Lys Thr Ile Ser Lys Thr
        340                 345                 350

Lys Gly Gln Pro Arg Glu Pro Gln Val Tyr Thr Leu Pro Pro Ser Arg
    355                 360                 365

Glu Glu Met Thr Lys Asn Gln Val Ser Leu Thr Cys Leu Val Lys Gly
370                 375                 380

Phe Tyr Pro Ser Asp Ile Ala Val Glu Trp Ser Asn Gly Gln Pro
385                 390                 395                 400

Glu Asn Asn Tyr Lys Thr Thr Pro Pro Met Leu Asp Ser Asp Gly Ser
            405                 410                 415

Phe Phe Leu Tyr Ser Lys Leu Thr Val Asp Lys Ser Arg Trp Gln Gln
        420                 425                 430

Gly Asn Val Phe Ser Cys Ser Val Met His Glu Ala Leu His Asn His
    435                 440                 445

Tyr Thr Gln Lys Ser Leu Ser Leu Ser Pro Gly Lys
    450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG2

<400> SEQUENCE: 67
gaattcgccg ccaccatgga atggagctgg gtttttctcg taacactttt aaatggtatc      60
cagtgtgagg ttcagctggt ggagtctggc ggtggcctgg tgcagccagg ggctcactc     120 cgtttgtcct gtgcagcttc tggcttcacc ttcactgatt actacatgag ctgggtgcgt     180
caggccccgg gtaagggcct ggaatggttg gtttttatta gaaacaaagc taatggttac     240
acaacagagt acagtgcatc tgtgaagggg cgtttcacta taagcagaga taattccaaa     300
aacacactgt acctgcagat gaacagcctg cgtgctgagg acactgccgt ctattattgt     360

```
gctagagata actggtttgc ttactggggc caagggactc tggtcaccgt ctcctcggct      420
agcaccaagg gcccatcggt cttcccctg gcgccctgct ccaggagcac ctccgagagc       480
acagcggccc tgggctgcct ggtcaaggac tacttcccg aaccggtgac ggtgtcgtgg       540
aactcaggcg ctctgaccag cggcgtgcac accttcccag ctgtcctaca gtcctcagga     600
ctctactccc tcagcagcgt ggtgaccgtg ccctccagca acttcggcac ccagacctac     660
acctgcaacg tagatcacaa gcccagcaac accaaggtgg acaagacagt tgagcgcaaa     720
tgttgtgtcg agtgcccacc gtgcccagca ccacctgtgg caggaccgtc agtcttcctc     780
ttccccccaa aacccaagga caccctcatg atctcccgga cccctgaggt cacgtgcgtg     840
gtggtggacg tgagccacga agaccccgag gtccagttca actggtacgt ggacggcgtg     900
gaggtgcata atgccaagac aaagccacgg gaggagcagt tcaacagcac gttccgtgtg     960
gtcagcgtcc tcaccgttgt gcaccaggac tggctgaacg gcaaggagta caagtgcaag    1020
gtctccaaca aaggcctccc agcccccatc gagaaaacca tctccaaaac caaagggcag    1080
ccccgagaac cacaggtgta caccctgccc ccatcccggg aggagatgac caagaaccag    1140
gtcagcctga cctgcctggt caaaggcttc taccccagcg acatcgccgt ggagtgggag    1200
agcaatgggc agccggagaa caactacaag accacgcctc ccatgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaatgact cgag                                           1404
```

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light chain
     of huAbF46-H4-A1(H36Y) and human kappa constant region

<400> SEQUENCE: 68

```
Met Asp Ser Gln Ala Gln Val Leu Met Leu Leu Leu Leu Ser Val Ser
  1               5                  10                  15

Gly Thr Cys Gly Asp Ile Gln Met Thr Gln Ser Pro Ser Ser Leu Ser
             20                  25                  30

Ala Ser Val Gly Asp Arg Val Thr Ile Thr Cys Lys Ser Ser Gln Ser
         35                  40                  45

Leu Leu Ala Ser Gly Asn Gln Asn Asn Tyr Leu Ala Trp Tyr Gln Gln
     50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
```

165                 170                 175
Asp Asn Ala Leu Gln Ser Gly Asn Ser Gln Glu Ser Val Thr Glu Gln
              180                 185                 190

Asp Ser Lys Asp Ser Thr Tyr Ser Leu Ser Ser Thr Leu Thr Leu Ser
          195                 200                 205

Lys Ala Asp Tyr Glu Lys His Lys Val Tyr Ala Cys Glu Val Thr His
      210                 215                 220

Gln Gly Leu Ser Ser Pro Val Thr Lys Ser Phe Asn Arg Gly Glu Cys
225                 230                 235                 240

<210> SEQ ID NO 69
<211> LENGTH: 758
<212> TYPE: DNA
<213> ORGANISM: Artificial Sequence
<220> FEATURE:
<223> OTHER INFORMATION: Synthetic polynucleotide encoding polypeptide
      consisting of light chain of huAbF46-H4-A1(H36Y) and human kappa
      constant region

<400> SEQUENCE: 69
aattcactag tgattaattc gccgccacca tggattcaca ggcccaggtc ctcatgttgc      60
tgctgctatc ggtatctggt acctgtggag atatccagat gacccagtcc ccgagctccc     120
tgtccgcctc tgtgggcgat agggtcacca tcacctgcaa gtccagtcag agtctttag     180 ctagtggcaa ccaaaataac tacttggcct ggtaccaaca gaaaccagga aaagctccga     240
aaatgctgat tatttgggca tccactaggg tatctggagt cccttctcgc ttctctggat     300
ccgggtctgg gacggatttc actctgacca tcagcagtct gcagccggaa gacttcgcaa     360
cttattactg tcagcagtcc tacagccgcc gtacacgtt cggacagggt accaaggtgg     420
agatcaaacg tacggtggct gcaccatctg tcttcatctt cccgccatct gatgagcagt     480
tgaaatctgg aactgcctct gttgtgtgcc tgctgaataa cttctatccc agagaggcca     540
aagtacagtg gaaggtggat aacgccctcc aatcgggtaa ctcccaggag agtgtcacag     600
agcaggacag caaggacagc acctacagcc tcagcagcac cctgacgctg agcaaagcag     660
actacgagaa acacaaagtc tacgcctgcg aagtcaccca tcagggcctg agctcgcccg     720
tcacaaagag cttcaacagg ggagagtgtt gactcgag                             758

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light chain
      of huAbF46-H4-A1 and human kappa constant region

<400> SEQUENCE: 70

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp His Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp

```
                    85                  90                  95
Phe Thr Leu Thr Ile Ser Ser Leu Gln Pro Glu Asp Phe Ala Thr Tyr
                100                 105                 110

Tyr Cys Gln Gln Ser Tyr Ser Arg Pro Tyr Thr Phe Gly Gln Gly Thr
            115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic epitope in SEMA domain of c-Met

<400> SEQUENCE: 71

Phe Ser Pro Gln Ile Glu Glu Pro Ser Gln Cys Pro Asp Cys Val Val
 1               5                  10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic epitope in SEMA domain of c-Met

<400> SEQUENCE: 72

Pro Gln Ile Glu Glu Pro Ser Gln Cys Pro
 1               5                  10

<210> SEQ ID NO 73
<211> LENGTH: 5
<212> TYPE: PRT
<213> ORGANISM: Artificial Sequence
<220> FEATURE:
<223> OTHER INFORMATION: Synthetic epitope in SEMA domain of c-Met

<400> SEQUENCE: 73

Glu Glu Pro Ser Gln
 1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic heavy chain variable region of
      anti-c-Met antibody (AbF46 or huAbF46-H1)
```

<400> SEQUENCE: 74

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
            115

<210> SEQ ID NO 75
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody (AbF46 or huAbF46-H1)

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      anti-c-Met antibody (AbF46 or huAbF46-H1)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)

```
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctctg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag gaaaggcact tgagtggttg ggttttatta gaaacaaagc taatggttac     240
acaacagagt acagtgcatc tgtgaagggt cggttcacca tctccagaga taattcccaa     300
agcatcctct atcttcaaat ggacaccctg agagctgagg acagtgccac ttattactgt     360
gcaagagata ctggtttgc ttactggggc caagggactc tggtcactgt ctctgcagct     420
agcaccaagg gcccatcggt cttccccctg gcaccctcct ccaagagcac ctctggggc     480 acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttccccc aaaacccaag gacaccctca tgatctcccg gaccctgag      840 gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagcccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416

<210> SEQ ID NO 77
<211> LENGTH: 759
<212> TYPE: DNA
<213> ORGANISM: Artificial Sequence
<220> FEATURE:
<223> OTHER INFORMATION: Synthetic nucleotide sequence of light chain of
      anti-c-Met antibody (AbF46 or huAbF46-H1)
<220> FEATURE:
<221> NAME/KEY: misc_difference
<222> LOCATION: (1)..(6)
```

```
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77
gaattcacta gtgattaatt cgccgccacc atggattcac aggcccaggt cctcatgttg      60
ctgctgctat cggtatctgg tacctgtgga gacattttga tgacccagtc tccatcctcc    120
ctgactgtgt cagcaggaga aaggtcact atgagctgca agtccagtca gagtctttta     180
gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                          759

<210> SEQ ID NO 78
<211> LENGTH: 4170
<212> TYPE: DNA
<213> ORGANISM: Artificial Sequence
<220> FEATURE:
<223> OTHER INFORMATION: Synthetic polynucleotide encoding c-Met protein

<400> SEQUENCE: 78
atgaaggccc ccgctgtgct tgcacctggc atcctcgtgc tcctgtttac cttggtgcag     60
aggagcaatg gggagtgtaa agaggcacta gcaaagtccg agatgaatgt gaatatgaag    120
tatcagcttc ccaacttcac cgcggaaaca cccatccaga atgtcattct acatgagcat    180
cacattttcc ttggtgccac taactacatt tatgttttaa atgaggaaga ccttcagaag    240
gttgctgagt acaagactgg gcctgtgctg gaacacccag attgtttccc atgtcaggac    300
tgcagcagca agccaatttt atcaggaggt gtttggaaag ataacatcaa catggctcta    360
gttgtcgaca cctactatga tgatcaactc attagctgtg gcagcgtcaa cagagggacc    420
tgccagcgac atgtctttcc ccacaatcat actgctgaca tacagtcgga ggttcactgc    480
```

```
atattctccc cacagataga agagcccagc cagtgtcctg actgtgtggt gagcgccctg      540
ggagccaaag tcctttcatc tgtaaaggac cggttcatca acttctttgt aggcaatacc      600
ataaattctt cttatttccc agatcatcca ttgcattcga tatcagtgag aaggctaaag      660
gaaacgaaag atggttttat gttttgacg accagtcct acattgatgt tttacctgag        720
ttcagagatt cttaccccat taagtatgtc catgcctttg aaagcaacaa ttttatttac      780
ttcttgacgg tccaagggaa aactctagat gctcagactt tcacacaag aataatcagg       840 ttctgttcca taaactctgg attgcattcc tacatggaaa tgcctctgga gtgtattctc      900
acagaaaaga gaaaaagag atccacaaag aaggaagtgt ttaatatact tcaggctgcg       960
tatgtcagca agcctggggc ccagcttgct agacaaatag gagccagcct gaatgatgac     1020
attcttttcg gggtgttcgc acaaagcaag ccagattctg ccgaaccaat ggatcgatct     1080
gccatgtgtg cattccctat caaatatgtc aacgacttct caacaagat cgtcaacaaa      1140 aacaatgtga gatgtctcca gcatttttac ggacccaatc atgagcactg ctttaatagg     1200
acacttctga gaaattcatc aggctgtgaa gcgcgccgtg atgaatatcg aacagagttt     1260
accacagctt tgcagcgcgt tgacttattc atgggtcaat tcagcgaagt cctcttaaca     1320
tctatatcca ccttcattaa aggagacctc accatagcta atcttgggac atcagagggt     1380
cgcttcatgc aggttgtggt ttctcgatca ggaccatcaa cccctcatgt gaattttctc     1440
ctggactccc atccagtgtc tccagaagtg attgtggagc atacattaaa ccaaaatggc     1500
tacacactgg ttatcactgg gaagaagatc acgaagatcc cattgaatgg cttgggctgc     1560
agacatttcc agtcctgcag tcaatgcctc tctgccccac cctttgttca gtgtggctgg     1620
tgccacgaca aatgtgtgcg atcggaggaa tgcctgagcg ggacatggac tcaacagatc     1680
tgtctgcctg caatctacaa ggttttccca aatagtgcac cccttgaagg agggacaagg     1740
ctgaccatat gtggctggga ctttggattt cggaggaata taaatttga tttaaagaaa       1800 actagagttc tccttggaaa tgagagctgc accttgactt aagtgagag cacgatgaat      1860 acattgaaat gcacagttgg tcctgccatg aataagcatt tcaatatgtc cataattatt     1920
tcaaatggcc acgggacaac acaatacagt acattctcct atgtggatcc tgtaataaca     1980
agtatttcgc cgaaatacgg tcctatggct ggtggcactt tacttacttt aactggaaat     2040
tacctaaaca gtgggaattc tagacacatt tcaattggtg gaaaaacatg tactttaaaa     2100
agtgtgtcaa acagtattct tgaatgttat accccagccc aaaccatttc aactgagttt     2160
gctgttaaat tgaaaattga cttagccaac cgagagacaa gcatcttcag ttaccgtgaa     2220
gatcccattg tctatgaaat tcatccaacc aaatcttta ttagtggtgg gagcacaata      2280
acaggtgttg ggaaaaacct gaattcagtt agtgtcccga aatggtcat aaatgtgcat      2340 gaagcaggaa ggaactttac agtggcatgt caacatcgct ctaattcaga gataatctgt     2400
tgtaccactc cttccctgca acagctgaat ctgcaactcc ccctgaaaac caaagccttt     2460
ttcatgttag atgggatcct ttccaaatac tttgatctca tttatgtaca taatcctgtg     2520
tttaagcctt ttgaaaagcc agtgatgatc tcaatgggca tgaaaatgt actggaaatt      2580 aagggaaatg atattgaccc tgaagcagtt aaaggtgaag tgttaaaagt tggaaataag     2640
agctgtgaga atatacactt acattctgaa gccgttttat gcacggtccc caatgacctg     2700
ctgaaattga acagcgagct aaatatagag tggaagcaag caatttcttc aaccgtcctt     2760
ggaaaagtaa tagttcaacc agatcagaat ttcacaggat tgattgctgg tgttgtctca     2820
```

```
atatcaacag cactgttatt actacttggg tttttcctgt ggctgaaaaa gagaaagcaa    2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttggacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga aatgagactc ataatccaac tgtaaaagat    3540
cttattggct ttggtcttca agtagccaaa ggcatgaaat atcttgcaag caaaaagttt    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacaccttt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctacttatgt gaacgtaaaa    4080
tgtgtcgctc cgtatccttc tctgttgtca tcagaagata cgctgatga tgaggtggac    4140 acacgaccag cctccttctg ggagacatca                                    4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic SEMA domain of c-Met

<400> SEQUENCE: 79

```
Leu His Glu His His Ile Phe Leu Gly Ala Thr Asn Tyr Ile Tyr Val
 1               5                  10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125
```

Leu Ser Ser Val Lys Asp Arg Phe Ile Asn Phe Val Gly Asn Thr
130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
                180                 185                 190

Tyr Val His Ala Phe Glu Ser Asn Asn Phe Ile Tyr Phe Leu Thr Val
                195                 200                 205

Gln Arg Glu Thr Leu Asp Ala Gln Thr Phe His Thr Arg Ile Ile Arg
210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Arg Ser Thr Lys Lys Glu
                245                 250                 255

Val Phe Asn Ile Leu Gln Ala Ala Tyr Val Ser Lys Pro Gly Ala Gln
                260                 265                 270

Leu Ala Arg Gln Ile Gly Ala Ser Leu Asn Asp Ile Leu Phe Gly
                275                 280                 285

Val Phe Ala Gln Ser Lys Pro Asp Ser Ala Glu Pro Met Asp Arg Ser
290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
                340                 345                 350

Cys Glu Ala Arg Arg Asp Glu Tyr Arg Thr Glu Phe Thr Thr Ala Leu
                355                 360                 365

Gln Arg Val Asp Leu Phe Met Gly Gln Phe Ser Glu Val Leu Leu Thr
                370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Val Ser Arg Ser Gly Pro
                405                 410                 415

Ser Thr Pro His Val Asn Phe Leu Leu Asp Ser His Pro Val Ser Pro
                420                 425                 430

Glu Val Ile Val Glu His Thr Leu Asn Gln Asn Gly
                435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic PSI-IPT domain of c-Met

<400> SEQUENCE: 80

Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
                20                  25                  30

Pro Pro Phe Val Gln Cys Gly Trp Cys His Asp Lys Cys Val Arg Ser
                35                  40                  45

```
Glu Glu Cys Leu Ser Gly Thr Trp Thr Gln Gln Ile Cys Leu Pro Ala
 50                  55                  60

Ile Tyr Lys Val Phe Pro Asn Ser Ala Pro Leu Glu Gly Gly Thr Arg
 65                  70                  75                  80

Leu Thr Ile Cys Gly Trp Asp Phe Gly Phe Arg Arg Asn Asn Lys Phe
                 85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ser Asn Gly His
    130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
    210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
    290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
        355                 360                 365

Ser Met Gly Asn Glu Asn Val Leu Glu Ile Lys Gly Asn Asp Ile Asp
    370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
            420                 425                 430

Ile Ser Ser Thr Val Leu Gly Lys Val Ile Val Gln Pro Asp Gln Asn
        435                 440                 445

Phe Thr Gly
    450
```

```
<210> SEQ ID NO 81
<211> LENGTH: 313
<212> TYPE: PRT
<213> ORGANISM: Artificial Sequence
<220> FEATURE:
<223> OTHER INFORMATION: Synthetic TyrKc domain of c-Met

<400> SEQUENCE: 81

Val His Phe Asn Glu Val Ile Gly Arg Gly His Phe Gly Cys Val Tyr
  1               5                  10                  15

His Gly Thr Leu Leu Asp Asn Asp Gly Lys Lys Ile His Cys Ala Val
             20                  25                  30

Lys Ser Leu Asn Arg Ile Thr Asp Ile Gly Glu Val Ser Gln Phe Leu
         35                  40                  45

Thr Glu Gly Ile Ile Met Lys Asp Phe Ser His Pro Asn Val Leu Ser
     50                  55                  60

Leu Leu Gly Ile Cys Leu Arg Ser Glu Gly Ser Pro Leu Val Val Leu
 65                  70                  75                  80

Pro Tyr Met Lys His Gly Asp Leu Arg Asn Phe Ile Arg Asn Glu Thr
                 85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
    130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310

<210> SEQ ID NO 82
<211> LENGTH: 1332
<212> TYPE: DNA
<213> ORGANISM: Artificial Sequence
<220> FEATURE:
<223> OTHER INFORMATION: Synthetic polynucleotide encoding SEMA domain
      of c-Met
```

```
<400> SEQUENCE: 82
ctacatgagc atcacatttt ccttggtgcc actaactaca tttatgtttt aaatgaggaa      60
gaccttcaga aggttgctga gtacaagact gggcctgtgc tggaacaccc agattgtttc     120
ccatgtcagg actgcagcag caaagccaat ttatcaggag gtgtttggaa agataacatc     180
aacatggctc tagttgtcga cacctactat gatgatcaac tcattagctg tggcagcgtc     240
aacagaggga cctgccagcg acatgtcttt ccccacaatc atactgctga catacagtcg     300
gaggttcact gcatattctc cccacagata gaagagccca gccagtgtcc tgactgtgtg     360
gtgagcgccc tgggagccaa agtcctttca tctgtaaagg accggttcat caacttcttt     420
gtaggcaata ccataaattc ttcttatttc ccagatcatc cattgcattc gatatcagtg     480
agaaggctaa aggaaacgaa agatggtttt atgttttga cggaccagtc ctacattgat      540
gttttacctg agttcagaga ttcttacccc attaagtatg tccatgcctt tgaaagcaac     600
aattttattt acttcttgac ggtccaaagg gaaactctag atgctcagac ttttcacaca     660
agaataatca ggttctgttc cataaactct ggattgcatt cctacatgga aatgcctctg     720
gagtgtattc tcacagaaaa gagaaaaaag agatccacaa agaaggaagt gtttaatata     780
cttcaggctg cgtatgtcag caagcctggg gcccagcttg ctagacaaat aggagccagc     840
ctgaatgatg acattctttt cggggtgttc gcacaaagca agccagattc tgccgaacca     900
atggatcgat ctgccatgtg tgcattccct atcaaatatg tcaacgactt cttcaacaag     960
atcgtcaaca aaacaatgt gagatgtctc cagcattttt acggacccaa tcatgagcac    1020
tgctttaata ggacacttct gagaaattca tcaggctgtg aagcgcgccg tgatgaatat    1080
cgaacagagt ttaccacagc tttgcagcgc gttgacttat tcatgggtca attcagcgaa    1140
gtcctcttaa catctatatc caccttcatt aaaggagacc tcaccatagc taatcttggg    1200
acatcagagg gtcgcttcat gcaggttgtg gtttctcgat caggaccatc aaccccctcat    1260 gtgaattttc tcctggactc ccatccagtg tctccagaag tgattgtgga gcatacatta    1320
aaccaaaatg gc                                                        1332
```

<210> SEQ ID NO 83
<211> LENGTH: 1299
<212> TYPE: DNA
<213> ORGANISM: Artificial Sequence
<220> FEATURE:
<223> OTHER INFORMATION: Synthetic polynucleotide encoding PSI-IPT
       domain of c-Met

```
<400> SEQUENCE: 83
tacacactgg ttatcactgg gaagaagatc acgaagatcc cattgaatgg cttgggctgc      60
agacatttcc agtcctgcag tcaatgcctc tctgccccac cctttgttca gtgtggctgg     120
tgccacgaca atgtgtgcg atcggaggaa tgcctgagcg ggacatggac tcaacagatc     180
tgtctgcctg caatctacaa ggttttccca aatagtgcac cccttgaagg agggacaagg     240
ctgaccatat gtggctggga ctttggattt cggaggaata taaatttga tttaaagaaa      300 actagagttc tccttggaaa tgagagctgc accttgactt aagtgagag cacgatgaat      360 acattgaaat gcacagttgg tcctgccatg aataagcatt caatatgtc cataattatt      420 tcaaatggcc acgggacaac acaatacagt acattctcct atgtggatcc tgtaataaca     480
agtatttcgc cgaaatacgg tcctatggct ggtggcactt tacttacttt aactggaaat     540
tacctaaaca gtgggaattc tagacacatt tcaattggtg gaaaaacatg tacttttaaaa    600
```

```
agtgtgtcaa acagtattct tgaatgttat accccagccc aaaccatttc aactgagttt      660
gctgttaaat tgaaaattga cttagccaac cgagagacaa gcatcttcag ttaccgtgaa      720
gatcccattg tctatgaaat tcatccaacc aaatcttta ttagtggtgg gagcacaata       780
acaggtgttg ggaaaaacct gaattcagtt agtgtcccga gaatggtcat aaatgtgcat      840
gaagcaggaa ggaactttac agtggcatgt caacatcgct ctaattcaga gataatctgt     900
tgtaccactc cttccctgca acagctgaat ctgcaactcc ccctgaaaac caaagccttt     960
ttcatgttag atgggatcct ttccaaatac tttgatctca tttatgtaca taatcctgtg    1020
tttaagcctt tgaaaagcc agtgatgatc tcaatgggca atgaaaatgt actggaaatt     1080
aagggaaatg atattgaccc tgaagcagtt aaaggtgaag tgttaaaagt tggaaataag    1140
agctgtgaga atatacactt acattctgaa gccgttttat gcacggtccc caatgacctg    1200
ctgaaattga acagcgagct aaatatagag tggaagcaag caatttcttc aaccgtcctt    1260
ggaaaagtaa tagttcaacc agatcagaat ttcacagga                          1299
```

<210> SEQ ID NO 84
<211> LENGTH: 939
<212> TYPE: DNA
<213> ORGANISM: Artificial Sequence
<220> FEATURE:
<223> OTHER INFORMATION: Synthetic polynucleotide encoding TyrKc domain of c-Met

<400> SEQUENCE: 84

```
gtgcatttca atgaagtcat aggaagaggg cattttggtt gtgtatatca tgggactttg      60
ttggacaatg atggcaagaa aattcactgt gctgtgaaat ccttgaacag aatcactgac     120
ataggagaag tttcccaatt tctgaccgag ggaatcatca tgaaagattt tagtcatccc     180
aatgtcctct cgctcctggg aatctgcctg cgaagtgaag ggtctccgct ggtggtccta    240
ccatacatga acatggaga tcttcgaaat tcattcgaa atgagactca taatccaact     300
gtaaaagatc ttattggctt tggtcttcaa gtagccaaag gcatgaaata tcttgcaagc    360
aaaaagtttg tccacagaga cttggctgca agaaactgta tgctggatga aaaattcaca    420
gtcaaggttg ctgattttgg tcttgccaga gacatgtatg ataaagaata ctatagtgta    480
cacaacaaaa caggtgcaaa gctgccagtg aagtggatgg cttttggaaag tctgcaaact    540 caaaagttta ccaccaagtc agatgtgtgg tcctttggcg tgctcctctg ggagctgatg    600
acaagaggag cccccacctta tcctgacgta aacaccttg atataactgt ttacttgttg    660
caagggagaa gactcctaca acccgaatac tgcccagacc ccttatatga agtaatgcta    720
aaatgctggc accctaaagc cgaaatgcgc ccatcctttt ctgaactggt gtcccggata    780
tcagcgatct tctctacttt cattgggag cactatgtcc atgtgaacgc tacttatgtg    840
aacgtaaaat gtgtcgctcc gtatccttct ctgttgtcat cagaagataa cgctgatgat    900
gaggtggaca cacgaccagc ctccttctgg gagacatca                          939
```

<210> SEQ ID NO 85
<211> LENGTH: 13
<212> TYPE: PRT
<213> ORGANISM: Artificial Sequence
<220> FEATURE:
<223> OTHER INFORMATION: Synthetic heavy chain CDR3 of anti-c-Met antibody

<400> SEQUENCE: 85

Asp Asn Trp Phe Ala Tyr Trp Gly Gln Gly Thr Leu Val

<210> SEQ ID NO 86
<211> LENGTH: 10
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 86

Leu Thr Phe Gly Ala Gly Thr Lys Leu Glu
1               5                   10

<210> SEQ ID NO 87
<211> LENGTH: 117
<212> TYPE: PRT
<213> ORGANISM: Artificial Sequence
<220> FEATURE:
<223> OTHER INFORMATION: Synthetic heavy chain variable region of
      monoclonal antibody AbF46

<400> SEQUENCE: 87

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody

<400> SEQUENCE: 88

Asp Ile Leu Met Thr Gln Ser Pro Ser Ser Leu Thr Val Ser Ala Gly
1               5                   10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 89

Gln Gln Ser Tyr Ser Ala Pro Leu Thr Phe Gly Ala Gly Thr Lys Leu
  1               5                  10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic heavy chain variable region of AT-VH1

<400> SEQUENCE: 90

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Ser Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic heavy chain variable region of AT-VH2

<400> SEQUENCE: 91

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr

```
                65                  70                  75                  80
Leu Tyr Leu Gln Met Asn Ser Leu Arg Ala Glu Asp Thr Ala Thr Tyr
                    85                  90                  95

Tyr Cys Ala Arg Asp Asn Trp Phe Ala Tyr Trp Gly Gln Gly Thr Leu
            100                 105                 110

Val Thr Val Ser Ser
            115

<210> SEQ ID NO 92
<211> LENGTH: 117
<212> TYPE: PRT
<213> ORGANISM: Artificial Sequence
<220> FEATURE:
<223> OTHER INFORMATION: Synthetic heavy chain variable region of AT-VH3

<400> SEQUENCE: 92

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                    85                  90                  95

Tyr Cys Ala Arg Asp Asn Trp Phe Ala Tyr Trp Gly Gln Gly Thr Leu
            100                 105                 110

Val Thr Val Ser Ser
            115

<210> SEQ ID NO 93
<211> LENGTH: 117
<212> TYPE: PRT
<213> ORGANISM: Artificial Sequence
<220> FEATURE:
<223> OTHER INFORMATION: Synthetic heavy chain variable region of AT-VH4

<400> SEQUENCE: 93

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                    85                  90                  95

Tyr Cys Ala Arg Asp Asn Trp Phe Ala Tyr Trp Gly Gln Gly Thr Leu
            100                 105                 110

Val Thr Val Ser Ser
            115
```

```
<210> SEQ ID NO 94
<211> LENGTH: 117
<212> TYPE: PRT
<213> ORGANISM: Artificial Sequence
<220> FEATURE:
<223> OTHER INFORMATION: Synthetic heavy chain variable region of AT-VH5

<400> SEQUENCE: 94

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 95
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 95

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic light chain variable region of AT-Vk1

<400> SEQUENCE: 96

Asp Ile Leu Met Thr Gln Ser Pro Ser Ser Leu Thr Ala Ser Val Gly
```

```
                  1               5                  10                 15
Asp Arg Val Thr Met Thr Cys Lys Ser Ser Gln Ser Leu Leu Ala Ser
                    20                  25                  30

Gly Asn Gln Asn Asn Tyr Leu Ala Trp His Gln Gln Lys Pro Gly Lys
                    35                  40                  45

Ala Pro Lys Met Leu Ile Ile Trp Ala Ser Thr Arg Val Ser Gly Val
 50                      55                  60

Pro Asp Arg Phe Ile Gly Ser Gly Ser Gly Thr Asp Phe Thr Leu Thr
 65                      70                  75                  80

Ile Ser Ser Leu Gln Ala Glu Asp Val Ala Val Tyr Tyr Cys Gln Gln
                    85                  90                  95

Ser Tyr Ser Ala Pro Leu Thr Phe Gly Gln Gly Thr Lys Leu Glu Ile
                   100                 105                 110

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic light chain variable region of AT-Vk2

<400> SEQUENCE: 97

Asp Ile Leu Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                    20                  25                  30

Gly Asn Gln Asn Asn Tyr Leu Ala Trp His Gln Gln Lys Pro Gly Lys
                    35                  40                  45

Ala Pro Lys Met Leu Ile Ile Trp Ala Ser Thr Arg Val Ser Gly Val
 50                      55                  60

Pro Asp Arg Phe Ile Gly Ser Gly Ser Gly Thr Asp Phe Thr Leu Thr
 65                      70                  75                  80

Ile Ser Ser Leu Gln Ala Glu Asp Val Ala Val Tyr Tyr Cys Gln Gln
                    85                  90                  95

Ser Tyr Ser Ala Pro Leu Thr Phe Gly Gln Gly Thr Lys Leu Glu Ile
                   100                 105                 110

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic light chain variable region of AT-Vk3

<400> SEQUENCE: 98

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                    20                  25                  30

Gly Asn Gln Asn Asn Tyr Leu Ala Trp His Gln Gln Lys Pro Gly Lys
                    35                  40                  45

Ala Pro Lys Met Leu Ile Ile Trp Ala Ser Thr Arg Val Ser Gly Val
 50                      55                  60

Pro Asp Arg Phe Ile Gly Ser Gly Ser Gly Thr Asp Phe Thr Leu Thr
 65                      70                  75                  80
```

```
Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic light chain variable region of AT-Vk4

<400> SEQUENCE: 99

Asp Ile Gln Met Thr Gln Ser Pro Ser Ser Leu Ser Ala Ser Val Gly
 1               5                  10                  15

Asp Arg Val Thr Ile Thr Cys Lys Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic modified hinge region(U7-HC6)

<400> SEQUENCE: 100

Glu Pro Ser Cys Asp Lys His Cys Cys Pro Pro Cys Pro
 1               5                  10

<210> SEQ ID NO 101
<211> LENGTH: 13
<212> TYPE: PRT
<213> ORGANISM: Artificial Sequence
<220> FEATURE:
<223> OTHER INFORMATION: Synthetic modified hinge region(U6-HC7)

<400> SEQUENCE: 101

Glu Pro Lys Ser Cys Asp Cys His Cys Pro Pro Cys Pro
 1               5                  10

<210> SEQ ID NO 102
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 102

Glu Arg Lys Cys Cys Val Glu Cys Pro Pro Cys Pro
```

```
                               1               5                  10

<210> SEQ ID NO 103
<211> LENGTH: 14
<212> TYPE: PRT
<213> ORGANISM: Artificial Sequence
<220> FEATURE:
<223> OTHER INFORMATION: Synthetic modified hinge region(U6-HC8)

<400> SEQUENCE: 103

Glu Pro Arg Asp Cys Gly Cys Lys Pro Cys Pro Pro Cys Pro
 1               5                  10

<210> SEQ ID NO 104
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 104

Glu Lys Cys Asp Lys Thr His Thr Cys Pro Pro Cys Pro
 1               5                  10

<210> SEQ ID NO 105
<211> LENGTH: 15
<212> TYPE: PRT
<213> ORGANISM: Artificial Sequence
<220> FEATURE:
<223> OTHER INFORMATION: Synthetic human hinge region

<400> SEQUENCE: 105

Glu Pro Lys Ser Cys Asp Lys Thr His Thr Cys Pro Pro Cys Pro
 1               5                  10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y

<400> SEQUENCE: 106

Lys Ser Ser Gln Ser Leu Leu Ala Trp Gly Asn Gln Asn Asn Tyr Leu
 1               5                  10                  15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic amino acid sequence of light chain
      variable region of antibody L3-11Y

<400> SEQUENCE: 107

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Trp
                20                  25                  30

Gly Asn Gln Asn Asn Tyr Leu Ala Trp Tyr Gln Gln Lys Pro Gly Lys
            35                  40                  45

Ala Pro Lys Met Leu Ile Ile Trp Ala Ser Thr Arg Val Ser Gly Val
        50                  55                  60
```

```
Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic amino acid sequence of light chain of
      antibody L3-11Y

<400> SEQUENCE: 108

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Trp
                 20                  25                  30

Gly Asn Gln Asn Asn Tyr Leu Ala Trp Tyr Gln Gln Lys Pro Gly Lys
             35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 109
<211> LENGTH: 5
<212> TYPE: PRT
<213> ORGANISM: Artificial Sequence
<220> FEATURE:
<223> OTHER INFORMATION: Synthetic Polynucleotide used for CDR-H1 of
      anti-HER2 antibody

<400> SEQUENCE: 109

Ser Tyr Trp Ile Gly
 1               5
```

```
<210> SEQ ID NO 110
<211> LENGTH: 5
<212> TYPE: PRT
<213> ORGANISM: Artificial Sequence
<220> FEATURE:
<223> OTHER INFORMATION: Synthetic Polynucleotide used for CDR-H1 of
      anti-HER2 antibody

<400> SEQUENCE: 110

Asp Tyr Ala Met Ser
1               5

<210> SEQ ID NO 111
<211> LENGTH: 5
<212> TYPE: PRT
<213> ORGANISM: Artificial Sequence
<220> FEATURE:
<223> OTHER INFORMATION: Synthetic Polynucleotide used for CDR-H1 of
      anti-HER2 antibody

<400> SEQUENCE: 111

Ser Tyr Ala Ile Ser
1               5

<210> SEQ ID NO 112
<211> LENGTH: 17
<212> TYPE: PRT
<213> ORGANISM: Artificial Sequence
<220> FEATURE:
<223> OTHER INFORMATION: Synthetic Polynucleotide used for CDR-H2 of
      anti-HER2 antibody

<400> SEQUENCE: 112

Ile Ile Tyr Pro Gly Asp Ser Asp Thr Arg Tyr Ser Pro Ser Phe Gln
1               5                  10                  15

Gly

<210> SEQ ID NO 113
<211> LENGTH: 19
<212> TYPE: PRT
<213> ORGANISM: Artificial Sequence
<220> FEATURE:
<223> OTHER INFORMATION: Synthetic Polynucleotide used for CDR-H2 of
      anti-HER2 antibody

<400> SEQUENCE: 113

Phe Ile Arg Ser Lys Ala Tyr Gly Gly Thr Thr Glu Tyr Ala Ala Ser
1               5                  10                  15

Val Lys Gly

<210> SEQ ID NO 114
<211> LENGTH: 17
<212> TYPE: PRT
<213> ORGANISM: Artificial Sequence
<220> FEATURE:
<223> OTHER INFORMATION: Synthetic Polynucleotide used for CDR-H2 of
      anti-HER2 antibody

<400> SEQUENCE: 114

Gly Ile Ile Pro Ile Phe Gly Thr Ala Asn Tyr Ala Gln Lys Phe Gln
1               5                  10                  15

Gly

<210> SEQ ID NO 115
<211> LENGTH: 15
<212> TYPE: PRT
```

```
<213> ORGANISM: Artificial Sequence
<220> FEATURE:
<223> OTHER INFORMATION: Synthetic Polynucleotide used for CDR-H3 of
      anti-HER2 antibody

<400> SEQUENCE: 115

Arg His Tyr Tyr Asp Ser Ser Gly Tyr Ser Tyr Phe Pro Asp Tyr
 1               5                  10                  15

<210> SEQ ID NO 116
<211> LENGTH: 17
<212> TYPE: PRT
<213> ORGANISM: Artificial Sequence
<220> FEATURE:
<223> OTHER INFORMATION: Synthetic Polynucleotide used for CDR-H3 of
      anti-HER2 antibody

<400> SEQUENCE: 116

Arg Leu Ser Val Ala Ala Ala Gly Thr Gly Gly Tyr Asn Trp Phe Asp
 1               5                  10                  15

Pro

<210> SEQ ID NO 117
<211> LENGTH: 10
<212> TYPE: PRT
<213> ORGANISM: Artificial Sequence
<220> FEATURE:
<223> OTHER INFORMATION: Synthetic Polynucleotide used for CDR-H3 of
      anti-HER2 antibody

<400> SEQUENCE: 117

Arg Asp Leu Tyr Pro Ala Met Ala Glu Tyr
 1               5                  10

<210> SEQ ID NO 118
<211> LENGTH: 20
<212> TYPE: PRT
<213> ORGANISM: Artificial Sequence
<220> FEATURE:
<223> OTHER INFORMATION: Synthetic Polynucleotide used for CDR-H3 of
      anti-HER2 antibody

<400> SEQUENCE: 118

Arg Asp Ser Gly Tyr Ser Tyr Gly Tyr Pro Met Asn Tyr Tyr Tyr
 1               5                  10                  15

Tyr Met Asp Val
            20

<210> SEQ ID NO 119
<211> LENGTH: 15
<212> TYPE: PRT
<213> ORGANISM: Artificial Sequence
<220> FEATURE:
<223> OTHER INFORMATION: Synthetic Polynucleotide used for CDR-H3 of
      anti-HER2 antibody

<400> SEQUENCE: 119

Arg Leu Val Val Gly Ala Asn Pro Pro Thr Tyr Tyr Phe Asp Tyr
 1               5                  10                  15

<210> SEQ ID NO 120
<211> LENGTH: 14
<212> TYPE: PRT
<213> ORGANISM: Artificial Sequence
<220> FEATURE:
<223> OTHER INFORMATION: Synthetic Polynucleotide used for CDR-L1 of
      anti-HER2 antibody
```

<400> SEQUENCE: 120

Gly Leu Ser Ser Gly Ser Val Ser Thr Ser Tyr Tyr Pro Ser
 1               5                  10

<210> SEQ ID NO 121
<211> LENGTH: 14
<212> TYPE: PRT
<213> ORGANISM: Artificial Sequence
<220> FEATURE:
<223> OTHER INFORMATION: Synthetic Polynucleotide used for CDR-L1 of
      anti-HER2 antibody

<400> SEQUENCE: 121

Gly Leu Thr Ser Gly Ser Val Ser Thr Ser Tyr Tyr Pro Ser
 1               5                  10

<210> SEQ ID NO 122
<211> LENGTH: 13
<212> TYPE: PRT
<213> ORGANISM: Artificial Sequence
<220> FEATURE:
<223> OTHER INFORMATION: Synthetic Polynucleotide used for CDR-L1 of
      anti-HER2 antibody

<400> SEQUENCE: 122

Thr Arg Ser Ser Gly Ser Ile Asp Ser Asn Phe Val Gln
 1               5                  10

<210> SEQ ID NO 123
<211> LENGTH: 14
<212> TYPE: PRT
<213> ORGANISM: Artificial Sequence
<220> FEATURE:
<223> OTHER INFORMATION: Synthetic Polynucleotide used for CDR-L1 of
      anti-HER2 antibody

<400> SEQUENCE: 123

Gly Leu Ser Ser Gly Ser Val Ser Pro Thr Tyr Tyr Pro Ser
 1               5                  10

<210> SEQ ID NO 124
<211> LENGTH: 11
<212> TYPE: PRT
<213> ORGANISM: Artificial Sequence
<220> FEATURE:
<223> OTHER INFORMATION: Synthetic Polynucleotide used for CDR-L2 of
      anti-HER2 antibody

<400> SEQUENCE: 124

Ser Thr Asn Thr Arg Ser Ser Gly Val Pro Asp
 1               5                  10

<210> SEQ ID NO 125
<211> LENGTH: 11
<212> TYPE: PRT
<213> ORGANISM: Artificial Sequence
<220> FEATURE:
<223> OTHER INFORMATION: Synthetic Polynucleotide used for CDR-L2 of
      anti-HER2 antibody

<400> SEQUENCE: 125

Asp Asp Asn Gln Arg Pro Ser Gly Val Pro Asp
 1               5                  10

<210> SEQ ID NO 126
<211> LENGTH: 11

```
<212> TYPE: PRT
<213> ORGANISM: Artificial Sequence
<220> FEATURE:
<223> OTHER INFORMATION: Synthetic Polynucleotide used for CDR-L2 of
      anti-HER2 antibody

<400> SEQUENCE: 126

Arg Thr Asn Ile Arg Ser Ser Gly Val Pro Asp
  1               5                   10

<210> SEQ ID NO 127
<211> LENGTH: 10
<212> TYPE: PRT
<213> ORGANISM: Artificial Sequence
<220> FEATURE:
<223> OTHER INFORMATION: Synthetic Polynucleotide used for CDR-L3 of
      anti-HER2 antibody

<400> SEQUENCE: 127

Val Leu Tyr Met Gly Ser Gly Ile Trp Val
  1               5                   10

<210> SEQ ID NO 128
<211> LENGTH: 10
<212> TYPE: PRT
<213> ORGANISM: Artificial Sequence
<220> FEATURE:
<223> OTHER INFORMATION: Synthetic Polynucleotide used for CDR-L3 of
      anti-HER2 antibody

<400> SEQUENCE: 128

Met Leu Tyr Leu Gly Gly Gly Ile Ser Val
  1               5                   10

<210> SEQ ID NO 129
<211> LENGTH: 9
<212> TYPE: PRT
<213> ORGANISM: Artificial Sequence
<220> FEATURE:
<223> OTHER INFORMATION: Synthetic Polynucleotide used for CDR-L3 of
      anti-HER2 antibody

<400> SEQUENCE: 129

Gln Ser Tyr Asp Ser Asn Asn Gln Val
  1               5

<210> SEQ ID NO 130
<211> LENGTH: 10
<212> TYPE: PRT
<213> ORGANISM: Artificial Sequence
<220> FEATURE:
<223> OTHER INFORMATION: Synthetic Polynucleotide used for CDR-L3 of
      anti-HER2 antibody

<400> SEQUENCE: 130

Leu Leu Tyr Met Gly Ser Gly Val Ser Leu
  1               5                   10

<210> SEQ ID NO 131
<211> LENGTH: 10
<212> TYPE: PRT
<213> ORGANISM: Artificial Sequence
<220> FEATURE:
<223> OTHER INFORMATION: Synthetic Polynucleotide used for CDR-L3 of
      anti-HER2 antibody

<400> SEQUENCE: 131

Val Leu Tyr Met Gly Ser Gly Ile Ser Leu
```

-continued

```
         1               5                  10
```

<210> SEQ ID NO 132
<211> LENGTH: 123
<212> TYPE: PRT
<213> ORGANISM: Artificial Sequence
<220> FEATURE:
<223> OTHER INFORMATION: Synthetic Amino acid sequence of heavy chain
      variable region of anti-HER2 antibody 41-B11

<400> SEQUENCE: 132

```
Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Tyr Tyr Asp Ser Ser Gly Tyr Ser Tyr Phe Pro Asp Tyr
                100                 105                 110

Trp Gly Gln Gly Thr Leu Val Thr Val Ser Ser
            115                 120
```

<210> SEQ ID NO 133
<211> LENGTH: 125
<212> TYPE: PRT
<213> ORGANISM: Artificial Sequence
<220> FEATURE:
<223> OTHER INFORMATION: Synthetic Amino acid sequence of heavy chain
      variable region of anti-HER2 antibody 41-C6

<400> SEQUENCE: 133

```
Gln Ile Gln Leu Val Gln Ser Gly Ala Glu Val Lys Lys Pro Gly Glu
  1               5                  10                  15

Ser Leu Lys Ile Ser Cys Arg Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu Ser Val Ala Ala Ala Gly Thr Gly Tyr Asn Trp Phe
                100                 105                 110

Asp Pro Trp Gly Gln Gly Thr Leu Val Thr Val Ser Ser
            115                 120                 125
```

<210> SEQ ID NO 134
<211> LENGTH: 120
<212> TYPE: PRT
<213> ORGANISM: Artificial Sequence
<220> FEATURE:
<223> OTHER INFORMATION: Synthetic Amino acid sequence of heavy chain variable region of anti-HER2 antibody 41-E1

<400> SEQUENCE: 134

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Asp Leu Tyr Pro Ala Met Ala Glu Tyr Trp Gly Gln
            100                 105                 110

Gly Thr Leu Val Thr Val Ser Ser
        115                 120

<210> SEQ ID NO 135
<211> LENGTH: 128
<212> TYPE: PRT
<213> ORGANISM: Artificial Sequence
<220> FEATURE:
<223> OTHER INFORMATION: Synthetic Amino acid sequence of heavy chain
      variable region of anti-HER2 antibody 44-C12

<400> SEQUENCE: 135

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Gly Tyr Ser Tyr Gly Tyr Pro Met Asn Tyr Tyr Tyr
            100                 105                 110

Tyr Tyr Met Asp Val Trp Gly Lys Gly Thr Thr Val Thr Val Ser Ser
        115                 120                 125

<210> SEQ ID NO 136
<211> LENGTH: 123
<212> TYPE: PRT
<213> ORGANISM: Artificial Sequence
<220> FEATURE:
<223> OTHER INFORMATION: Synthetic Amino acid sequence of heavy chain
      variable region of anti-HER2 antibody 44-H4

<400> SEQUENCE: 136

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

```
Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu Val Val Gly Ala Asn Pro Pro Thr Tyr Tyr Phe Asp Tyr
                100                 105                 110

Trp Gly Gln Gly Thr Leu Val Thr Val Ser Ser
        115                 120
```

<210> SEQ ID NO 137
<211> LENGTH: 111
<212> TYPE: PRT
<213> ORGANISM: Artificial Sequence
<220> FEATURE:
<223> OTHER INFORMATION: Synthetic Amino acid sequence of light chain variable region of anti-HER2 antibody 41-B11

<400> SEQUENCE: 137

```
Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Ser Thr Ser
             20                  25                  30

Tyr Tyr Pro Ser Trp Tyr Gln Gln Thr Pro Gly Gln Ala Pro Arg Thr
         35                  40                  45

Leu Ile Tyr Ser Thr Asn Thr Arg Ser Ser Gly Val Pro Asp Arg Phe
     50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Val Leu Tyr Met Gly Ser
                 85                  90                  95

Gly Ile Trp Val Phe Gly Gly Gly Thr Lys Leu Thr Val Leu Gly
                100                 105                 110
```

<210> SEQ ID NO 138
<211> LENGTH: 111
<212> TYPE: PRT
<213> ORGANISM: Artificial Sequence
<220> FEATURE:
<223> OTHER INFORMATION: Synthetic Amino acid sequence of light chain variable region of anti-HER2 antibody 41-C6

<400> SEQUENCE: 138

```
Gln Thr Val Val Thr Gln Glu Pro Ser Ser Ser Val Ser Pro Gly Gly
 1               5                  10                  15

Thr Val Thr Leu Thr Cys Gly Leu Thr Ser Gly Ser Val Ser Thr Ser
             20                  25                  30

Tyr Tyr Pro Ser Trp Tyr Gln Gln Thr Pro Gly Gln Ala Pro Arg Thr
         35                  40                  45

Leu Ile Tyr Ser Thr Asn Thr Arg Ser Ser Gly Val Pro Asp Arg Phe
     50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Met Leu Tyr Leu Gly Gly
                 85                  90                  95
```

```
Gly Ile Ser Val Phe Gly Gly Gly Thr Lys Leu Thr Val Leu Gly
            100                 105                 110
```

<210> SEQ ID NO 139
<211> LENGTH: 111
<212> TYPE: PRT
<213> ORGANISM: Artificial Sequence
<220> FEATURE:
<223> OTHER INFORMATION: Synthetic Amino acid sequence of light chain
      variable region of anti-HER2 antibody 41-E1

<400> SEQUENCE: 139

```
Gln Pro Val Leu Thr Gln Pro His Ser Val Ser Glu Ser Pro Gly Lys
 1               5                  10                  15

Thr Val Thr Ile Ser Cys Thr Arg Ser Ser Gly Ser Ile Asp Ser Asn
            20                  25                  30

Phe Val Gln Trp Tyr Gln Gln Arg Pro Gly Ser Ser Pro Thr Thr Val
        35                  40                  45

Ile Tyr Asp Asp Asn Gln Arg Pro Ser Gly Val Pro Asp Arg Phe Ser
50                  55                  60

Gly Ser Ile Asp Ser Ser Ser Asn Ser Ala Ser Leu Thr Ile Ser Gly
65                  70                  75                  80

Leu Lys Ile Glu Asp Glu Ala Asp Tyr Tyr Cys Gln Ser Tyr Asp Ser
                85                  90                  95

Asn Asn Gln Val Phe Gly Gly Gly Thr Lys Leu Thr Val Leu Arg
            100                 105                 110
```

<210> SEQ ID NO 140
<211> LENGTH: 111
<212> TYPE: PRT
<213> ORGANISM: Artificial Sequence
<220> FEATURE:
<223> OTHER INFORMATION: Synthetic Amino acid sequence of light chain
      variable region of anti-HER2 antibody 44-C12

<400> SEQUENCE: 140

```
Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Ser Pro Thr
            20                  25                  30

Tyr Tyr Pro Ser Trp Tyr Gln Gln Thr Pro Gly Gln Ala Pro Arg Thr
        35                  40                  45

Leu Ile Tyr Arg Thr Asn Ile Arg Ser Ser Gly Val Pro Asp Arg Phe
50                  55                  60

Ser Gly Ser Ile Leu Gly Asn Lys Ala Ala Leu Thr Ile Thr Gly Ala
65                  70                  75                  80

Gln Ala Asp Asp Glu Ser Leu Tyr Tyr Cys Leu Leu Tyr Met Gly Ser
                85                  90                  95

Gly Val Ser Leu Phe Gly Gly Gly Thr Lys Leu Thr Val Leu Arg
            100                 105                 110
```

<210> SEQ ID NO 141
<211> LENGTH: 111
<212> TYPE: PRT
<213> ORGANISM: Artificial Sequence
<220> FEATURE:
<223> OTHER INFORMATION: Synthetic Amino acid sequence of light chain
      variable region of anti-HER2 antibody 44-H4

<400> SEQUENCE: 141

```
Gln Ala Val Val Thr Gln Glu Pro Ser Phe Ser Val Ser Pro Gly Gly
  1               5                  10                 15

Thr Val Thr Leu Thr Cys Gly Leu Ser Ser Gly Ser Val Ser Thr Ser
             20                  25                 30

Tyr Tyr Pro Ser Trp Tyr Gln Gln Thr Pro Gly Gln Ala Pro Arg Thr
         35                  40                  45

Leu Ile Tyr Ser Thr Asn Thr Arg Ser Ser Gly Val Pro Asp Arg Phe
 50                  55                  60

Ser Gly Ser Ile Leu Gly Asn Lys Ala Ala Leu Thr Ile Thr Gly Ala
 65                  70                  75                  80

Gln Thr Asp Asp Glu Ser Asp Tyr Tyr Cys Val Leu Tyr Met Gly Ser
                 85                  90                  95

Gly Ile Ser Leu Phe Gly Gly Gly Thr Lys Val Thr Val Leu Gly
            100                 105                 110

<210> SEQ ID NO 142
<211> LENGTH: 369
<212> TYPE: DNA
<213> ORGANISM: Artificial Sequence
<220> FEATURE:
<223> OTHER INFORMATION: Synthetic Nucleotide sequence of heavy chain
      variable region of anti-HER2 antibody 41-B11

<400> SEQUENCE: 142
gaggtgcagc tggtgcagtc tggagcagag gtgaaaaagc ccggggagtc tctgaagatc     60
tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcagc accgcctac    240 ctgcagtgga gcagcctgaa ggcctcggac accgccatgt attactgtgc gagacattac    300
tatgatagta gtggttattc ctactttccg gactactggg gccagggaac cctggtcacc    360
gtctcctca                                                            369

<210> SEQ ID NO 143
<211> LENGTH: 375
<212> TYPE: DNA
<213> ORGANISM: Artificial Sequence
<220> FEATURE:
<223> OTHER INFORMATION: Synthetic Nucleotide sequence of heavy chain
      variable region of anti-HER2 antibody 41-C6

<400> SEQUENCE: 143
cagatccagc tggtacaatc tggagcagag gtgaaaaagc ccggggagtc tctgaagatc     60
tcctgtaggg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcagc accgcctac    240 ctgcagtgga gcagcctgaa ggcctcggac accgccatgt attactgtgc gagactcagc    300
gtagcagcag ctggtacggg ggggtacaac tggttcgacc cctggggcca gggaaccctg    360
gtcaccgtct cctca                                                     375

<210> SEQ ID NO 144
<211> LENGTH: 360
<212> TYPE: DNA
<213> ORGANISM: Artificial Sequence
<220> FEATURE:
<223> OTHER INFORMATION: Synthetic Nucleotide sequence of heavy chain
      variable region of anti-HER2 antibody 41-E1
```

<400> SEQUENCE: 144

```
gaggtgcagc tggtggagtc tgggggaggc ttggtaaagc cagggcggtc cctgagactc    60
tcctgtacag cttctggatt cacctttggt gattatgcta tgagctggtt ccgccaggct   120
ccagggaagg ggctggagtg ggtaggtttc attagaagca aagcttatgg tgggacaaca   180
gaatacgccg cgtctgtgaa aggcagattc accatctcaa gagatgattc aaaagcatc   240
gcctatctgc aaatgaacag cctgaaaacc gaggacacac cgtgtatta ctgtactaga   300
gatttatacc cagctatggc tgagtactgg ggccagggaa ccctggtcac cgtctcctca   360
```

<210> SEQ ID NO 145
<211> LENGTH: 384
<212> TYPE: DNA
<213> ORGANISM: Artificial Sequence
<220> FEATURE:
<223> OTHER INFORMATION: Synthetic Nucleotide sequence of heavy chain
      variable region of anti-HER2 antibody 44-C12

<400> SEQUENCE: 145

```
gaagtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag ggcttgagtg gatgggaggg atcatcccta tctttggtac agcaaactac   180
gcacagaagt tccagggcag agtcacgatt accgcggaca aatccacgag cacagcctac   240
atggagctga gcagcctgag atctgaggac acggccgtgt attactgtgc gagagattcg   300
ggatacagct atggttaccc tatgaattac tactactact acatggacgt ctggggcaaa   360
gggaccacgg tcaccgtctc ctca                                          384
```

<210> SEQ ID NO 146
<211> LENGTH: 369
<212> TYPE: DNA
<213> ORGANISM: Artificial Sequence
<220> FEATURE:
<223> OTHER INFORMATION: Synthetic Nucleotide sequence of heavy chain
      variable region of anti-HER2 antibody 44-H4

<400> SEQUENCE: 146

```
gaggtgcagc tggtgcagtc tggagcagag gtgaaaaagc ccggggagtc tctgaagatc    60
tcctgtaagg gttctggata cagctttacc agctactgga tcggctgggt gcgccagatg   120
cccgggaaag gcctggagtg gatggggatc atctatcctg gtgactctga taccagatac   180
agcccgtcct tccaaggcca ggtcaccatc tcagccgaca agtccatcag caccgcctac   240
ctgcagtgga gcagcctgaa ggcctcggac accgccatgt attactgtgc gagactcgta   300
gtgggagcta accccccaac gtactacttt gactactggg gccagggaac cctggtcacc   360
gtctcctca                                                           369
```

<210> SEQ ID NO 147
<211> LENGTH: 333
<212> TYPE: DNA
<213> ORGANISM: Artificial Sequence
<220> FEATURE:
<223> OTHER INFORMATION: Synthetic Nucleotide sequence of light chain
      variable region of anti-HER2 antibody 41-B11

<400> SEQUENCE: 147

```
cagactgtgg tgacccagga gccatcgttc tcagtgtccc ctggagggac agtcacactc    60
acttgtggct tgagctctgg ctcagtctct actagttact accccagctg gtaccagcag   120
```

```
acccaggcc aggctccacg cacgctcatc tacagcacaa acactcgctc ttctggggtc    180
cctgatcgct tctctggctc catccttggg aacaaagctg ccctcaccat cacggggcc    240 caggcagatg atgaatctga ttattactgt gtgctgtata tgggtagtgg catttgggtg    300
ttcggcggag ggaccaagtt gaccgtccta ggt                                333

<210> SEQ ID NO 148
<211> LENGTH: 333
<212> TYPE: DNA
<213> ORGANISM: Artificial Sequence
<220> FEATURE:
<223> OTHER INFORMATION: Synthetic Nucleotide sequence of light chain
      variable region of anti-HER2 antibody 41-C6

<400> SEQUENCE: 148
cagactgtgg tgacccagga gccatcgtcc tcagtgtccc ctggagggac agtcacactc    60
acttgtggct tgacctctgg ctcagtctct actagttact accccagctg gtaccagcag    120
accccaggcc aggctccacg cacgctcatc tacagcacaa acactcgctc ttctggggtc    180
cctgatcgct tctctggctc catccttggg aacaaagctg ccctcaccat cacggggcc    240 caggcagatg atgaatctga ttattactgt atgctatatt tgggtggtgg catttcggta    300
ttcggcggag ggaccaagct gaccgtccta ggt                                333

<210> SEQ ID NO 149
<211> LENGTH: 333
<212> TYPE: DNA
<213> ORGANISM: Artificial Sequence
<220> FEATURE:
<223> OTHER INFORMATION: Synthetic Nucleotide sequence of light chain
      variable region of anti-HER2 antibody 41-E1

<400> SEQUENCE: 149
cagcctgtgc tgactcagcc ccactctgtg tcggagtctc cggggaagac ggtcaccatc    60
tcctgcaccc gcagcagtgg cagcattgac agcaactttg tgcagtggta ccagcagcgc    120
ccgggcagtt cccccaccac tgtcatctat gacgataacc agaggccctc tggggtccct    180
gatcggttct ctggctccat cgacagctcc tccaactctg cctccctcac catctctgga    240
ctgaagattg aggacgaggc tgactactac tgtcagtctt atgatagcaa caatcaggtg    300
ttcggcggcg ggaccaagct gaccgtccta cgt                                333

<210> SEQ ID NO 150
<211> LENGTH: 333
<212> TYPE: DNA
<213> ORGANISM: Artificial Sequence
<220> FEATURE:
<223> OTHER INFORMATION: Synthetic Nucleotide sequence of light chain
      variable region of anti-HER2 antibody 44-C12

<400> SEQUENCE: 150
cagactgtgg tgactcagga gccatcgttc tcagtgtccc ctggagggac agtcacactc    60
acttgtggct tgagctctgg ctcagtctct cctacttatt accccagctg gtaccagcag    120
accccaggcc aggctccacg cacgctcatc tacaggacaa acattcgctc ttctggggtc    180
cctgatcgct tctctggctc catccttggg aacaaagctg ccctcaccat cacggggcc    240 caggcagatg atgagtctct ctattactgt ttgctctata tgggtagtgg cgtttcgctg    300
ttcggcggag ggaccaagct gaccgtccta cgt                                333
```

```
<210> SEQ ID NO 151
<211> LENGTH: 333
<212> TYPE: DNA
<213> ORGANISM: Artificial Sequence
<220> FEATURE:
<223> OTHER INFORMATION: Synthetic Nucleotide sequence of light chain
      variable region of anti-HER2 antibody 44-H4

<400> SEQUENCE: 151
caggctgtgg tgacccagga gccatcgttc tcagtgtccc ctggagggac agtcacactc      60
acttgtggct tgagctctgg ctcagtctct actagttact accccagctg gtaccagcag     120
accccaggcc aggctccacg cacgctcatc tacagcacaa acactcgctc ctctggggtc     180
cctgatcgct tctctggctc catccttggg aacaaagctg ccctcaccat cacgggggcc     240
cagacagatg atgaatctga ttattactgt gtgctgtata tgggtagtgg catttcgcta     300
ttcggcggag ggaccaaggt gaccgtccta ggt                                  333

<210> SEQ ID NO 152
<211> LENGTH: 41
<212> TYPE: DNA
<213> ORGANISM: Artificial Sequence
<220> FEATURE:
<223> OTHER INFORMATION: Synthetic Forward primer for anti-HER2 scFv
      41-B11

<400> SEQUENCE: 152
ggttccggag gcggcggatc cgaggtgcag ctggtgcagt c                          41

<210> SEQ ID NO 153
<211> LENGTH: 46
<212> TYPE: DNA
<213> ORGANISM: Artificial Sequence
<220> FEATURE:
<223> OTHER INFORMATION: Synthetic Reverse primer for anti-HER2 scFv
      41-B11

<400> SEQUENCE: 153
agggatcgaa cccttctcga gtcaacctag gacggtcaac ttggtc                     46

<210> SEQ ID NO 154
<211> LENGTH: 44
<212> TYPE: DNA
<213> ORGANISM: Artificial Sequence
<220> FEATURE:
<223> OTHER INFORMATION: Synthetic Forward primer for anti-HER2 scFv
      41-C6

<400> SEQUENCE: 154
ggttccggag gcggcggatc ccagatccag ctggtacaat ctgg                       44

<210> SEQ ID NO 155
<211> LENGTH: 45
<212> TYPE: DNA
<213> ORGANISM: Artificial Sequence
<220> FEATURE:
<223> OTHER INFORMATION: Synthetic Reverse primer for anti-HER2 scFv
      41-C6

<400> SEQUENCE: 155
agggatcgaa cccttctcga gtcaacctag gacggtcagc ttggt                      45

<210> SEQ ID NO 156
<211> LENGTH: 41
<212> TYPE: DNA
<213> ORGANISM: Artificial Sequence
```

<220> FEATURE:
<223> OTHER INFORMATION: Synthetic Forward primer for anti-HER2 scFv
      41-E1

<400> SEQUENCE: 156
ggttccggag gcggcggatc cgaggtgcag ctggtggagt c         41

<210> SEQ ID NO 157
<211> LENGTH: 45
<212> TYPE: DNA
<213> ORGANISM: Artificial Sequence
<220> FEATURE:
<223> OTHER INFORMATION: Synthetic Reverse primer for anti-HER2 scFv
      41-E1

<400> SEQUENCE: 157
agggatcgaa cccttctcga gtcaacgtag gacggtcagc ttggt     45

<210> SEQ ID NO 158
<211> LENGTH: 42
<212> TYPE: DNA
<213> ORGANISM: Artificial Sequence
<220> FEATURE:
<223> OTHER INFORMATION: Synthetic Forward primer for anti-HER2 scFv
      44-C12

<400> SEQUENCE: 158
ggttccggag gcggcggatc cgaagtgcag ctggtgcagt ct        42

<210> SEQ ID NO 159
<211> LENGTH: 45
<212> TYPE: DNA
<213> ORGANISM: Artificial Sequence
<220> FEATURE:
<223> OTHER INFORMATION: Synthetic Reverse primer for anti-HER2 scFv
      44-C12

<400> SEQUENCE: 159
agggatcgaa cccttctcga gtcaacgtag gacggtcagc ttggt     45

<210> SEQ ID NO 160
<211> LENGTH: 41
<212> TYPE: DNA
<213> ORGANISM: Artificial Sequence
<220> FEATURE:
<223> OTHER INFORMATION: Synthetic Forward primer for anti-HER2 scFv
      44-H4

<400> SEQUENCE: 160
ggttccggag gcggcggatc cgaggtgcag ctggtgcagt c         41

<210> SEQ ID NO 161
<211> LENGTH: 45
<212> TYPE: DNA
<213> ORGANISM: Artificial Sequence
<220> FEATURE:
<223> OTHER INFORMATION: Synthetic Reverse primer for anti-HER2 scFv
      44-H4

<400> SEQUENCE: 161
agggatcgaa cccttctcga gtcaacctag gacggtcacc ttggt     45

<210> SEQ ID NO 162
<211> LENGTH: 114
<212> TYPE: PRT
<213> ORGANISM: Artificial Sequence
<220> FEATURE:

```
<223> OTHER INFORMATION: Synthetic light chain variable region of anti
      c-Met antibody

<400> SEQUENCE: 162

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg
```

ANTI-HER2 ANTIBODY AND ANTI-C-MET/ANTI-HER2 BISPECIFIC ANTIBODIES COMPRISING THE SAME

CROSS-REFERENCE TO RELATED APPLICATIONS

This application claims the benefit of Korean Patent Application No. 10-2014-0055665 filed on May 9, 2014 and Korean Patent Application No. 10-2015-0055501 filed on Apr. 20, 2015 in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 160,296 byte ASCII (Text) file named "720110_ST25.TXT," created Apr. 27, 2015.

BACKGROUND

1. Field

Provided are an anti-HER2 antibody or antigen binding fragment thereof, an anti-c-Met/anti-HER2 bispecific antibody, and a method of preventing and/or treating a cancer using the anti-HER2 antibody or antigen binding fragment thereof or the c-Met/anti-HER2 bispecific antibody.

2. Description of the Related Art c-Met and HER2 (or HER family of proteins) interact with each other and are involved in various mechanisms related to tumors. These proteins (targets) are typical receptor tyrosine kinases (RTKs) present at the surface of cells, thereby inducing the proliferation of cancer cells, the penetration of the cancer cells, angiogenesis, etc. Also, these proteins participate in each other's signal transduction systems by interacting with each other, thereby inducing resistance against each other's therapeutic agents.

Meanwhile, multispecific antibodies targeting two or more antigens have been developed in various kinds and forms and are expected as a new drug antibody having excellent therapeutic effects compared to a monoclonal antibody. Most multispecific antibodies have been developed so that their therapeutic effects on cancers can be increased by recognizing an antigen of cytotoxic cells (killer cells) and another antigen of cancer cells at the same time thus allowing the cancer cells to be killed by the cytotoxic cells. However, when considering that the research results reveal that cancer cells themselves can be mutated to proliferate and penetrate even by intracellular ligands or various antigens of the same cancer cells, it is expected that a multispecific antibody capable of recognizing two or more of such cancer related ligands or antigens of the cancer cells will be also useful in treating cancers.

Accordingly, there is a need for the development of a multispecific antibody which is predicted to achieve effective cancer treatment by recognizing two or more kinds of antigens in cancer cells at the same time (e.g., a bispecific antibody), as well as an antibody targeting a cancer-related antigen such as a RTK.

SUMMARY

One embodiment provides a polypeptide including one amino acid sequence or a combination of two or more amino acid sequences selected from the group consisting of SEQ ID NO: 109 to SEQ ID NO: 131.

Another embodiment provides an anti-HER2 antibody or an antigen-binding fragment thereof including or consisting essentially of at least one heavy chain complementarity determining region selected from the group consisting of CDR-H1 including the amino acid sequence selected from the group consisting of SEQ ID NOs: 109 to 111, CDR-H2 including the amino acid sequence selected from the group consisting of SEQ ID NOs: 112 to 114, and CDR-H3 including the amino acid sequence selected from the group consisting of SEQ ID NOs: 115 to 119; at least one light chain complementarity determining region selected from the group consisting of CDR-L1 including the amino acid sequence selected from the group consisting of SEQ ID NOs: 120 to 123, CDR-L2 including the amino acid sequence selected from the group consisting of SEQ ID NO: 124 to 126, and CDR-L3 including the amino acid sequence selected from the group consisting of SEQ ID NO: 127 to 131; or a combination of the at least one heavy chain complementarity determining region and the at least one light chain complementarity determining region.

Another embodiment provides an anti-c-Met/anti-HER2 bispecific antibody including an anti-c-Met antibody or an antigen-binding fragment thereof and an anti-HER2 antibody or an antigen-binding fragment thereof, wherein the anti-c-Met antibody or an antigen-binding fragment thereof specifically binds to an epitope including 5 or more contiguous amino acids within SEMA domain (SEQ ID NO: 79) of c-Met protein, and the anti-HER2 antibody or an antigen-binding fragment thereof includes or consists essentially of at least one heavy chain complementarity determining region selected from the group consisting of CDR-H1 including the amino acid sequence selected from the group consisting of SEQ ID NOs: 109 to 111, CDR-H2 including the amino acid sequence selected from the group consisting of SEQ ID NOs: 112 to 114, and CDR-H3 including the amino acid sequence selected from the group consisting of SEQ ID NOs: 115 to 119; at least one light chain complementarity determining region selected from the group consisting of CDR-L1 including the amino acid sequence selected from the group consisting of SEQ ID NOs: 120 to 123, CDR-L2 including the amino acid sequence selected from the group consisting of SEQ ID NO: 124 to 126, and CDR-L3 including the amino acid sequence selected from the group consisting of SEQ ID NO: 127 to 131; or a combination of the at least one heavy chain complementarity determining region and the at least one light chain complementarity determining region.

Another embodiment provides a pharmaceutical composition including the polypeptide, the anti-HER2 antibody or an antigen-binding fragment thereof, or the anti-c-Met/anti-HER2 bispecific antibody or an antigen-binding fragment thereof, as an active ingredient.

Another embodiment provides a method of preventing and/or treating a cancer including administering the polypeptide, the anti-HER2 antibody or an antigen-binding fragment thereof, or the anti-c-Met/anti-HER2 bispecific antibody or an antigen-binding fragment thereof, to a subject in need of preventing and/or treating a cancer.

DETAILED DESCRIPTION

Figure 1:
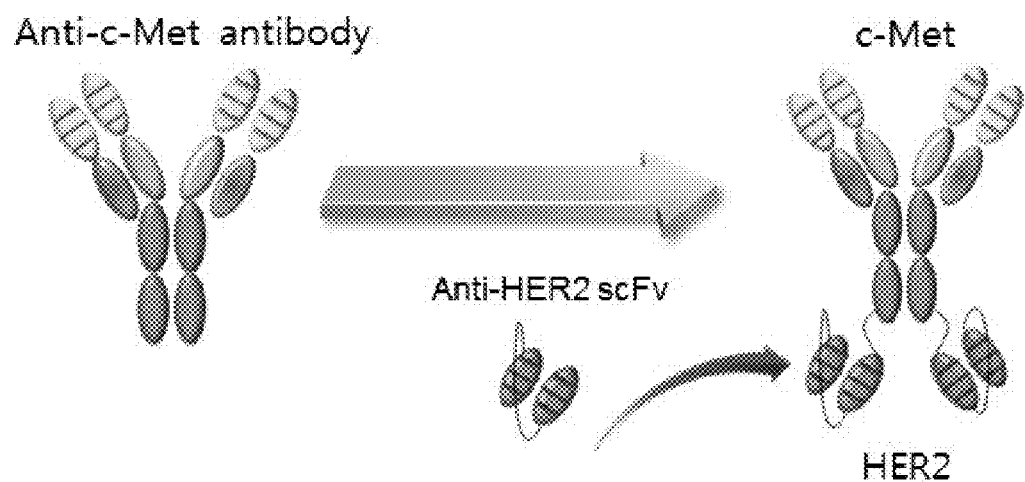
FIG. 1 is a schematic of an anti-c-Met/anti-HER2 bispecific antibody.

In therapy using the existing targeting drugs which recognize only HER2, a typical target widely expressed on cancer cells, over-expression and abnormal activation of c-Met is induced, allowing cancer cells to acquire resistance against the drugs, whereby the therapeutic effects of the drugs could be reduced. In this regard, in the description, it is verified that a bispecific antibody recognizing c-Met and HER2 at the same time prevents the development of resistance and shows excellent cancer cell inhibitory effects, even in cancer cells having resistance, by blocking c-Met-implicated signal transduction which causes resistance against drugs. In addition, an anti-HER2 antibody comprising certain CDRs, which has an increased therapeutic effect compared to the existing anti-HER2 antibodies, is also provided.

Although various bispecific antibodies have been developed, their efficiency was not proved in clinical tests or their several side effects were observed. For these reasons, there were many cases which were not approved by FDA and were not marketed as therapeutic antibodies. In spite of the fact that bispecific antibodies having various forms and mechanisms have been developed, the bispecific antibodies were not marketed due to a problem in the stability and productivity of the antibodies. In the production of early bispecific antibodies having an IgG form, due to random combination between light chains and heavy chains of antibodies, it is very difficult to separate and purify a desired kind of bispecific antibody, which becomes an obstacle in the mass production. Also, in the case of bispecific antibodies with non-IgG forms, their stabilities as a drug were not verified in protein folding, pharmacokinetics, and the like. In the present invention, it is verified that a bispecific antibody in which an anti-c-Met antibody is fused to an antibody recognizing a secondary target, HER2, or an antigen binding fragment thereof (e.g., scFv) could improve and address the stability issue, which was the biggest problem of the pre-existing bispecific antibodies.

One embodiment provides a polypeptide including a novel amino acid sequence. The polypeptide may function as a CDR of an anti-HER2 antibody. In particular, the polypeptide may include one amino acid sequence or a combination of two or more amino acid sequences selected from the group consisting of SEQ ID NO: 109 to SEQ ID NO: 131. The possible function of the polypeptide including the amino acid sequence of SEQ ID NO: 109 to SEQ ID NO: 131 as a CDR of an anti-HER2 antibody is summarized in Tables 1 and 2, as follows:

TABLE 1

| CDR-H1 | CDR-H2 | CDR-H3 |
|---|---|---|
| SYWIG (SEQ ID NO: 109); | IIYPGDSDTRYSPSFQG (SEQ ID NO: 112); | RHYYDSSGYSYFPDY (SEQ ID NO: 115); |
| DYAMS (SEQ ID NO: 110); or | FIRSKAYGGTTEYAASVKG (SEQ ID NO: 113); or | RLSVAAAGTGGYNWFDP (SEQ ID NO: 116); |
| SYAIS (SEQ ID NO: 111) | GIIPIFGTANYAQKFQG (SEQ ID NO: 114) | RDLYPAMAEY (SEQ ID NO: 117); |
|  |  | RDSGYSYGYPMNYYYYYMDV (SEQ ID NO: 118); or |
|  |  | RLVVGANPPTYYFDY (SEQ ID NO: 119) |

TABLE 2

| CDR-L1 | CDR-L2 | CDR-L3 |
|---|---|---|
| GLSSGSVSTSYYPS (SEQ ID NO: 120); | STNTRSSGVPD (SEQ ID NO: 124); | VLYMGSGIWV (SEQ ID NO: 127); |
| GLTSGSVSTSYYPS (SEQ ID NO: 121); | DDNQRPSGVPD (SEQ ID NO: 125); or | MLYLGGGISV (SEQ ID NO: 128); |
| TRSSGSIDSNFVQ (SEQ ID NO: 122); or | RTNIRSSGVPD (SEQ ID NO: 126) | QSYDSNNQV (SEQ ID NO: 129) |
| GLSSGSVSPTYYPS (SEQ ID NO: 123) |  | LLYMGSGVSL (SEQ ID NO: 130); or |
|  |  | VLYMGSGISL (SEQ ID NO: 131) |

In one embodiment, a combination of two or more of the polypeptides may be used as a heavy chain variable region or light chain variable region of an anti-HER2 antibody.

In one particular embodiment, the polypeptide may comprise a polypeptide (capable of serving as CDR-H1) comprising the amino acid sequence selected from the group consisting of SEQ ID NOs: 109 to 111, a polypeptide (capable of serving as CDR-H2) comprising the amino acid sequence selected from the group consisting of SEQ ID NOs: 112 to 114, and a polypeptide (capable of serving as CDR-H3) comprising the amino acid sequence selected from the group consisting of SEQ ID NOs: 115 to 119, and for example, the polypeptide may comprise the amino acid sequence selected from the group consisting of SEQ ID NOs: 132 to 136. For example, the polypeptide may function as a heavy chain variable region of an anti-HER2 antibody.

In another particular embodiment, the polypeptide may comprise a polypeptide (capable of serving as CDR-L1) comprising the amino acid sequence selected from the group consisting of SEQ ID NOs: 120 to 123, a polypeptide (capable of serving as CDR-L2) comprising the amino acid sequence selected from the group consisting of SEQ ID NOs: 124 to 126, and a polypeptide (capable of serving as CDR-L3) comprising the amino acid sequence selected from the group consisting of SEQ ID NOs: 127 to 131, and for example, the polypeptide may comprise the amino acid sequence selected from the group consisting of SEQ ID NOs: 137 to 141. For example, the polypeptide may function as a light chain variable region of an anti-HER2 antibody.

In another particular embodiment, the polypeptide may comprise a combination of:

a polypeptide (capable of serving as CDR-H1) comprising the amino acid sequence selected from the group consisting of SEQ ID NOs: 109 to 111, a polypeptide (capable of serving as CDR-H2) comprising the amino acid sequence selected from the group consisting of SEQ ID NOs: 112 to 114, and a polypeptide (capable of serving as CDR-H3) comprising the amino acid sequence selected from the group consisting of SEQ ID NOs: 115 to 119; and a polypeptide (capable of serving as CDR-L1) comprising the amino acid sequence selected from the group consisting of SEQ ID NOs: 120 to 123, a polypeptide (capable of serving as CDR-L2) comprising the amino acid sequence selected from the group consisting of SEQ ID NOs: 124 to 126, and a polypeptide (capable of serving as CDR-L3) comprising the amino acid sequence selected from the group consisting of SEQ ID NOs: 127 to 131.

For example, the polypeptide may comprise a combination of the amino acid sequence selected from the group consisting of SEQ ID NOs: 132 to 136 and the amino acid sequence selected from the group consisting of SEQ ID NOs: 137 to 141. For example, the polypeptide may function as a heavy chain variable region of an anti-HER2 antibody. for example, the polypeptide may comprise the amino acid sequence selected from the group consisting of SEQ ID NOs: 137 to 141. For example, the polypeptide may function as an anti-HER2 antibody or an antigen-binding fragment thereof comprising a heavy chain variable region and a light chain variable region.

The polypeptide may be non-naturally occurring. For example, the polypeptide may be obtained by recombination, synthesis (artificial synthesis), and/or digestion of a protein (e.g., a recombinant or synthetic protein) containing the polypeptide.

The polypeptide may act as a precursor or a component of an HER2 antagonist, such as an anti-HER2 antibody, an antigen-binding fragment thereof, or an anti-HER2 antibody analog (e.g., a peptibody, nanobody, etc.).

Therefore, another embodiment provides an anti-HER2 antagonist including the polypeptide. The antagonist inhibits the HER2 activity, and may be one or more selected from the group consisting of an anti-HER2 antibody, an antigen-binding fragment thereof, an anti-HER2 antibody analogue (e.g., a peptibody, nanobody, etc.), and the like.

The "HER2 (Human epidermal growth factor receptor 2)" is encoded by ERBB2 gene, and a member of an epidermal growth factor receptor (ErbB) family. HER2 plays an essential role in regulation of cell proliferation and differentiation. In particular, the binding of a ligand (a growth factor) to the extracellular domain of HER2 induces receptor homo- or hetero dimerization with other ErbB receptors, which in turn results in activating various types of signal transduction pathways, thereby inducing apoptosis, cell survival, or cell proliferation. For example, the HER2 may be human HER2 (e.g., GenBank Accession Nos. NP_004439.2, NP_001005862, etc.), mouse HER2 (e.g., GenBank Accession No. NP_001003817, etc.), which are encoded by polynucleotide sequences (mRNA) of GenBank Accession Numbers NM 004448.2, NM NM_001005862.1, NM_001003817, respectively.

The term "antagonist" may include any molecule capable of completely or partially preventing, inhibiting, or neutralizing one or more biological activities of a target (e.g., HER2). For instance, an antibody as an antagonist may refer to an antibody capable of inhibiting or lowering biological activities of an antigen (e.g., HER2) to which the antibody binds. The antagonist may bind to a receptor for a ligand (target) to decrease receptor phosphorylation, or incapacitating or killing a cell that is activated by the ligand. In addition, the antagonist may substantially decrease an interaction between a receptor and its ligand, by completely or partially blocking the receptor-ligand interaction, binding to the receptor competitively with its ligand, or modifying three-dimensional structure of the receptor.

Term "peptibody (peptide+antibody)" may refer to a fusion protein wherein a peptide is fused with the whole or a part of a constant region of an antibody, such as Fc region, and the peptide acts as an antigen-binding region (e.g., a CDR or variable region of a heavy chain and/or light chain), thereby having a structure and functions similar to an antibody.

Term "nanobody" that is also called as a single-domain antibody, may refer to an antibody fragment including a single variable domain in a monomeric form and selectively binding to a specific antigen, similarly to an antibody in a complete form. The nanobody usually has a molecular weight of about 12 kDa to about 15 kDa, which is much smaller than an general molecular weight (about 150 kDa to about 160 kDa) of an antibody in a complete form (including two heavy chains and two light chains), and in some cases, smaller than a molecular weight of a Fab fragment or a scFv fragment.

In a particular embodiment, the polypeptide may act as a precursor or a component of an anti-HER2 antibody.

Another embodiment provides an anti-HER2 antibody or an antigen-binding fragment thereof including the polypeptide. The antigen-binding fragment may be selected from the group consisting of scFv, (scFv)2, scFv-Fc, Fab, Fab' and F(ab')2.

In particular, the anti-HER2 antibody or an antigen-binding fragment thereof may comprise or consist essentially of:

at least one heavy chain complementarity determining region selected from the group consisting of CDR-H1 comprising or consisting essentially of the amino acid sequence selected from the group consisting of SEQ ID NOs: 109 to 111, CDR-H2 comprising or consisting essentially of the amino acid sequence selected from the group consisting of SEQ ID NOs: 112 to 114, and CDR-H3 comprising or consisting essentially of the amino acid sequence selected from the group consisting of SEQ ID NOs: 115 to 119, or a heavy chain variable region including the at least one heavy chain complementarity determining region;

at least one light chain complementarity determining region selected from the group consisting of CDR-L1 comprising or consisting essentially of the amino acid sequence selected from the group consisting of SEQ ID NOs: 120 to 123, CDR-L2 comprising or consisting essentially of the amino acid sequence selected from the group consisting of SEQ ID NOs: 124 to 126, and CDR-L3 comprising or consisting essentially of the amino acid sequence selected from the group consisting of SEQ ID NOs: 127 to 131, or a light chain variable region including the at least one light chain complementarity determining region;

a combination of the at least one heavy chain complementarity determining region and the at least one light chain complementarity determining region; or a combination of the heavy chain variable region and the light chain variable region.

For example, the anti-HER2 antibody or an antigen-binding fragment thereof may comprise or consisting essentially of a heavy chain variable region comprising or consisting essentially of the amino acid sequence selected from the group consisting of SEQ ID NOs: 132 to 136, a light chain variable region comprising or consisting essentially of the amino acid sequence selected from the group consisting of SEQ ID NOs: 137 to 141, or a combination thereof.

In a particular embodiment, the anti-HER2 antibody or an antigen-binding fragment thereof may be an anti-HER2 scFv comprising or consisting essentially of a heavy chain variable region comprising or consisting essentially of the amino acid sequence selected from the group consisting of SEQ ID NOs: 132 to 136, and a light chain variable region comprising or consisting essentially of the amino acid sequence selected from the group consisting of SEQ ID NOs: 137 to 141.

In the polypeptide or an antigen-binding fragment (e.g., an anti-HER2 scFv) of the anti-HER2 antibody, the heavy chain variable region and the light chain variable region may be linked with a linker (e.g., a peptide linker) or directly linked without a linker. The peptide linker may be those including any amino acids of 1 to 100, particularly 2 to 50, and any kinds of amino acids may be included without any restrictions. The peptide linker may include for example, Gly, Asn and/or Ser residues, and also include neutral amino acids such as Thr and/or Ala. Amino acid sequences suitable for the peptide linker may be those known in the relevant art. Meanwhile, a length of the peptide linker may be variously determined within such a limit that the functions of the fusion protein will not be affected. For instance, the peptide linker may be formed by including a total of about 1 to about 100, about 2 to about 50, or about 5 to about 25 of one or more selected from the group consisting of Gly, Asn, Ser, Thr, and Ala. In one embodiment, the peptide linker may be represented as $(GGGGS)_n$ (n is an integer of about 1 to about 10, particularly an integer of about 2 to about 5).

The antibody may include all of an animal antibody, a chimeric antibody, a humanized antibody, and a human antibody. In addition the antibody may include an antigen-binding fragment derived (obtained) from an antibody having an antigen binding affinity.

The "complementarity-determining region (CDR)" may refer to a region within a variable region, which give a binding specificity to an antigen. The antigen-binding fragment as described above may be an antibody fragment including at least one complementarity-determining region, for example, one or more selected from the group consisting of scFv, (scFv)2, scFv-Fc, Fab, Fab', and F(ab')2.

In an anti-HER2 antibody or an antigen-binding fragment thereof, the rest portion of the light chain and the heavy chain portion excluding the CDRs, the light chain variable region, and the heavy chain variable region as defined above, e.g., a light chain constant region and a heavy chain constant region, may be those from any subtype of immunoglobulin (e.g., IgA, IgD, IgE, IgG (IgG1, IgG2, IgG3, IgG4), IgM, and the like).

Based on the ability of specifically binding to HER2, the anti-HER2 antibody or an antigen-binding fragment thereof may be used in detecting HER2 or confirming activation and/or overproduction (i.e. overexpression) of HER2.

One embodiment provides a composition for detecting the presence of HER2 including the anti-HER2 antibody or an antigen-binding fragment thereof. Another embodiment provides a method of detecting HER2 including treating a biological sample with the anti-HER2 antibody or an antigen-binding fragment thereof; and detecting an antigen-antibody reaction (binding). In the method of detecting, when an antigen-antibody reaction is detected, it can be determined that HER2 is present in the biological sample. Another embodiment provides a use of the anti-HER2 antibody or an antigen-binding fragment thereof for detecting HER2. The biological sample may be selected from the group consisting of a cell, a tissue, a body fluid (e.g., blood, serum, etc.), and the like derived (obtained or separated) from a mammal including primates such as a human, a monkey, and the like, or a rodent such as a mouse, a rat, and the like. The biological sample may be separated from a living body. The detection of HER2 may refer to detection of presence of HER2, expression of HER2, or the level of HER2.

Another embodiment provides a pharmaceutical composition for diagnosing activation and/or overproduction of HER2 or a disease associated with activation and/or overproduction of HER2 including the anti-HER2 antibody or an antigen-binding fragment thereof. Another embodiment provides a method of diagnosing (or determining) activation and/or overproduction of HER2 or a disease associated with activation and/or overproduction of HER2, including treating a biological sample derived from a patient with the anti-HER2 antibody or an antigen-binding fragment thereof, and measuring a level of an antigen-antibody reaction. In this method, when the level of the antigen-antibody reaction in the biological sample is higher than that of a normal sample, the patient from which the biological sample is derived may be determined as having activation and/or overproduction of HER2 or a disease associated with activation and/or overproduction of HER2. Therefore, the method may further include treating a normal sample with the anti-HER2 antibody or an antigen-binding fragment thereof, and measuring a level of an antigen-antibody reaction. Another embodiment provides a use of the anti-HER2 antibody or an antigen-binding fragment thereof in diagnosing activation and/or overproduction of HER2 or a disease associated with activation and/or overproduction of HER2.

The biological sample may be at least one selected from the group consisting of a cell, a tissue, fluid (e.g., blood, serum, and the like) and the like, derived (obtained or separated) from a patient to be diagnosed. The biological sample may be separated from a living body. The normal sample may be at least one selected from the group consisting of a cell, a tissue, fluid (e.g., blood, serum, and the like) and the like, derived (obtained or separated) from a patient having no condition of activation and/or overproduction of HER2 or a disease associated with activation and/or overproduction of HER2. The normal sample may be separated from a living body. The patient may be selected from a mammal, including primates such as a human, a monkey, and the like, and rodents such as a mouse, a rat, and the like.

The step of measuring a level of an antigen-antibody reaction may be performed by any general method known to the relevant art, such as general enzymatic reactions, fluorescent reactions, luminescent reactions, and/or detection of radiation. For example, the step may be performed by a method selected from, but not limited to, the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, microarray, surface plasmon resonance (SPR), flow cytometry assay, and the like.

Another embodiment provides an anti-c-Met/anti-HER2 bispecific antibody or an antigen-binding fragment thereof comprising an anti-c-Met antibody or an antigen-binding fragment thereof and an anti-HER2 antibody or an antigen-binding fragment thereof. The antigen-binding fragment of an anti-c-Met antibody or an anti-JER2 antibody may be independently selected from the group consisting of scFv, (scFv)2, scFvFc, Fab, Fab', and F(ab')2.

The "c-Met protein" refers to a receptor tyrosine kinase binding to hepatocyte growth factor. The c-Met proteins may be derived from any species, for example, those derived from primates such as human c-Met (e.g., NP_000236.2) and monkey c-Met (e.g., *Macaca mulatta*, NP_001162100), or those derived from rodents such as mouse c-Met (e.g., NP_032617.2) and rat c-Met (e.g., NP_113705.1). The proteins include, for example, a polypeptide encoded by the nucleotide sequence deposited under GenBank Accession Number NM_000245, or a protein encoded by the polypeptide sequence deposited under GenBank Accession Number NM_000236.2, or extracellular domains thereof. The receptor tyrosine kinase c-Met is involved in several mechanisms including cancer incidence, cancer metastasis, cancer cell migration, cancer cell penetration, angiogenesis, etc.

In one embodiment, the anti-c-Met/anti-HER2 bispecific antibody may include an anti-c-Met antibody or an antigen binding fragment thereof, and an anti-HER2 antibody or an antigen binding fragment thereof which is linked to the C terminus or N terminus, for example, C terminal, of the anti-c-Met antibody or the antigen binding fragment thereof.

In the anti-c-Met/anti-HER2bispecific antibody, in order to fully perform the anti-c-Met antibody's activity to mediate intracellular migration and degradation of c-Met proteins, the anti-c-Met antibody may contain its own intact antibody structure. In addition, in case of the anti-HER2 antibody, its specific recognition and binding to HER2 is important, and thus it is acceptable that just an antigen-binding fragment recognizing HER2 is included in the bispecific antibody. Therefore, the anti-c-Met/anti-HER2 bispecific antibody may be those including a full length anti-c-Met antibody (e.g., IgG type antibody comprising two heavy chains and two light chains) and an antigen binding fragment (such as, scFv, (scFv)$_2$, Fab, Fab' or F(ab')$_2$) of the anti-HER2 antibody linked to the C terminus of the anti-c-Met antibody (for example, one or both of heavy chains or light chains (in particular, heavy chains) of the full length anti-c-Met antibody). For example, the anti-c-Met antibody and the antigen-binding fragment of the anti-HER2 antibody may be linked to each other via a chemical bond, such as a covalent bond. In particular, the antigen-binding fragment of the anti-HER2 antibody may be linked to the C-terminus of the anti-c-Met antibody (for example, one or both of heavy chains or light chains (in particular, heavy chains) of the full length anti-c-Met antibody), directly (with no linker) or via a linker.

In the anti-c-Met/anti-HER2 bispecific antibody, the anti-c-Met antibody or the antigen binding fragment thereof, and the anti-HER2 antibody or the antigen binding fragment thereof, may be linked via a peptide linker, or they may be linked directly and without a linker. Furthermore, a heavy chain portion and a light chain portion within the antigen binding fragment, for example, a heavy chain variable region and a light chain variable region within the scFv fragment, may be linked via a peptide linker or without a linker. The peptide linker which links the anti-c-Met antibody or the antigen binding fragment thereof and the anti-HER2 antibody or the antigen binding fragment thereof, and the peptide linker which links the heavy chain portion and the light chain portion within the antigen binding fragment, may be identical or different. The peptide linker may be include about 1 to about 100 amino acid residues, particularly about 2 to about 50, and any kinds of amino acids may be included without any restrictions. The peptide linker may include for example, Gly, Asn and/or Ser residues, and also include neutral amino acids such as Thr and/or Ala. Amino acid sequences suitable for the peptide linker may be those known in the pertinent art. Meanwhile, a length of the peptide linker may be variously determined within such a limit that the functions of the fusion protein will not be affected. For instance, the peptide linker may be formed by including a total of about 1 to about 100, about 2 to about 50, or about 5 to about 25 of one or more selected from the group consisting of Gly, Asn, Ser, Thr, and Ala. In one embodiment, the peptide linker may be represented as (GGGS)$_n$ (n is an integer of about 1 to about 10, particularly an integer of about 2 to about 5).

In a particular embodiment, the anti-HER2 antibody or an antigen-biding fragment may comprise or consist essentially of:

at least one heavy chain complementarity determining region selected from the group consisting of CDR-H1 comprising or consisting essentially of the amino acid sequence selected from the group consisting of SEQ ID NOs: 109 to 111, CDR-H2 comprising or consisting essentially of the amino acid sequence selected from the group consisting of SEQ ID NOs: 112 to 114, and CDR-H3 comprising or consisting essentially of the amino acid sequence selected from the group consisting of SEQ ID NOs: 115 to 119, or a heavy chain variable region including the at least one heavy chain complementarity determining region;

at least one light chain complementarity determining region selected from the group consisting of CDR-L1 comprising or consisting essentially of the amino acid sequence selected from the group consisting of SEQ ID NOs: 120 to 123, CDR-L2 comprising or consisting essentially of the amino acid sequence selected from the group consisting of SEQ ID NOs: 124 to 126, and CDR-L3 comprising or consisting essentially of the amino acid sequence selected from the group consisting of SEQ ID NOs: 127 to 131, or a light chain variable region including the at least one light chain complementarity determining region;

a combination of the at least one heavy chain complementarity determining region and the at least one light chain complementarity determining region; or a combination of the heavy chain variable region and the light chain variable region.

For example, the anti-HER2 antibody or an antigen-binding fragment thereof may comprise or consist essentially of a heavy chain variable region comprising or consisting essentially of the amino acid sequence selected from the group consisting of SEQ ID NOs: 132 to 136, a light chain variable region comprising or consisting essentially of the amino acid sequence selected from the group consisting of SEQ ID NOs: 137 to 141, or a combination thereof.

In a particular embodiment, the anti-HER2 antibody or an antigen-binding fragment thereof may be an anti-HER2 scFv comprising or consisting essentially of a heavy chain variable region comprising or consisting essentially of the amino acid sequence selected from the group consisting of SEQ ID NOs: 132 to 136, and a light chain variable region comprising or consisting essentially of the amino acid sequence selected from the group consisting of SEQ ID NOs: 137 to 141.

The "antigen binding fragment" refers to a fragment of a full immunoglobulin structure including parts of the polypeptide including a portion capable of binding to an antigen. For example, it may be scFv, (scFv)$_2$, Fab, Fab', or F(ab')$_2$, but not be limited thereto. In the present invention, the antigen binding fragment may be an antibody fragment including at least one complementarity determining region, for example, selected from the group consisting of scFv, (scFv)2, scFv-Fc, Fab, Fab' and F(ab')2.

Of the antigen binding fragments, Fab is a structure having variable regions of a light chain and a heavy chain, a constant region of the light chain, and the first constant region (C$_{H1}$) of the heavy chain, and it has one antigen binding site.

Fab' is different from Fab in that it has a hinge region including one or more cysteine residues at the C-terminal of heavy chain C$_{H1}$ domain. An F(ab')$_2$ antibody is formed through disulfide bond of the cysteine residues at the hinge region of Fab'.

Fv is a minimal antibody piece having only a heavy chain variable region and light chain variable region, and a recombinant technique for producing the Fv fragment is well known in the pertinent art. Two-chain Fv may have a structure in which the heavy chain variable region is linked to the light chain variable region by a non-covalent bond, and single-chain Fv (scFv) may generally have a dimer structure as in the two-chain Fv in which the variable region of a heavy chain and the variable region of a light chain are covalently linked via a peptide linker or they are directly linked to each other at the C-terminal thereof. The peptide linker may be the same as described herein.

The antigen binding fragments may be obtained using proteases (for example, a whole antibody is digested with papain to obtain Fab fragments, and is digested with pepsin to obtain F(ab')$_2$ fragments), and may be prepared by a genetic recombinant technique.

For instance, in the anti-c-Met/anti-HER2 bispecific antibody, scFv, (scFv)$_2$, scFv-Fc, Fab, Fab', or F(ab')$_2$ of the anti-HER2 antibody may comprise or consisting essentially of at least one heavy chain complementarity determining region selected from the group consisting of CDR-H1 comprising or consisting essentially of the amino acid sequence selected from the group consisting of SEQ ID NOs: 109 to 111, CDR-H2 comprising or consisting essentially of the amino acid sequence selected from the group consisting of SEQ ID NOs: 112 to 114, and CDR-H3 comprising or consisting essentially of the amino acid sequence selected from the group consisting of SEQ ID NOs: 115 to 119, or a heavy chain variable region including the at least one heavy chain complementarity determining region; and at least one light chain complementarity determining region selected from the group consisting of CDR-L1 comprising or consisting essentially of the amino acid sequence selected from the group consisting of SEQ ID NOs: 120 to 123, CDR-L2 comprising or consisting essentially of the amino acid sequence selected from the group consisting of SEQ ID NOs: 124 to 126, and CDR-L3 comprising or consisting essentially of the amino acid sequence selected from the group consisting of SEQ ID NOs: 127 to 131, or a light chain variable region including the at least one light chain complementarity determining region.

For example, the scFv, (scFv)$_2$, scFv-Fc, Fab, Fab', or F(ab')$_2$ of the anti-HER2 antibody may be those comprising or consisting essentially of a heavy chain variable region comprising or consisting essentially of the amino acid sequence selected from the group consisting of SEQ ID NOs: 132 to 136, and a light chain variable region comprising or consisting essentially of the amino acid sequence selected from the group consisting of SEQ ID NOs: 137 to 141.

In a particular embodiment, the anti-c-Met/anti-HER2 bispecific antibody may be those including i) an anti-c-Met antibody, and ii) scFv, (scFv)$_2$, scFv-Fc, Fab, Fab' or F(ab')$_2$ of the anti-HER2 antibody including a heavy chain variable region comprising or consisting essentially of the amino acid sequence selected from the group consisting of SEQ ID NOs: 132 to 136, and a light chain variable region comprising or consisting essentially of the amino acid sequence selected from the group consisting of SEQ ID NOs: 137 to 141, linked to the C terminal of the anti-c-Met antibody (e.g., a heavy chain of the anti-c-Met antibody).

The anti-c-Met antibody may be any one recognizing a specific region of c-Met, e.g., a specific region in the SEMA domain, as an epitope. It may be any antibody or antigen-binding fragment that acts on c-Met to induce intracellular internalization and degradation of c-Met.

c-Met, a receptor for hepatocyte growth factor(HGF), may be divided into three portions: extracellular, transmembrane, and intracellular. The extracellular portion is composed of an α-subunit and a β-subunit which are linked to each other through a disulfide bond, and contains a SEMA domain responsible for binding HGF, a PSI domain (plexin-semaphorins-integrin homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region including the amino acid sequence of SEQ ID NO: 71, which corresponds to a range from amino acid residues 106 to 124 of the amino acid sequence of the SEMA domain (SEQ ID NO: 79) of c-Met protein, is a loop region between the second and the third propellers within the epitopes of the SEMA domain. The region acts as an epitope for the specific anti-c-Met antibody of the present invention.

The term "epitope" as used herein, refers to an antigenic determinant, a part of an antigen recognized by an antibody. In one embodiment, the epitope may be a region including about 5 or more contiguous amino acid residues within the SEMA domain (SEQ ID NO: 79) of c-Met protein, for instance, about 5 to about 19 contiguous amino acid residues within the amino acid sequence of SEQ ID NO: 71. For example, the epitope may be a polypeptide having about 5 to about 19 contiguous amino acids selected from among partial combinations of the amino acid sequence of SEQ ID NO: 71, wherein the polypeptide essentially includes the amino sequence of SEQ ID NO: 73 (EEPSQ) serving as an essential element for the epitope. For example, the epitope may be a polypeptide including, consisting essentially of, or consisting of the amino acid sequence of SEQ ID NO: 71, SEQ ID NO: 72, or SEQ ID NO: 73.

The epitope including the amino acid sequence of SEQ ID NO: 72 corresponds to the outermost part of the loop between the second and third propellers within the SEMA domain of a c-Met protein. The epitope including the amino acid sequence of SEQ ID NO: 73 is a site to which the antibody or antigen-binding fragment according to one embodiment most specifically binds.

Contiguous amino acids may be consecutive amino acids in the linear sequence, or contiguous in a three-dimensional configuration of the epitope without necessarily being consecutive in the linear sequence.

Thus, the anti-c-Met antibody may specifically bind to an epitope which has about 5 to about 19 contiguous amino acids selected from among partial combinations of the amino acid sequence of SEQ ID NO: 71, including SEQ ID NO: 73 as an essential element. For example, the anti-c-Met antibody may specifically bind to an epitope including the amino acid sequence of SEQ ID NO: 71, SEQ ID NO: 72, or SEQ ID NO: 73.

In one embodiment, the anti-c-Met antibody or an antigen-binding fragment thereof may comprise or consist essentially of:

at least one heavy chain complementarity determining region (CDR) selected from the group consisting of (a) a CDR-H1 comprising or consisting essentially of the amino acid sequence of SEQ ID NO: 4; (b) a CDR-H2 comprising or consisting essentially of the amino acid sequence of SEQ ID NO: 5, SEQ ID NO: 2, or an amino acid sequence having about 8-19 consecutive amino acids within SEQ ID NO: 2 including amino acid residues from the $3^{rd}$ to $10^{th}$ positions of SEQ ID NO: 2; and (c) a CDR-H3 comprising or consisting essentially of the amino acid sequence of SEQ ID NO: 6, SEQ ID NO: 85, or an amino acid sequence having about 6-13 consecutive amino acids within SEQ ID NO: 85 including amino acid residues from the $1^{st}$ to $6^{th}$ positions of SEQ ID NO: 85, or a heavy chain variable region including the at least one heavy chain complementarity determining region;

at least one light chain complementarity determining region (CDR) selected from the group consisting of (a) a CDR-L1 comprising or consisting essentially of the amino acid sequence of SEQ ID NO: 7, (b) a CDR-L2 comprising or consisting essentially of the amino acid sequence of SEQ ID NO: 8, and (c) a CDR-L3 comprising or consisting essentially of the amino acid sequence of SEQ ID NO: 9, SEQ ID NO: 15, SEQ ID NO: 86, or an amino acid sequence having 9-17 consecutive amino acids within SEQ ID NO: 89 including amino acid residues from the $1^{st}$ to $9^{th}$ positions of SEQ ID NO: 89, or a light chain variable region including the at least one light chain complementarity determining region;

a combination of the at least one heavy chain complementarity determining region and at least one light chain complementarity determining region; .or a combination of the heavy chain variable region and the light chain variable region.

Herein, the amino acid sequences of SEQ ID NOS: 4 to 9 are respectively represented by following Formulas I to VI, below:

```
Formula I
Xaa1-Xaa2-Tyr-Tyr-Met-Ser,    (SEQ ID NO: 4)
``` wherein $Xaa_1$ is absent or Pro or Ser, and $Xaa_2$ is Glu or Asp,

```
Formula II
                                    (SEQ ID NO: 5)
Arg-Asn-Xaa3-Xaa4-Asn-Gly-Xaa5-Thr,
``` wherein $Xaa_3$ is Asn or Lys, $Xaa_4$ is Ala or Val, and $Xaa_5$ is Asn or Thr,

```
Formula III
Asp-Asn-Trp-Leu-Xaa6-Tyr,    (SEQ ID NO: 6)
``` wherein $Xaa_6$ is Ser or Thr,

```
Formula IV
                                    (SEQ ID NO: 7)
Lys-Ser-Ser-Xaa7-Ser-Leu-Leu-Ala-Xaa8-Gly-Asn-
Xaa9-Xaa10-Asn-Tyr-Leu-Ala
``` wherein $Xaa_7$ is His, Arg, Gln, or Lys, $Xaa_8$ is Ser or Trp, $Xaa_9$ is His or Gln, and $Xaa_{10}$ is Lys or Asn,

```
Formula V
Trp-Xaa11-Ser-Xaa12-Arg-Val-Xaa13 (SEQ ID NO: 8)
``` wherein $Xaa_{11}$ is Ala or Gly, $Xaa_{12}$ is Thr or Lys, and $Xaa_{13}$ is Ser or Pro, and

```
Formula VI
                                    (SEQ ID NO: 9)
Xaa14-Gln-Ser-Tyr-Ser-Xaa15-Pro-Xaa16-Thr
``` wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may comprise or consist essentially of an amino acid sequence selected from the group consisting of SEQ ID NOS: 1, 22, 23, and 24. The CDR-H2 may comprise or consist essentially of an amino acid sequence selected from the group consisting of SEQ ID NOS: 2, 25, and 26. The CDR-H3 may comprise or consist essentially of an amino acid sequence selected from the group consisting of SEQ ID NOS: 3, 27, 28, and 85.

The CDR-L1 may comprise or consist essentially of an amino acid sequence selected from the group consisting of SEQ ID NOS: 10, 29, 30, 31, 32, 33, and 106. The CDR-L2 may comprise or consist essentially of an amino acid sequence selected from the group consisting of SEQ ID NOS: 11, 34, 35, and 36. The CDR-L3 may comprise or consist essentially of an amino acid sequence selected from the group consisting of SEQ ID NOS: 12, 13, 14, 15, 16, 37, 86, and 89.

In another embodiment, the antibody or antigen-binding fragment may include a heavy chain variable region comprising a polypeptide (CDR-H1) comprising or consisting essentially of an amino acid sequence selected from the group consisting of SEQ ID NOS: 1, 22, 23, and 24, a polypeptide (CDR-H2) comprising or consisting essentially of an amino acid sequence selected from the group consisting of SEQ ID NOS: 2, 25, and 26, and a polypeptide (CDR-H3) comprising or consisting essentially of an amino acid sequence selected from the group consisting of SEQ ID NOS: 3, 27, 28, and 85; and a light chain variable region comprising a polypeptide (CDR-L1) comprising or consisting essentially of an amino acid sequence selected from the group consisting of SEQ ID NOS: 10, 29, 30, 31, 32, 33 and 106, a polypeptide (CDR-L2) comprising or consisting essentially of an amino acid sequence selected from the group consisting of SEQ ID NOS: 11, 34, 35, and 36, and a polypeptide (CDR-L3) comprising or consisting essentially of an amino acid sequence selected from the group consisting of SEQ ID NOS 12, 13, 14, 15, 16, 37, 86, and 89.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but variable regions still have animal-derived amino acid sequences, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

An important consideration in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2(γ2), gamma 3(γ3), gamma 4(γ4), alpha 1(α1), or alpha 2(α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody or an antigen-binding fragment thereof may be modified by the deletion, insertion, addition, or substitution of at least one amino acid residue on the amino acid sequence of the hinge region so that it exhibit enhanced antigen-binding efficiency. For example, the antibody may include a hinge region including the amino acid sequence of SEQ ID NO: 100(U7-HC6), 101(U6-HC7), 102(U3-HC9), 103(U6-HC8), or 104(U8-HC5), or a hinge region including the amino acid sequence of SEQ ID NO: 105 (non-modified human hinge). In particular, the hinge region has the amino acid sequence of SEQ ID NO: 100 or 101.

In one embodiment, the anti-c-Met antibody or antigen-binding fragment may include a variable region of the heavy chain comprising or consisting essentially of the amino acid sequence of SEQ ID NO: 17, 74, 87, 90, 91, 92, 93, or 94, a variable region of the light chain comprising or consisting essentially of the amino acid sequence of SEQ ID NO: 162, 18, 19, 20, 21, 75, 88, 95, 96, 97, 98, 99, or 107, or a combination thereof.

In one embodiment, the anti-c-Met antibody may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0047698, the disclosure of which is incorporated in its entirety herein by reference). The anti-c-Met antibody may include all the antibodies defined in Korean Patent Publication No. 2011-0047698.

In the anti-c-Met antibody, the rest portion of the light chain and the heavy chain portion excluding the CDRs, the light chain variable region, and the heavy chain variable region as defined above, that is the light chain constant region and the heavy chain constant region, may be those from any subtype of immunoglobulin (e.g., IgA, IgD, IgE, IgG (IgG1, IgG2, IgG3, IgG4), IgM, and the like).

By way of further example, the anti-c-Met antibody or the antibody fragment may include:
a heavy chain including the amino acid sequence selected from the group consisting of the amino acid sequence of SEQ ID NO: 62 (wherein the amino acid sequence from amino acid residues from the 1$^{st}$ to 17$^{th}$ positions is a signal peptide), or the amino acid sequence from the 18$^{th}$ to 462$^{nd}$ positions of SEQ ID NO: 62, the amino acid sequence of SEQ ID NO: 64 (wherein the amino acid sequence from the 1$^{st}$ to 17$^{th}$ positions is a signal peptide), the amino acid sequence from the 18$^{th}$ to 461$^{st}$ positions of SEQ ID NO: 64, the amino acid sequence of SEQ ID NO: 66 (wherein the amino acid sequence from the 1$^{st}$ to 17$^{th}$ positions is a signal peptide), and the amino acid sequence from the 18$^{th}$ to 460$^{th}$ positions of SEQ ID NO: 66; and a light chain including the amino acid sequence selected from the group consisting of the amino acid sequence of SEQ ID NO: 68 (wherein the amino acid sequence from the 1$^{st}$ to 20$^{th}$ positions is a signal peptide), the amino acid sequence from the 21$^{st}$ to 240$^{th}$ positions of SEQ ID NO: 68, the amino acid sequence of SEQ ID NO: 70 (wherein the amino acid sequence from the 1$^{st}$ to 20$^{th}$ positions is a signal peptide), the amino acid sequence from the 21$^{st}$ to 240$^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the 18$^{th}$ to 462$^{nd}$ positions of SEQ ID NO: 62 and a light chain including the amino acid sequence of SEQ ID NO: 68 or the amino acid sequence from the 21$^{st}$ to 240$^{th}$ positions of SEQ ID NO: 68;

an antibody including a heavy chain including the amino acid sequence of SEQ ID NO: 64 or the amino acid sequence from the 18$^{th}$ to 461$^{st}$ positions of SEQ ID NO: 64 and a light chain including the amino acid sequence of SEQ ID NO: 68 or the amino acid sequence from the 21$^{st}$ to 240$^{th}$ positions of SEQ ID NO: 68;

an antibody including a heavy chain including the amino acid sequence of SEQ ID NO: 66 or the amino acid sequence from the 18$^{th}$ to 460$^{th}$ positions of SEQ ID NO: 66 and a light chain including the amino acid sequence of SEQ ID NO: 68 or the amino acid sequence from the 21$^{st}$ to 240$^{th}$ positions of SEQ ID NO: 68;

an antibody including a heavy chain including the amino acid sequence of SEQ ID NO: 62 or the amino acid sequence from the 18$^{th}$ to 462$^{nd}$ positions of SEQ ID NO: 62 and a light chain including the amino acid sequence of SEQ ID NO: 70 or the amino acid sequence from the 21$^{st}$ to 240$^{th}$ positions of SEQ ID NO: 70;

an antibody including a heavy chain including the amino acid sequence of SEQ ID NO: 64 or the amino acid sequence from the 18$^{th}$ to 461$^{st}$ positions of SEQ ID NO: 64 and a light chain including the amino acid sequence of SEQ ID NO: 70 or the amino acid sequence from the 21$^{st}$ to 240$^{th}$ positions of SEQ ID NO: 70;

an antibody including a heavy chain including the amino acid sequence of SEQ ID NO: 66 or the amino acid sequence from the 18$^{th}$ to 460$^{th}$ positions of SEQ ID NO: 66 and a light chain including the amino acid sequence of SEQ ID NO: 70 or the amino acid sequence from the 21$^{st}$ to 240$^{th}$ positions of SEQ ID NO: 70;

an antibody including a heavy chain including the amino acid sequence of SEQ ID NO: 62 or the amino acid sequence from the 18$^{th}$ to 462$^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the 18$^{th}$ to 461$^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the 18$^{th}$ to 460$^{th}$ positions of SEQ ID NO: 66 and a light chain including the amino acid sequence of SEQ ID NO: 108.

According to an embodiment, the anti-c-Met antibody may include a heavy chain including the amino acid sequence from the 18$^{th}$ to 460$^{th}$ positions of SEQ ID NO: 66 and a light chain including the sequence from the 21$^{st}$ to 240$^{th}$ positions of SEQ ID NO: 68, or a heavy chain including the amino acid sequence from the 18$^{th}$ to 460$^{th}$ positions of SEQ ID NO: 66 and a light chain including the sequence of SEQ ID NO: 108.

The polypeptide of SEQ ID NO: 70 is a light chain including human kappa (κ) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 of SEQ ID NO: 108 (corresponding to position 52 of SEQ ID NO: 68, which corresponds to position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, Akt phosphorylation inhibition, and the like.

The anti HER2 antibodies, anti c-Met antibodies, the anti-c-Met/anti-HER2 bispecific antibodies, and antigen-binding fragments thereof may be mouse-derived antibodies, mouse-human chimeric antibodies, humanized antibodies, or human antibodies. The antibodies or antigen-binding fragments thereof may be isolated from a living body or non-naturally occurring. The antibodies or antigen-binding fragments thereof may be synthetic (artificially synthetic) or recombinant. The antibodies or antigen-binding fragments thereof may be monoclonal.

The anti-c-Met/anti-HER2 bispecific antibody can not only inhibit the activity of c-Met and HER2 by the internalization and degradation activity of anti-c-Met antibody but also fundamentally block them by reducing the total amounts of c-Met and HER2 by the degradation thereof. Accordingly, the anti-c-Met/anti-HER2 bispecific antibody can obtain efficient effects even when applied to patients who have developed resistance against pre-existing HER2 targeting drugs such as anti-HER2 antibodies.

Another embodiment provides a pharmaceutical composition including the anti-HER2 antibody or an antigen-binding fragment thereof as an active ingredient. Another embodiment provides a pharmaceutical composition including the anti-c-Met/anti-HER2 bispecific antibody as an active ingredient.

In particular, another embodiment provides a pharmaceutical composition for preventing and/or treating a cancer including the anti-HER2 antibody or an antigen-binding fragment thereof as an active ingredient. Another embodiment provides a pharmaceutical composition for preventing and/or treating a cancer including the anti-c-Met/anti-HER2 bispecific antibody as an active ingredient.

Another embodiment provides a method of prevention and/or treatment a cancer, including administering a pharmaceutical effective amount of the anti-HER2 antibody or an antigen-binding fragment thereof to a patient in need of the prevention and/or treatment of the cancer. Another embodiment provides a method of prevention and/or treatment of a cancer, including administering a pharmaceutical effective amount of the anti-c-Met/anti-HER2 bispecific antibody to a patient in need of the prevention and/or treatment of the cancer. The method of prevention and/or treatment a cancer may further comprises a step of identifying the patient in need of the prevention and/or treatment of the cancer, prior to the step of administering.

The cancer may be any cancer associated with overexpression and/or abnormal activation of c-Met and/or HER2. The cancer may be any cancer in which HER2 and/or c-Met possibly plays an important role for proliferation, invasion, and metastasis, including the resistant cancers to HER2 therapy. The cancer may be a solid cancer or hematological cancer and for instance, may be, but not limited to, one or more selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, and the like. In particular, the cancer may be cancer having resistance against pre-existing anticancer drugs, for example, antagonists against HER2 (e.g., anti-HER2 antibody) and/or antagonists against c-Met (e.g., anti-c-Met antibody). The prevention and/or treatment effects of the cancers may include effects of not only suppressing the growth of the cancer cells but also suppressing deterioration of cancers due to migration, invasion, and/or metastasis thereof. Therefore, the curable cancers may include both primary cancers and metastatic cancers. Thus, the pharmaceutical composition or method may be for preventing and/or treating cancer metastasis.

The anti-c-Met/anti-HER2 bispecific antibody recognizes both c-Met and HER2, which commonly possess mechanisms of cancer generation such as cancer cell proliferation, cancer cell migration, cancer cell invasion, angiogenesis, cancer metastasis, inhibition of apoptosis, and the like, thereby exhibiting a more excellent anticancer effect. Such anticancer effect may include not only an effect of inhibition of cancer cell proliferation but also inhibition of cancer metastasis and/or invasion.

In the pharmaceutical composition or method, the pharmaceutically effective amount of the anti-HER2 antibody or an antigen-binding fragment thereof or the anti-c-Met/anti-HER2 bispecific antibody may be administered along with at least one additive selected from the group consisting of a pharmaceutically acceptable carriers, diluents, and excipients.

The pharmaceutically acceptable carrier to be included in the composition may be those commonly used for the formulation of antibodies, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The pharmaceutical composition may further include one or more selected from the group consisting of a lubricant, a wetting agent, a sweetener, a flavor enhancer, an emulsifying agent, a suspension agent, and preservative.

The pharmaceutical composition, or the anti-HER2 antibody or an antigen-binding fragment thereof, or the anti-c-Met/anti-HER2 bispecific antibody or an antigen-binding fragment thereof may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the compositions may be administered using an optional device that enables an active substance to be delivered to target cells.

A suitable dosage of the pharmaceutical composition, or the anti-HER2 antibody or an antigen-binding fragment thereof, or the anti-c-Met/anti-HER2 bispecific antibody or an antigen-binding fragment thereof may be prescribed in a variety of ways, depending on factors such as formulation methods, administration methods, age of patients, body weight, gender, pathologic conditions, diets, administration time, administration route, excretion speed, and reaction sensitivity. A desirable dosage of the pharmaceutical composition, the anti-HER2 antibody, the anti-c-Met/anti-HER2 bispecific antibody, or antigen-binding fragment thereof may be in the range of about 0.001 to 100 mg/kg for an adult. For example, the suitable dosage of the pharmaceutical composition, the anti-HER2 antibody, or the anti-c-Met/anti-HER2 bispecific antibody, or an antigen-binding fragment thereof may be about 0.001 to about 1000 mg/kg, about 0.01 to about 100 mg/kg, or 0.1 to 50 mg/kg, per a day, but not be limited thereto. The term "pharmaceutically effective amount" used herein refers to an amount of the active ingredient (i.e., the anti-HER2 antibody or an antigen-binding fragment thereof, or the anti-c-Met/anti-HER2 bispecific antibody) exhibiting effects in preventing or treating cancer, and may be properly determined in a variety of ways, depending on factors such as formulation methods, administration methods, age of patients, body weight, gender, pathologic conditions, diets, administration time, administration route, excretion speed, and reaction sensitivity.

The pharmaceutical composition, the anti-HER2 antibody, or the anti-c-Met/anti-HER2 bispecific antibody, or an antigen-binding fragment thereof may be formulated with a pharmaceutically acceptable carrier and/or excipient into a unit or a multiple dosage form by a method easily carried out by a skilled person in the pertinent art. The dosage form may be a solution in oil or an aqueous medium, a suspension, syrup, an emulsifying solution, an extract, powder, granules, a tablet, or a capsule, and may further include a dispersing or a stabilizing agent.

In addition, the pharmaceutical composition, the anti-HER2 antibody, or the anti-c-Met/anti-HER2 bispecific antibody, or an antigen-binding fragment thereof may be administered as an individual drug, or together with other drugs, and may be administered sequentially or simultaneously with pre-existing drugs.

Since the pharmaceutical composition includes an antibody or an antigen binding fragment thereof, it may be formulated as an immunoliposome. The liposome containing an antibody may be prepared using a well-known method in the pertinent art. The immunoliposome is a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide exchange reaction. A chemical drug such as doxorubicin may be additionally included in the liposome.

The subject to which the pharmaceutical composition or the antibody or antigen-binding fragment thereof is administered or the patient to which the prevention and/or treatment method is applied may be mammals, for example, primates such as humans and monkeys, or rodents such as rats and mice, but are not be limited thereto. The subject or the patient may be a cancer patient having resistance against pre-existing anticancer drugs, for example, antagonists against the target cell membrane proteins (e.g., HER2).

Another embodiment provides a polynucleotide encoding a polypeptide including one amino acid sequence or a combination of two or more amino acid sequences selected from the group consisting of SEQ ID NOs: 109 to 131. In a particular embodiment, the polynucleotide may encode a polypeptide including the amino acid sequence selected from the group consisting of SEQ ID NOs: 132 to 136, a polypeptide including the amino acid sequence selected from the group consisting of SEQ ID NOs: 137 to 141, or a combination thereof. In an embodiment, the polynucleotide may include the nucleotide sequence selected from the group consisting of SEQ ID NOs: 142 to 151. Another embodiment provides a recombinant vector including the polynucleotide. Another embodiment provides a recombinant cell transfected with the recombinant vector.

The term "vector" used herein refers to a means for expressing a target gene in a host cell. For example, it includes a plasmid vector, a cosmid vector, and a virus vector such as a bacteriophage vector, an adenovirus vector, a retrovirus vector and an adeno-associated virus vector. Suitable recombinant vectors may be constructed by manipulating plasmids often used in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, and the like), a phage (for example, λgt4λB, λ-Charon, λΔz1, M13, and the like), or a virus (for example, SV40, and the like), but not be limited thereto.

In the recombinant vector, the polynucleotides may be operatively linked to a promoter. The term "operatively linked" used herein refers to a functional linkage between a nucleotide expression regulating sequence (for example, a promoter sequence) and other nucleotide sequences. Thus, the regulating sequence may regulate the transcription and/or translation of the other nucleotide sequences by being operatively linked.

The recombinant vector may be constructed for cloning or expression. The expression vector may be any ordinary vectors known in the pertinent art for expressing an exogenous protein in plants, animals, or microorganisms. The recombinant vector may be constructed using various methods known in the art.

The recombinant vector may be constructed using a prokaryotic cell or a eukaryotic cell as a host. For example, when a prokaryotic cell is used as a host cell, the expression vector used generally includes a strong promoter capable of initiating transcription (for example, pL$^\lambda$ promoter, CMV promoter, trp promoter, lac promoter, tac promoter, T7 promoter, and the like), a ribosome binding site for initiating translation, and a transcription/translation termination sequence. When a eukaryotic cell is used as a host cell, the vector used generally includes the origin of replication acting in the eukaryotic cell, for example, a f1 replication origin, a SV40 replication origin, a pMB1 replication origin, an adeno replication origin, an AAV replication origin, or a BBV replication origin, but is not limited thereto. A promoter in an expression vector for a eukaryotic host cell may be a promoter derived from the genomes of mammalian cells (for example, a metallothionein promoter, and the like) or a promoter derived from mammalian viruses (for example, an adenovirus late promoter, a vaccinia virus 7.5K promoter, a SV40 promoter, a cytomegalovirus promoter, a tk promoter of HSV, and the like). A transcription termination sequence in an expression vector for a eukaryotic host cell may be, in general, a polyadenylation sequence.

The recombinant cell may be one obtained by transfecting the recombinant vector into a suitable host cell. Any host cells known in the pertinent art to enable stable and continuous cloning or expression of the recombinant vector may be used as the hose cell. Suitable prokaryotic host cells may be one or more selected from *E. coli* JM109, *E. coli* BL21, *E. coli* RR1, *E. coli* LE392, *E. coli* B, *E. coli* X 1776, *E. coli* W3110, *Bacillus* species strains such as *Bacillus subtillis*, or *Bacillus thuringiensis*, intestinal bacteria and strains such as *Salmonella typhymurum, Serratia marcescens*, and various *Pseudomonas* species. Suitable eukaryotic host cells to be transformed may be one or more selected from yeasts, such as *Saccharomyces cerevisiae*, insect cells, plant cells, and animal cells, for example, Sp2/0, Chinese hamster ovary (CHO) K1, CHO DG44, PER.C6, W138, BHK, COS-7, 293, HepG2, Huh7, 3T3, RIN, and MDCK cell lines, but not be limited thereto.

The polynucleotide or the recombinant vector including the same may be transferred (transfected) into a host cell by using known transfer methods. Suitable transfer methods for prokaryotic host cells may include a method using CaCl$_2$ and electroporation. Suitable transfer methods for eukaryotic host cells may include microinjection, calcium phosphate precipitation, electroporation, liposome-mediated transfection, and gene bombardment, but are not limited thereto.

A transformed host cell may be selected using a phenotype expressed by a selected marker by any methods known in the art. For example, if the selected marker is a gene that is resistant to a specific antibiotic, a transformant may be easily selected by being cultured in a medium including the antibiotic.

Another embodiment provides a method of preparing the polypeptide, the anti-HER2 antibody or an antigen-binding fragment thereof, or the anti-c-Met/anti-HER2 bispecific antibody or an antigen-binding fragment thereof, comprising expressing a polynucleotide encoding the polypeptide, the anti-HER2 antibody or an antigen-binding fragment thereof, or the anti-c-Met/anti-HER2 bispecific antibody or an antigen-binding fragment thereof in a cell (for example, culturing a cell including the polynucleotide encoding the polypeptide, the anti-HER2 antibody or an antigen-binding fragment thereof, or the anti-c-Met/anti-HER2 bispecific antibody or an antigen-binding fragment thereof, under the conditions allowing the expression).

Herceptin™ is a representative targeting therapeutic agent specifically recognizes HER2, which is a representative target largely expressed in cancer cells. Herceptin™ induces overexpression and activation of c-Met, leading to acquiring a resistance to the agent, thereby reducing therapeutic effects of the agent. In this disclosure, it is revealed that a bispecific antibody simultaneously recognizing cMet and HER2 can inhibit overexpression and/or activation of c-Met, which is a cause of a drug resistance, to previously block a signal transduction, thereby preventing generation of resistance and exhibiting excellent anticancer effects even on cancer cells having a resistance. The anti-cMet/anti-HER2 bispecific antibody provided herein simultaneously recognizes c-Met and HER2, which commonly possess mechanisms of cancer generation such as cancer cell proliferation, cancer cell migration, cancer cell invasion, angiogenesis, cancer metastasis, inhibition of apoptosis, and the like, thereby exhibiting more excellent anticancer effect compared to pre-existing single targeting agent, and exhibiting anticancer effect even on a cancer on which the pre-existing anticancer agent cannot exhibit its anticancer effect.

EXAMPLES

Hereafter, the present invention will be described in detail by examples.

The following examples are intended merely to illustrate the invention and are not construed to restrict the invention.

Reference Example 1

Construction of Anti-c-Met Antibody 1.1. Production of "AbF46", a Mouse Antibody to c-Met
1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1\times10^8$ cells) were mixed with myeloma cells (Sp2/0) ($1\times10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1\sim2\times10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with a filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Reference Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (program available at National Center for Biotechnology Information's website) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of 5×10$^5$ cells/ml, and after 24 hours, when the cell number reached to 1×10$^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% CO$_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFv Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker including the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 2, below.

TABLE 2

| CDR | Amino Acid Sequence |
|---|---|
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 3 and were converted into IgG forms. Four antibodies which were respectively produced from clones L3-1, L3-2, L3-3, and L3-5 were used in the subsequent experiments.

TABLE 3

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |

TABLE 3-continued

| Clone | Library constructed | CDR Sequence |
|---|---|---|
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain including the heavy chain variable region of huAbF46-H4-A1, U6-HC7 hinge, and the constant region of human IgG1 constant region, and a light chain including the light chain variable region of huAbF46-H4-A1 and human kappa constant region. The antibody huAbF46-H4-A1 (IgG2 hinge) was composed of a heavy chain including a heavy chain variable region, a human IgG2 hinge region, and a human IgG1 constant region, and a light chain including the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain including the light variable region of huAbF46-H4-A1 and a human kappa constant region. The histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (U6-HC7) and huAbF46-H4-A1 (IgG2 Fc) were selected for the following examples, and name as L3-1Y U6-HC7 and L3-1Y-IgG2, respectively.

Example 1

Preparation of Anti-HER2 scFv

Antibodies binding to Her2 were selected by panning and screening for a phage display scFv library (reference paper: A human scFv antibody generation pipeline for proteome research. 2010, J. Biotechnol., 152, pp. 159-170, which is incorporated herein by reference) using human HER2 (GenBank Accession Nos. NP_004439), referring to the experimental method in the reference paper.

As the results, five anti-HER2 scFv fragments were selected, and named as 41-B11, 41-C6, 41-E1, 44-C12, and 44-H4, respectively.

The gene sequences of the selected anti-HER2 scFv fragments were amplified using a thermocycler (GeneAmp PCR System 9700, Applied Biosystem). The nucleotide sequences of the used primers were summarized in Table 5:

TABLE 5

| Anti-HER2 scFv | Forward primer | Reverse primer |
| --- | --- | --- |
| 41-B11 | GGTTCCGGAGGCGGCGGATCCGAGGAGGGATCGAACCCTTCTCGAGTCAA TGCAGCTGGTGCAGTC (SEQ ID NO: 152) | CCTAGGACGGTCAACTTGGTC (SEQ ID NO: 153) |
| 41-C6 | GGTTCCGGAGGCGGCGGATCCCAGAAGGGATCGAACCCTTCTCGAGTCAA TCCAGCTGGTACAATCTGG (SEQ ID NO: 154) | CCTAGGACGGTCAGCTTGGT (SEQ ID NO: 155) |
| 41-E1 | GGTTCCGGAGGCGGCGGATCCGAGGAGGGATCGAACCCTTCTCGAGTCAA TGCAGCTGGTGGAGTC (SEQ ID NO: 156) | CGTAGGACGGTCAGCTTGGT (SEQ ID NO: 157) |
| 44-C12 | GGTTCCGGAGGCGGCGGATCCGAAGAGGGATCGAACCCTTCTCGAGTCAA TGCAGCTGGTGCAGTCT (SEQ ID NO: 158) | CGTAGGACGGTCAGCTTGGT (SEQ ID NO: 159) |
| 44-H4 | GGTTCCGGAGGCGGCGGATCCGAGGAGGGATCGAACCCTTCTCGAGTCAA TGCAGCTGGTGCAGTC (SEQ ID NO: 160) | CCTAGGACGGTCACCTTGGT (SEQ ID NO: 161) |

The PCR products obtained from the reactions were purified using QIAquick Multiwell PCR Purification kit (Qiagen) according to the manufacturer's protocol.

The purified PCR products were cloned and then, subjected to DNA sequencing according to a known method. Amino acid and nucleotide sequences of CDRs (see Tables 6 and 7) and variable regions (see Tables 8 and 9) of anti-HER2 antibody were identified.

TABLE 6

| Antibody | CDR-H1 | CDR-H2 | CDR-H3 |
| --- | --- | --- | --- |
| 41-B11 | SYWIG (SEQ ID NO: 109) | IIYPGDSDTRYSPSFQG (SEQ ID NO: 112) | RHYYDSSGYSYFPDY (SEQ ID NO: 115) |
| 41-C6 | SYWIG (SEQ ID NO: 109) | IIYPGDSDTRYSPSFQG (SEQ ID NO: 112) | RLSVAAAGTGGYNWFDP (SEQ ID NO: 116) |
| 41-E1 | DYAMS (SEQ ID NO: 110) | FIRSKAYGGTTEYAASVKG (SEQ ID NO: 113) | RDLYPAMAEY (SEQ ID NO: 117) |
| 44-C12 | SYAIS (SEQ ID NO: 111) | GIIPIFGTANYAQKFQG (SEQ ID NO: 114) | RDSGYSYGYPMNYYYYM DV (SEQ ID NO: 118) |

TABLE 6-continued

| Antibody | CDR-H1 | CDR-H2 | CDR-H3 |
| --- | --- | --- | --- |
| 44-H4 | SYWIG (SEQ ID NO: 109) | IIYPGDSDTRYSPSFQG (SEQ ID NO: 112) | RLVVGANPPTYYFDY (SEQ ID NO: 119) |

TABLE 7

| Antibody | CDR-L1 | CDR-L2 | CDR-L3 |
| --- | --- | --- | --- |
| 41-B11 | GLSSGSVSTSYYPS (SEQ ID NO: 120) | STNTRSSGVPD (SEQ ID NO: 124) | VLYMGSGIWV (SEQ ID NO: 127) |
| 41-C6 | GLTSGSVSTSYYPS (SEQ ID NO: 121) | STNTRSSGVPD (SEQ ID NO: 124) | MLYLGGGISV (SEQ ID NO: 128) |
| 41-E1 | TRSSGSIDSNFVQ (SEQ ID NO: 122) | DDNQRPSGVPD (SEQ ID NO: 125) | QSYDSNNQV (SEQ ID NO: 129) |
| 44-C12 | GLSSGSVSPTYYPS (SEQ ID NO: 123) | RTNIRSSGVPD (SEQ ID NO: 126) | LLYMGSGVSL (SEQ ID NO: 130) |
| 44-H4 | GLSSGSVSTSYYPS (SEQ ID NO: 120) | STNTRSSGVPD (SEQ ID NO: 124) | VLYMGSGISL (SEQ ID NO: 131) |

TABLE 8

| Antibody | Amino acid sequence of heavy chain variable region of anti-HER2 antibody | Nucleotide sequence of heavy chain variable region of anti-HER2 antibody |
| --- | --- | --- |
| 41-B11 | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARHYYDSSGYSYFPDYWGQGTLVTVSS (SEQ ID NO: 132) | GAGGTGCAGCTGGTGCAGTCTGGAGCAGAGGTGAAAAAGCCCGGGGAGTCTCTGAAGATCTCCTGTAAGGGTTCTGGATACAGCTTTACCAGCTACTGGATCGGCTGGGTGCGCCAGATGCCCGGGAAAGGCCTGGAGTGGATGGGGATCATCTATCCTGGTGACTCTGATACCAGATACAGCCCGTCCTTCCAAGGCCAGGTCACCATCTCAGCCGACAAGTCCATCAGCACCGCCTACCTGCAGTGGAGCAGCCTGAAGGCCTCGGACACCGCCATGTATTACTGTGCGAGACATTACTATGATAGTAGTGGTTATTCCTACTTTCCGGACTACTGGGGCCAGGGAACCCTGGTCACCGTCTCCTCA (SEQ ID NO: 142) |
| 41-C6 | QIQLVQSGAEVKKPGESLKISCRGSGYSFTSYWIGWVRQMPGKGLEWMGIIYPGDSDTRYSPSFQGQVTISADKSISTAYLQWSSLKASDTAMYYCARLSVAAAGTGGYNWFDPWGQGTLVTVSS (SEQ ID NO: 133) | CAGATCCAGCTGGTACAATCTGGAGCAGAGGTGAAAAAGCCCGGGGAGTCTCTGAAGATCTCCTGTAGGGGTTCTGGATACAGCTTTACCAGCTACTGGATCGGCTGGGTGCGCCAGATGCCCGGGAAAGGCCTGGAGTGGATGGGGATCATCTATCCTGGTGACTCTGATACCAGATACAGCCCGTCCTTCCAAGGCCAGGTCACCATCTCAGCCGACAAGTCCATCAGCACCGCCTACCTGCAGTGGAGCAGCCTGAAGGCCTCGGACACCGCCATGTATTACTGTGCGAGACTCAGCGTAGCAGCAGCTGGTACGGGGGGGTACAACTGGTTCGACCCCTGGGGCCAGGGAACCCTGGTCACCGTCTCCTCA (SEQ ID NO: 143) |
| 41-E1 | EVQLVESGGGLVKPGRSLRLSCTASGFTFGDYAMSWFRQAPGKGLEWVGFIRSKAYGGTTEYAASVKGRFTISRDDSKSIAYLQMNSLKTEDTAVYYCTRDLYPAMAEYWGQGTLVTVSS (SEQ ID NO: 134) | GAGGTGCAGCTGGTGGAGTCTGGGGGAGGCTTGGTAAAGCCAGGGCGGTCCCTGAGACTCTCCTGTACAGCTTCTGGATTCACCTTTGGTGATTATGCTATGAGCTGGTTCCGCCAGGCTCCAGGGAAGGGGCTGGAGTGGGTAGGTTTCATTAGAAGCAAAGCTTATGGTGGGACAACAGAATACGCCGCGTCTGTGAAAGGCAGATTCACCATCTCAAGAGATGATTCCAAAAGCATCGCCTATCTGCAAATGAACAGCCTGAAAACCGAGGACACAGCCGTGTATTACTGTACTAG |

TABLE 8-continued

| Antibody | Amino acid sequence of heavy chain variable region of anti-HER2 antibody | Nucleotide sequence of heavy chain variable region of anti-HER2 antibody |
| --- | --- | --- |
| | | AGATTTATACCCAGCTATGGCTGAGTA<br>CTGGGGCCAGGGAACCCTGGTCACCGT<br>CTCCTCA<br>(SEQ ID NO: 144) |
| 44-C12 | EVQLVQSGAEVKKPGSSVKVSCKASG<br>GTFSSYAISWVRQAPGQGLEWMGGII<br>PIFGTANYAQKFQGRVTITADKSTSTA<br>YMELSSLRSEDTAVYYCARDSGYSYG<br>YPMNYYYYYMDVWGKGTTVTVSS<br>(SEQ ID NO: 135) | GAAGTGCAGCTGGTGCAGTCTGGGGCT<br>GAGGTGAAGAAGCCTGGGTCCTCGGTG<br>AAGGTCTCCTGCAAGGCTTCTGGAGGC<br>ACCTTCAGCAGCTATGCTATCAGCTGG<br>GTGCGACAGGCCCCTGGACAAGGGCTT<br>GAGTGGATGGGAGGGATCATCCCTATC<br>TTTGGTACAGCAAACTACGCACAGAAG<br>TTCCAGGGCAGAGTCACGATTACCGCG<br>GACAAATCCACGAGCACAGCCTACATG<br>GAGCTGAGCAGCCTGAGATCTGAGGAC<br>ACGGCCGTGTATTACTGTGCGAGAGAT<br>TCGGGATACAGCTATGGTTACCCTATG<br>AATTACTACTACTACTACATGGACGTCT<br>GGGGCAAAGGGACCACGGTCACCGTCT<br>CCTCA<br>(SEQ ID NO: 145) |
| 44-H4 | EVQLVQSGAEVKKPGESLKISCKGSG<br>YSFTSYWIGWVRQMPGKGLEWMGII<br>YPGDSDTRYSPSFQGQVTISADKSIST<br>AYLQWSSLKASDTAMYYCARLVVGA<br>NPPTYYFDYWGQGTLVTVSS<br>(SEQ ID NO: 136) | GAGGTGCAGCTGGTGCAGTCTGGAGCA<br>GAGGTGAAAAAGCCCGGGGAGTCTCTG<br>AAGATCTCCTGTAAGGGTTCTGGATAC<br>AGCTTTACCAGCTACTGGATCGGCTGG<br>GTGCGCCAGATGCCCGGGAAAGGCCTG<br>GAGTGGATGGGGATCATCTATCCTGGT<br>GACTCTGATACCAGATACAGCCCGTCC<br>TTCCAAGGCCAGGTCACCATCTCAGCC<br>GACAAGTCCATCAGCACCGCCTACCTG<br>CAGTGGAGCAGCCTGAAGGCCTCGGAC<br>ACCGCCATGTATTACTGTGCGAGACTC<br>GTAGTGGGAGCTAACCCCCCAACGTAC<br>TACTTTGACTACTGGGGCCAGGGAACC<br>CTGGTCACCGTCTCCTCA<br>(SEQ ID NO: 146) |

TABLE 9

| Antibody | Amino acid sequence of light chain variable region of anti-HER2 antibody | Nucleotide sequence of light chain variable region of anti-HER2 antibody |
| --- | --- | --- |
| 41-B11 | QTVVTQEPSFSVSPGGTVTLTCGLSSG<br>SVSTSYYPSWYQQTPGQAPRTLIYSTN<br>TRSSGVPDRFSGSILGNKAALTITGAQ<br>ADDESDYYCVLYMGSGIWVFGGGTK<br>LTVLG<br>(SEQ ID NO: 137) | CAGACTGTGGTGACCCAGGAGCCATCG<br>TTCTCAGTGTCCCCTGGAGGGACAGTC<br>ACACTCACTTGTGGCTTGAGCTCTGGCT<br>CAGTCTCTACTAGTTACTACCCCAGCTG<br>GTACCAGCAGACCCCAGGCCAGGCTCC<br>ACGCACGCTCATCTACAGCACAAACAC<br>TCGCTCTTCTGGGGTCCCTGATCGCTTC<br>TCTGGCTCCATCCTTGGGAACAAAGCT<br>GCCCTCACCATCACGGGGGCCCAGGCA<br>GATGATGAATCTGATTATTACTGTGTGC<br>TGTATATGGGTAGTGGCATTTGGGTGTT<br>CGGCGGAGGGACCAAGTTGACCGTCCT<br>AGGT<br>(SEQ ID NO: 147) |
| 41-C6 | QTVVTQEPSSSVSPGGTVTLTCGLTSG<br>SVSTSYYPSWYQQTPGQAPRTLIYSTN<br>TRSSGVPDRFSGSILGNKAALTITGAQ<br>ADDESDYYCMLYLGGGISVFGGGTKL<br>TVLG<br>(SEQ ID NO: 138) | CAGACTGTGGTGACCCAGGAGCCATCG<br>TCCTCAGTGTCCCCTGGAGGGACAGTC<br>ACACTCACTTGTGGCTTGACCTCTGGCT<br>CAGTCTCTACTAGTTACTACCCCAGCTG<br>GTACCAGCAGACCCCAGGCCAGGCTCC<br>ACGCACGCTCATCTACAGCACAAACAC<br>TCGCTCTTCTGGGGTCCCTGATCGCTTC<br>TCTGGCTCCATCCTTGGGAACAAAGCT<br>GCCCTCACCATCACGGGGGCCCAGGCA |

TABLE 9-continued

| Antibody | Amino acid sequence of light chain variable region of anti-HER2 antibody | Nucleotide sequence of light chain variable region of anti-HER2 antibody |
|---|---|---|
| | | GATGATGAATCTGATTATTACTGTATGC<br>TATATTTGGGTGGTGGCATTTCGGTATT<br>CGGCGGAGGGACCAAGCTGACCGTCCT<br>AGGT<br>(SEQ ID NO: 148) |
| 41-E1 | QPVLTQPHSVSESPGKTVTISCTRSSGS<br>IDSNFVQWYQQRPGSSPTTVIYDDNQ<br>RPSGVPDRFSGSIDSSSNSASLTISGLKI<br>EDEADYYCQSYDSNNQVFGGGTKLT<br>VLR<br>(SEQ ID NO: 139) | CAGCCTGTGCTGACTCAGCCCCACTCTG<br>TGTCGGAGTCTCCGGGGAAGACGGTCA<br>CCATCTCCTGCACCCGCAGCAGTGGCA<br>GCATTGACAGCAACTTTGTGCAGTGGT<br>ACCAGCAGCGCCCGGGCAGTTCCCCCA<br>CCACTGTCATCTATGACGATAACCAGA<br>GGCCCTCTGGGGTCCCTGATCGGTTCTC<br>TGGCTCCATCGACAGCTCCTCCAACTCT<br>GCCTCCCTCACCATCTCTGGACTGAAG<br>ATTGAGGACGAGGCTGACTACTACTGT<br>CAGTCTTATGATAGCAACAATCAGGTG<br>TTCGGCGGCGGGACCAAGCTGACCGTC<br>CTACGT<br>(SEQ ID NO: 149) |
| 44-C12 | QTVVTQEPSFSVSPGGTVTLTCGLSSG<br>SVSPTYYPSWYQQTPGQAPRTLIYRT<br>NIRSSGVPDRFSGSILGNKAALTITGA<br>QADDESLYYCLLYMGSGVSLFGGGT<br>KLTVLR<br>(SEQ ID NO: 140) | CAGACTGTGGTGACTCAGGAGCCATCG<br>TTCTCAGTGTCCCCTGGAGGGACAGTC<br>ACACTCACTTGTGGCTTGAGCTCTGGCT<br>CAGTCTCTCCTACTTATTACCCCAGCTG<br>GTACCAGCAGACCCCAGGCCAGGCTCC<br>ACGCACGCTCATCTACAGGACAAACAT<br>TCGCTCTTCTGGGGTCCCTGATCGCTTC<br>TCTGGCTCCATCCTTGGGAACAAAGCT<br>GCCCTCACCATCACGGGGGCCCAGGCA<br>GATGATGAGTCTCTCTATTACTGTTTGC<br>TCTATATGGGTAGTGGCGTTTCGCTGTT<br>CGGCGGAGGGACCAAGCTGACCGTCCT<br>ACGT<br>(SEQ ID NO: 150) |
| 44-H4 | QAVVTQEPSFSVSPGGTVTLTCGLSSG<br>SVSTSYYPSWYQQTPGQAPRTLIYSTN<br>TRSSGVPDRFSGSILGNKAALTITGAQ<br>TDDESDYYCVLYMGSGISLFGGGTKV<br>TVLG<br>(SEQ ID NO: 141) | CAGGCTGTGGTGACCCAGGAGCCATCG<br>TTCTCAGTGTCCCCTGGAGGGACAGTC<br>ACACTCACTTGTGGCTTGAGCTCTGGCT<br>CAGTCTCTACTAGTTACTACCCCAGCTG<br>GTACCAGCAGACCCCAGGCCAGGCTCC<br>ACGCACGCTCATCTACAGCACAAACAC<br>TCGCTCCTCTGGGGTCCCTGATCGCTTC<br>TCTGGCTCCATCCTTGGGAACAAAGCT<br>GCCCTCACCATCACGGGGGCCCAGACA<br>GATGATGAATCTGATTATTACTGTGTGC<br>TGTATATGGGTAGTGGCATTTCGCTATT<br>CGGCGGAGGGACCAAGGTGACCGTCCT<br>AGGT<br>(SEQ ID NO: 151) |

Example 2

Preparation of Anti-c-Met/Anti-HER2 Bispecific Antibody

Each of the five anti-HER2 scFv fragments prepared in the above Example 1 was fused at the c-terminus of Fc of the anti-c-Met antibody L3-1Y-IgG2 prepared in the above Reference Example 1. The fusion procedures are as follows.

A DNA segment having the nucleotide sequence of SEQ ID NO: 66 corresponding to the heavy chain of the anti-c-Met antibody L3-1Y-IgG2 prepared in above Reference Example 1 was inserted into a pcDNA™3.3-TOPO TA Cloning Kit (Cat no. 8300-01) which is included in OptiCHO™ Antibody Express Kit (Cat no. 12762-019; Invitrogen Inc.), and a DNA segment having the nucleotide sequence of SEQ ID NO: 68 corresponding to the light chain of the anti-c-Met antibody L3-1Y-IgG2 was inserted into a pOptiVEC™-TOPO TA Cloning Kit. Thereafter, each of the anti-HER2 scFv coding DNAs prepared in Example 1 was fused at the c-terminal of Fc of L3-1Y-IgG2 inserted into pcDNA™3.3, using the coding DNA sequence of a linker peptide having 10 amino acid lengths consisting of (GGGGS)$_2$, to construct vectors for the expression of bispecific antibodies.

The constructed vectors were each amplified using Qiagen Maxiprep kit (Cat no. 12662) and their temporary expressions were performed using Freestyle™ MAX 293 Expression System (Invitrogen). A cell line used was 293 F cells, which were cultured in a suspension culture manner using FreeStyle™ 293 Expression Medium as a medium. One day before the temporary expression, the cells were prepared at a concentration of 5×10$^5$ cells/ml and after 24 hours, their temporary expression started when the number of the cells reached 1×10$^6$ cells/ml. Transfection was performed by a liposomal reagent method using Freestyle™

MAX reagent (Invitrogen). DNA was prepared in a 15 ml tube in a ratio of heavy chain DNA:light chain DNA=3:2 and mixed with 2 ml of OptiPro™ SFM (Invitrogen) (A), and 100 μL of Freestyle™ MAX reagent and 2 ml of OptiPro™ SFM were mixed in another 15-ml tube (B), and after (A) and (B) were mixed and incubated for 15 min., the mixture solution was then slowly mixed into the cells which were prepared one day before. After the transfection was complete, the cells were cultured in a 37° C., 80% humidity, 8% $CO_2$, 130 rpm incubator for 5 days.

The cultured cells were centrifuged to obtain each 100 ml of supernatants, which were then purified using AKTA Prime (GE healthcare). The culture was flowed at a flow rate of 5 ml/min onto the AKTA Prime installed with Protein A column (GE healthcare, 17-0405-03) to perform elution using an IgG elution buffer (Thermo Scientific, 21004). The buffer was replaced by a PBS buffer to finally obtain purified bispecific anti-c-Met/anti-HER2 antibodies.

The thus prepared anti-c-Met/anti-HER2 bispecific antibodies in which one of the five anti-HER2 scFv fragments is fused at the c-terminal of L3-1Y-IgG2 was named as MH2-12, MH2-13, MH2-14, MH2-16, and MH2-18, respectively. The anti-HER2 scFv fragments selected in Example 1 and anti-c-Met/anti-HER2 bispecific antibodies corresponding thereto are summarized in Table 10

TABLE 10

| HER2 scFv | Corresponding anti-c-Met/anti-HER2 bispecific antibody |
|---|---|
| 41-B11 | MH2-12 |
| 41-C6 | MH2-13 |
| 41-E1 | MH2-14 |
| 44-C12 | MH2-16 |
| 44-H4 | MH2-18 |

Example 3

Examination of Dual Binding of Anti-c-Met/Anti-HER2 Bispecific Antibody

To examine whether the anti-c-Met/anti-HER2 bispecific antibody recognizes both of the antigens, c-Met and HER2, the binding affinity to the two antigens were measured using Biacore T100 (GE). A human Fab binder (GE Healthcare) was immobilized onto a CM5 chip (#BR-1005-30, GE) according to the manufacturer's instructions. About 90 to 120 Ru of each bispecific antibody (MH2-12, MH2-13, MH2-14, MH2-16, or MH2-18) was captured, and c-Met-Fc (#358-MT/CF, R&D Systems) or HER2-Fc (#1129-ER, R&D Systems) were injected at various concentrations into the captured antibody. 10 mM Glycine-HCl (pH 2.1) solution was injected thereto to regenerate the surface. In order to measure affinity, the data obtained from this experiment was fitted using BlAevaluation software (GE Healthcare, Biacore T100 evaluation software).

The obtained results are shown in Tables 11 and 12.

TABLE 11

| Antibody | Antigen | $K_D$ (nM) | $k_a$ (1/Ms) | $k_d$ (1/s) |
|---|---|---|---|---|
| MH2-12 | Her2 | <0.01 | $2.0 \times 10^5$ | $<5.8 \times 10^{-5}$ |
| MH2-13 | | <0.01 | $3.6 \times 10^5$ | $<7.9 \times 10^{-5}$ |
| MH2-14 | | 6.6 | $2.5 \times 10^5$ | $1.6 \times 10^{-3}$ |

TABLE 11-continued

| Antibody | Antigen | $K_D$ (nM) | $k_a$ (1/Ms) | $k_d$ (1/s) |
|---|---|---|---|---|
| MH2-16 | | 1.16 | $5.8 \times 10^5$ | $6.7 \times 10^{-4}$ |
| MH2-18 | | <0.01 | $8.2 \times 10^5$ | $<1.3 \times 10^{-5}$ |

TABLE 12

| Antibody | Antigen | $K_D$ (nM) | $k_a$ (1/Ms) | $k_d$ (1/s) |
|---|---|---|---|---|
| MH2-12 | c-Met | 0.04 | $5.0 \times 10^5$ | $1.9 \times 10^{-5}$ |
| MH2-13 | | 0.09 | $4.8 \times 10^5$ | $4.4 \times 10^{-5}$ |
| MH2-14 | | 0.12 | $5.7 \times 10^5$ | $6.8 \times 10^{-5}$ |
| MH2-16 | | 0.04 | $8.7 \times 10^5$ | $3.6 \times 10^{-5}$ |
| MH2-18 | | 0.03 | $5.9 \times 10^5$ | $1.5 \times 10^{-5}$ |

As shown in Tables 11 and 12, all of the five bispecific antibodies have high affinities to c-Met and HER2.

Example 4

Examination of Cancer Cell Proliferation Inhibition by Anti-c-Met/Anti-HER2 Bispecific Antibody The cancer cell proliferation inhibition effects of the anti-c-Met/anti-HER2 bispecific antibody prepared in Example 2 were examined in a stomach cancer cell line MKN45, which was purchased from ATCC.

The cells were incubated in RPMI1640 medium (#11875-093, Gibco) supplemented with 10% (v/v) FBS and 1% (v/v) Penicillin-Streptomycin under the conditions of 5% $CO_2$ and 37° C. For cell proliferation assay, the cells were sub-cultured at a concentration of $5 \times 10^4$ cell/well in a 96-well plate, which was treated with each of the anti-c-Met/anti-HER2 bispecific antibodies prepared in Example 2 in an amount of 5 μg/ml, and cultured for 72 hours. A medium with no antibody treatment was used as a negative control (indicated as "medium"), and commercially available HER2 inhibitor Herceptin (Roche; 5 μg/ml) treated group, L3-1Y-IgG2 antibody (prepared in Reference Example; 5 μg/ml) treated group, and co-treated group of L3-1Y-IgG2 (5 μg/ml) and Herceptin (5 μg/ml) were each used as a positive control.

After incubation, cell proliferation degrees were analyzed using Cell Counting Kit-8 assay (Dojindo Molecular Technologies, Gaithersburg, Md.) according to the manufacturer's instructions. In brief, after the incubation for 72 hours, 10 μl (microliter) of CCK8 solution was added to each well and after the additional incubation for 2.5 hours, absorption degrees were read at 450 nm using a microplate reader.

Figure 2:
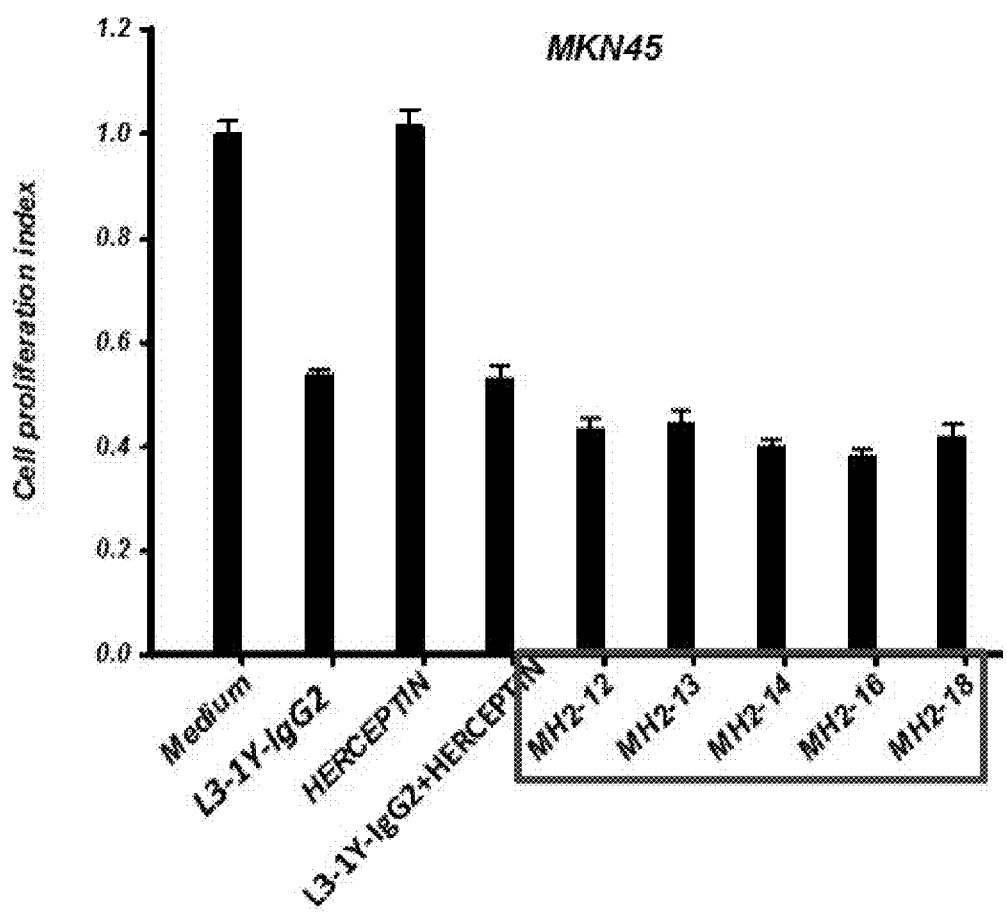
FIG. 2 is a graph showing the cell growth of cancer cells (gastric cancer cell line MKN45) when treated with antibodies including an anti-c-Met/anti-HER2 bispecific antibody.

The obtained results are shown in FIG. 2. As seen in FIG. 2, all the five anti-c-Met/anti-HER2 bispecific antibodies showed remarkable increases in cell proliferation inhibitory effects, compared to the cases treated individually with the anti-c-Met antibody L3-1Y-IgG2 and the anti-HER2 antibody Herceptin™. In particular, the anti-c-Met/anti-HER2 bispecific antibodies showed excellent cell proliferation inhibitory effects, even compared to the co-treatment case (L3-1Y-IgG2+Herceptin™), which is not a form of bispecific antibody.

Example 5

Simultaneous Internalization of Dual Targets (c-Met and HER2) by Anti-c-Met/Anti-HER2 Bispecific Antibodies MKN45 cells (ATCC) were provided at the amount of $4 \times 10^4$ cell/well, and treated with no antibody (control) or each of anti-c-Met/anti-HER2 bispecific antibodies (MH2-12, MH2-13, MH2-14, MH2-16, and MH2-18), wherein each antibody was treated at the amount of 5 µg/ml per well under 37° C. for 4 hours. The cells were treated with 4%(v/v) formaldehyde for 15 minutes to be immobilized on a plate, and washed three times with PBS. Thereafter, the cells were treated with a blocking buffer (0.5% triton x-100 and 5% donkey serum) at a room temperature for one hour and then treated with a 1:100 dilution of primary antibodies against each of c-Met and HER2 (c-Met primary antibody; #FAB3582A, R&D systems, HER2 primary antibody; #2165, Cell signaling), respectively in the amount of 100 µl, at 4° C. for 15 hours. After the cells were washed three time with PBS, they were treated with a 1:2000 dilution of a secondary antibody (#A21433, Invitrogen) in an amount of 100 µl at a room temperature for 1 hour and washed three times with PBS to prepare a plate with a mounting medium (#H-1200, Vector Labs). The prepared cells were observed with a confocal microscope (Zeiss, LSM710).

Figure 3:
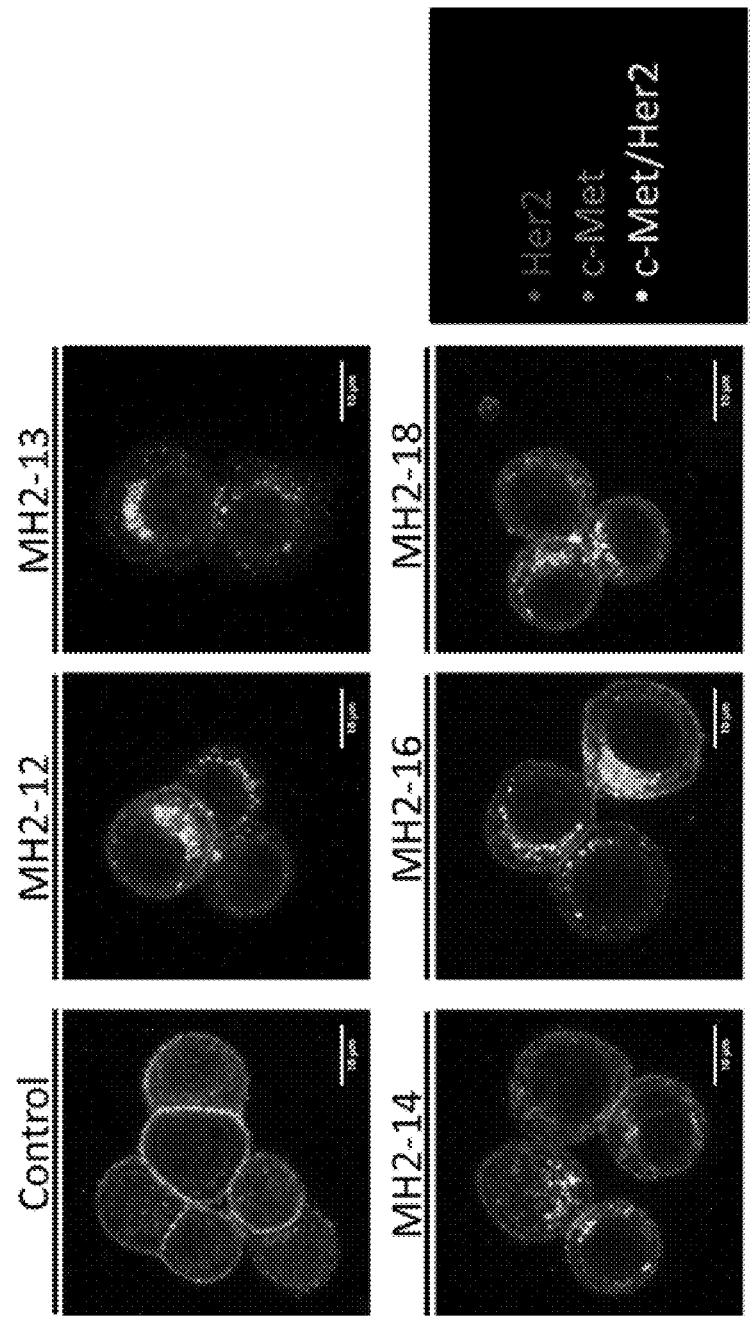
FIG. 3 is a series of fluorescence microscopic images of MKN45 gastric cancer cells showing internalization and co-localization of c-Met and HER2 after treating an anti-c-Met/anti-HER2 bispecific antibody.

The obtained results are shown in FIG. 3. As seen in FIG. 3, when the anti-c-Met/anti-HER2 bispecific antibody (MH2-12, MH2-13, MH2-14, MH2-16, or MH2-18) is treated, both of c-Met and HER2 are moved into the cells.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-HER2 antibody or an antigen-binding fragment thereof, comprising:
   (1) a CDR-H1 comprising SEQ ID NO: 109, a CDR-H2 comprising SEQ ID NO: 112, and a CDR-H3 comprising SEQ ID NO: 115; and
   a CDR-L1 comprising SEQ ID NO: 120, a CDR-L2 comprising SEQ ID NO: 124, and a CDR-L3 comprising SEQ ID NO: 127; or
   (2) a CDR-H1 comprising SEQ ID NO: 109, a CDR-H2 comprising SEQ ID NO: 112, and a CDR-H3 comprising SEQ ID NO: 116; and
   a CDR-L1 comprising SEQ ID NO: 121, a CDR-L2 comprising SEQ ID NO: 124, and a CDR-L3 comprising SEQ ID NO: 128;
   (3) a CDR-H1 comprising SEQ ID NO: 110, a CDR-H2 comprising SEQ ID NO: 113, and a CDR-H3 comprising SEQ ID NO: 117; and
   a CDR-L1 comprising SEQ ID NO: 122, a CDR-L2 comprising SEQ ID NO: 125, and a CDR-L3 comprising SEQ ID NO: 129;
   (4) a CDR-H1 comprising SEQ ID NO: 111, a CDR-H2 comprising SEQ ID NO: 114, and a CDR-H3 comprising SEQ ID NO: 118; and
   a CDR-L1 comprising SEQ ID NO: 123, a CDR-L2 comprising SEQ ID NO: 126, and a CDR-L3 comprising SEQ ID NO: 130;
   or
   (5) a CDR-H1 comprising SEQ ID NO: 109, a CDR-H2 comprising SEQ ID NO: 112, and a CDR-H3 comprising SEQ ID NO: 119; and
   a CDR-L1 comprising SEQ ID NO: 120, a CDR-L2 comprising SEQ ID NO: 124, and a CDR-L3 comprising SEQ ID NO: 131.

2. The anti-HER2 antibody or the antigen-binding fragment thereof of claim 1, comprising:
   (1) a heavy chain variable region comprising SEQ ID NO: 132, and
   a light chain variable region comprising SEQ ID NO: 137;
   (2) a heavy chain variable region comprising SEQ ID NO: 133, and
   a light chain variable region comprising SEQ ID NO: 138;
   (3) a heavy chain variable region comprising SEQ ID NO: 134, and
   a light chain variable region comprising SEQ ID NO: 139;
   (4) a heavy chain variable region comprising SEQ ID NO: 135, and
   a light chain variable region comprising SEQ ID NO: 140;
   or
   (5) a heavy chain variable region comprising SEQ ID NO: 136, and
   a light chain variable region SEQ ID NO: 141.

3. The anti-HER2 antibody or the antigen-binding fragment thereof of claim 2, wherein the anti-HER2 antibody or the antigen binding fragment is an anti-HER2 scFv.

4. An anti-c-Met/anti-HER2 bispecific antibody comprising
   (1) an anti-c-Met antibody or an antigen-binding fragment thereof and
   (2) an anti-HER2 antibody or an antigen-binding fragment thereof of claim 1.

5. The anti-c-Met/anti-HER2 bispecific antibody of claim 4, wherein the anti-c-Met antibody or the antigen-binding fragment thereof comprises:
   (1) a CDR-H1 comprising SEQ ID NO: 1;
   a CDR-H2 comprising SEQ ID NO: 2;
   a CDR-H3 comprising SEQ ID NO: 3;
   a CDR-L1 comprising SEQ ID NO: 10;
   a CDR-L2 comprising SEQ ID NO: 11; and
   a CDR-L3 comprising SEQ ID NO: 13, 14, 15, or 16;
   or
   (2) a CDR-H1 comprising SEQ ID NO: 1;
   a CDR-H2 comprising SEQ ID NO: 2;
   a CDR-H3 comprising SEQ ID NO: 3;
   a CDR-L1 comprising SEQ ID NO: 106;
   a CDR-L2 comprising SEQ ID NO: 11; and
   a CDR-L3 comprising SEQ ID NO: 13.

6. The anti-c-Met/anti-HER2 bispecific antibody of claim 5, wherein the anti-c-Met antibody or the antigen-binding fragment thereof comprises:
a heavy chain variable region comprising the amino acid sequence of SEQ ID NO: 17, and
a light chain variable region comprising the amino acid sequence of SEQ ID NO: 162, 18, 19, 20, 21, or 107.

7. The anti-c-Met/anti-HER2 bispecific antibody of claim 5, wherein the anti-c-Met antibody comprises:
a heavy chain comprising an amino acid sequence selected from the group consisting of SEQ ID NO: 62, the amino acid sequence from the $18^{th}$ to $462^{nd}$ positions of SEQ ID NO: 62, SEQ ID NO: 64, the amino acid sequence from the $18^{th}$ to $461^{st}$ positions of SEQ ID NO: 64, SEQ ID NO: 66, and the amino acid sequence from the $18^{th}$ to $460^{th}$ positions of SEQ ID NO: 66; and
a light chain comprising an amino acid sequence selected from the group consisting of SEQ ID NO: 68, the amino acid sequence from the $21^{st}$ to $240^{th}$ positions of SEQ ID NO: 68, SEQ ID NO: 70, the amino acid sequence from the $21^{st}$ to $240^{th}$ positions of SEQ ID NO: 70, and SEQ ID NO: 108.

8. The anti-c-Met/anti-HER2 bispecific antibody of claim 4, wherein the anti-HER2 antibody or the antigen-binding fragment thereof comprises:
(1) a heavy chain variable region comprising SEQ ID NO: 132, and
a light chain variable region comprising SEQ ID NO: 137;
(2) a heavy chain variable region SEQ ID NO: 133, and
a light chain variable region comprising SEQ ID NO: 138;
(3) a heavy chain variable region comprising SEQ ID NO: 134, and
a light chain variable region comprising SEQ ID NO: 139;
(4) a heavy chain variable region comprising SEQ ID NO: 135, and
a light chain variable region comprising SEQ ID NO: 140; or
(5) a heavy chain variable region comprising SEQ ID NO: 136, and
a light chain variable region comprising SEQ ID NO: 141.

9. The anti-c-Met/anti-HER2 bispecific antibody of claim 4, wherein the antigen-binding fragment of the anti-HER2 antibody is an anti-HER2 scFv, and the anti-HER2 scFv is linked to C-terminus of the anti-c-Met antibody.

10. A method of treating a cancer comprising administering the anti-HER2 antibody or the antigen-binding fragment thereof of claim 1 to a subject in need of cancer treatment.

11. A method of treating a cancer comprising administering the anti-c-Met/anti-HER2 bispecific antibody of claim 4 to a subject in need of cancer treatment.

12. A pharmaceutical composition comprising the anti-HER2 antibody or the antigen-binding fragment thereof of claim 1 and a pharmaceutically acceptable carrier.

13. A pharmaceutical composition comprising the anti-c-Met/anti-HER2 bispecific antibody of claim 4 and a pharmaceutically acceptable carrier.

14. The anti-HER2 antibody or the antigen-binding fragment thereof of claim 1, comprising:
a CDR-H1 comprising SEQ ID NO: 109, a CDR-H2 comprising SEQ ID NO: 112, and a CDR-H3 comprising SEQ ID NO: 115; and
a CDR-L1 comprising SEQ ID NO: 120, a CDR-L2 comprising SEQ ID NO: 124, and a CDR-L3 comprising SEQ ID NO: 127.

15. The anti-HER2 antibody or the antigen-binding fragment thereof of claim 1, comprising:
a CDR-H1 comprising SEQ ID NO: 109, a CDR-H2 comprising SEQ ID NO: 112, and a CDR-H3 comprising SEQ ID NO: 116; and
a CDR-L1 comprising SEQ ID NO: 121, a CDR-L2 comprising SEQ ID NO: 124, and a CDR-L3 comprising SEQ ID NO: 128.

16. The anti-HER2 antibody or the antigen-binding fragment thereof of claim 1, comprising:
a CDR-H1 comprising SEQ ID NO: 110, a CDR-H2 comprising SEQ ID NO: 113, and a CDR-H3 comprising SEQ ID NO: 117; and
a CDR-L1 comprising SEQ ID NO: 122, a CDR-L2 comprising SEQ ID NO: 125, and a CDR-L3 comprising SEQ ID NO: 129.

17. The anti-HER2 antibody or the antigen-binding fragment thereof of claim 1, comprising:
a CDR-H1 comprising SEQ ID NO: 111, a CDR-H2 comprising SEQ ID NO: 114, and a CDR-H3 comprising SEQ ID NO: 118; and
a CDR-L1 comprising SEQ ID NO: 123, a CDR-L2 comprising SEQ ID NO: 126, and a CDR-L3 comprising SEQ ID NO: 130.

18. The anti-HER2 antibody or the antigen-binding fragment thereof of claim 1, comprising:
a CDR-H1 comprising SEQ ID NO: 109, a CDR-H2 comprising SEQ ID NO: 112, and a CDR-H3 comprising SEQ ID NO: 119; and
a CDR-L1 comprising SEQ ID NO: 120, a CDR-L2 comprising SEQ ID NO: 124, and a CDR-L3 comprising SEQ ID NO: 131.

* * * * *